United States Patent
Stevenson et al.

(10) Patent No.: US 9,764,129 B2
(45) Date of Patent: Sep. 19, 2017

(54) RF FILTER ON A CIRCUIT BOARD FOR AN ACTIVE MEDICAL DEVICE (AMD) FOR HANDLING HIGH RF POWER INDUCED IN AN ASSOCIATED IMPLANTED LEAD FROM AN EXTERNAL RF FIELD

(71) Applicant: Greatbatch Ltd., Clarence, NY (US)

(72) Inventors: Robert A. Stevenson, Canyon Country, CA (US); Robert Shawn Johnson, North Tonawanda, NY (US); Warren S. Dabney, Lake Oswego, OR (US); Thomas Marzano, East Amherst, NY (US); Richard L. Brendel, Carson City, NV (US); Christopher Michael Williams, Alden, NY (US); Holly Noelle Moschiano, Williamsville, NY (US); Keith W. Seitz, Clarence Center, NY (US); John E. Roberts, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 15/163,241

(22) Filed: May 24, 2016

(65) Prior Publication Data
US 2016/0263373 A1 Sep. 15, 2016

Related U.S. Application Data

(63) Continuation of application No. 14/688,302, filed on Apr. 16, 2015, which is a continuation-in-part of
(Continued)

(51) Int. Cl.
*A61N 1/08* (2006.01)
*A61N 1/375* (2006.01)
(Continued)

(52) U.S. Cl.
CPC ............ *A61N 1/08* (2013.01); *A61N 1/3718* (2013.01); *A61N 1/3754* (2013.01);
(Continued)

(58) Field of Classification Search
CPC ...... A61N 1/08; A61N 1/3718; A61N 1/3754; A61N 1/3758; A61N 2001/086;
(Continued)

(56) References Cited

U.S. PATENT DOCUMENTS 5,333,095 A * 7/1994 Stevenson ............ A61N 1/3754
29/25.42
5,978,204 A 11/1999 Stevenson
(Continued)

OTHER PUBLICATIONS

Wikipedia article on EIA_Class_I_dielectric (http://en.wikipedia.org/wiki/EIA_Class_1_dielectric, captured Sep. 13, 2006).*
(Continued)

*Primary Examiner* — Carl H Layno
*Assistant Examiner* — Erin M Piateski
(74) *Attorney, Agent, or Firm* — Michael F. Scalise

(57) ABSTRACT

An AIMD includes a conductive housing, an electrically conductive ferrule with an insulator hermetically sealing the ferrule opening. A conductive pathway is hermetically sealed and disposed through the insulator. A filter capacitor is disposed on a circuit board within the housing and has a dielectric body supporting at least two active and two ground electrode plates interleaved, wherein the at least two active electrode plates are electrically connected to the conductive pathway on the device side, and the at least two ground electrode plates are electrically coupled to either the ferrule and/or the conductive housing. The dielectric body has a dielectric constant less than 1000 and a capacitance of between 10 and 20,000 picofarads. The filter capacitor is configured for EMI filtering of MRI high RF pulsed power by a low ESR, wherein the ESR of the filter capacitor at an
(Continued)

MRI RF pulsed frequency or range of frequencies is less than 2.0 ohms.

24 Claims, 46 Drawing Sheets

Related U.S. Application Data application No. 14/187,297, filed on Feb. 23, 2014, now Pat. No. 9,014,808, which is a continuation of application No. 14/088,849, filed on Nov. 25, 2013, now Pat. No. 8,855,768, which is a continuation of application No. 13/408,020, filed on Feb. 29, 2012, now abandoned.

(60) Provisional application No. 61/448,069, filed on Mar. 1, 2011.

(51) Int. Cl.
  *A61N 1/37* (2006.01)
  *H01G 4/005* (2006.01)
  *H01G 4/12* (2006.01)
  *H01G 4/30* (2006.01)
  *H01G 4/35* (2006.01)
  *H03H 1/00* (2006.01)

(52) U.S. Cl.
  CPC ........... *A61N 1/3758* (2013.01); *H01G 4/005* (2013.01); *H01G 4/12* (2013.01); *H01G 4/30* (2013.01); *H01G 4/35* (2013.01); *A61N 2001/086* (2013.01); *H03H 1/0007* (2013.01)

(58) Field of Classification Search
  CPC    H01G 4/005; H01G 4/12; H01G 4/30; H01G 4/35; H03H 1/0007
  USPC ......................................................... 607/36
  See application file for complete search history.

(56) References Cited

U.S. PATENT DOCUMENTS

| | | | |
|---|---|---|---|
| 6,539,253 B2 | 3/2003 | Thompson et al. | |
| 6,765,779 B2 | 7/2004 | Stevenson | |
| 6,925,328 B2 | 8/2005 | Foster et al. | |
| 7,363,090 B2 | 4/2008 | Halperin et al. | |
| 7,387,928 B2 | 6/2008 | Cheung | |
| 7,517,769 B2 | 4/2009 | Van Schuylenbergh et al. | |
| 7,689,288 B2 | 3/2010 | Stevenson et al. | |
| 7,844,319 B2 | 11/2010 | Susil et al. | |
| 7,853,324 B2 | 12/2010 | Stevenson et al. | |
| 8,095,224 B2 | 1/2012 | Truex et al. | |
| 8,653,384 B2 | 2/2014 | Marzano et al. | |
| 2003/0050557 A1 | 3/2003 | Susil et al. | |
| 2003/0053284 A1* | 3/2003 | Stevenson ................ | H01G 4/35 361/302 |
| 2003/0171792 A1 | 9/2003 | Zarinetchi et al. | |
| 2003/0179536 A1 | 9/2003 | Stevenson et al. | |
| 2003/0213605 A1* | 11/2003 | Brendel ................... | H01G 4/35 174/360 |
| 2005/0007718 A1 | 1/2005 | Stevenson et al. | |
| 2005/0248907 A1 | 11/2005 | Stevenson et al. | |
| 2006/0028784 A1 | 2/2006 | Brendel | |
| 2006/0221543 A1 | 10/2006 | Stevenson et al. | |
| 2007/0035910 A1 | 2/2007 | Stevenson | |
| 2007/0112398 A1* | 5/2007 | Stevenson ................ | A61N 1/05 607/63 |
| 2008/0140149 A1 | 6/2008 | John et al. | |
| 2009/0036944 A1 | 2/2009 | Fonte | |
| 2009/0270948 A1 | 10/2009 | Nghiem et al. | |
| 2009/0312835 A1 | 12/2009 | Stevenson | |
| 2010/0023000 A1* | 1/2010 | Stevenson .......... | A61B 18/1492 606/33 |
| 2010/0198312 A1 | 8/2010 | Stevenson et al. | |
| 2010/0217262 A1 | 8/2010 | Stevenson et al. | |
| 2010/0241206 A1 | 9/2010 | Truex et al. | |
| 2014/0168850 A1 | 6/2014 | Stevenson et al. | |

OTHER PUBLICATIONS

Sakabe et al. "High Frequency Performance of Multilayer Ceramic Capacitors", Electronic Components and Technology Conference, 1995. Proceedings. May 21-24, 1995, pp. 234-240.*

Holy Stone Enterprise "Ceramic Capacitor Catalog 2008-2009", May 2008.*

Balanis, "Advanced Engineering Electromagnetics", 1989.

Boser, et al., "High Frequency Behavior of Ceramic Multilayer Capacitors", IEEE Transactions on components, Hybrids, and Manufacturing Technology, vol. CHMT-10, No. 3, Sep. 1987, 437-439.

Ennis, et al., "Cautions About the Use of Equivalent Series Resistance (ESR) in Specifying Capacitors", Mar. 8, 1993, 58-64.

Gabriel, et al., "The Dielectric Properties of Biological Tissues: II.", Measurements in the Frequency Range 10 Hz to 20 GHz, Apr. 2, 1996, 2251-2269.

Gabriel, et al., "The Dielectric Properties of Biological Tissues: Parametric Models for the Dielectric Spectrum of Tissues", Parametric Models for the Dielectric Spectrum of Tissues Phys. Med. Bio. 41, 1996, 2271-2293.

Sakabe, et al., "High Frequency Performance of Multilayer Ceramic Capacitors", Electronic Components and Technology Confrerence, 1995, Proceedings 45th, May 21, 1995, 234-240.

Sarda, et al., "Ceramic EMI Filters—A Review", American Ceramic Society Bulletin; vol. 67, No. 4, 1988, 737-746.

Search, "European Search Report", Application No. 12157697.9 dated Jul. 5, 2012, Jul. 5, 2012.

Susil, et al., "Multifunctional Interventional Devices for MRI: A Combined Electrophysiology/MRI Catheter", 2002, 594-600.

European Search Report, Application 15165863.0, dated Sep. 12, 2016.

Extended European Search, Application 16175505.3, dated Nov. 15, 2016.

Holy Stone Enterprise Co., Ltd.; "HCN Series-High Cap NPO"; Cover page, Table of Contents p. 2, pp. 41-44, back page; May 2008; Ceramic Capacitor Catalog 2008-2009; Holy Stone Enterprise Co., Ltd.; URL listing: http://www.holystoneeurope.com/PDF/HEC_2008-2009_Catalog.pdf.†

Ivan G. Sarda et al.; "Ceramic EMI Filters—A Review"; pp. 737-746; 1988; American Ceramic Society Bulletin, vol. 67, No. 4, Westerville, Ohio; ISSN: 0002-7812; URL listing: http://cat.inist.fr/?aModele=afficheN&cpsidt=7156148.†

Otmar Boser et al.; "High Frequency Behavior of Ceramic Multilayer Capacitors"; pp. 437-439; Sep. 1987; IEEE Transactions on Components, Hybrids, and Manufacturing Technology, vol. CHMT-10, No. 3; ISSN: 0148-6411; URL listing: http://ieeexplore.ieee.org/xpl/login.jsp?tp=&arnumber=1134747&url=http%3A%2F%2Fieeexplore.ieee.org%2Fxpls%2Fabs_all.jsp%3Farnumber%3D2134747.†

Yukio Sakabe et al.; "High Frequency Performance of Multilayer Ceramic Capacitors"; pp. 234-240; published May 21, 1995; Electronic Components and Technology Conference, 1995, Proceedings 45th; Print ISBN: 0-7803-2736-5; URL listing: http://ieeexplore.ieee.org/xpl/login.jsp?tp=&arnumber=514390&url=http%3A%2F%2Fieeexplore.ieee.org%2Fxpls%2Fabs_all.jsp%3Farnumber%3D514390.†

\* cited by examiner
† cited by third party

BODY
FLUID
SIDE

BODY
FLUID
SIDE

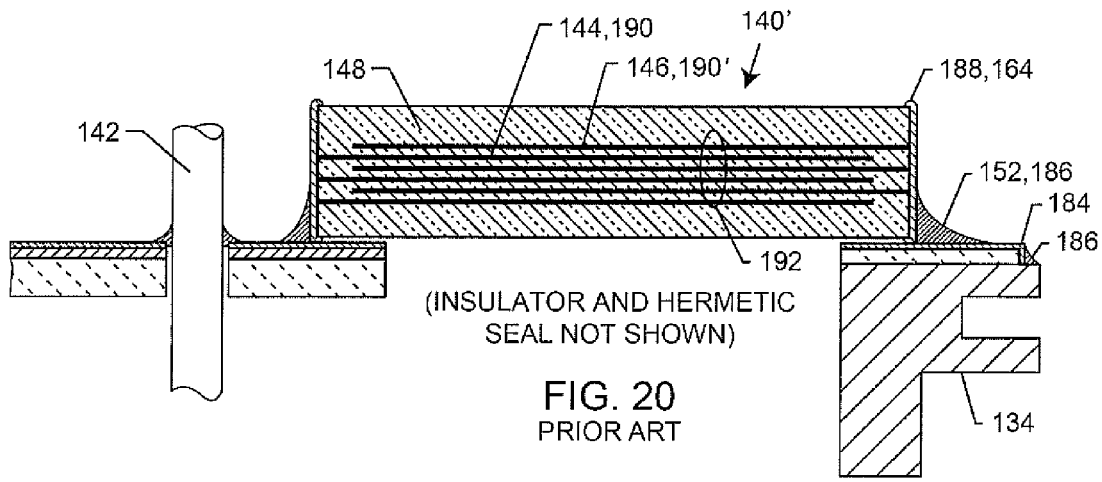
(INSULATOR AND HERMETIC SEAL NOT SHOWN)
FIG. 20
PRIOR ART
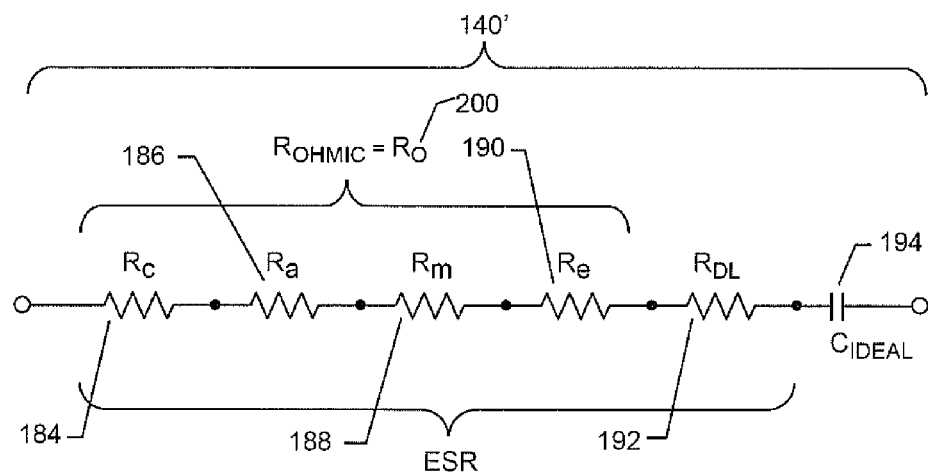
FIG. 21
FIG. 22
$$C = \frac{kA\ (n-1)}{d}$$
Where
A = Active Area
C = Capacitance
$k$ = Dielectric Constant
n = Number of Electrode Plates
d = Dielectric Thickness $$X_c = -j\left(\frac{1}{\omega C}\right)$$

$$z = \sqrt{X_c^2 + (ESR)^2}$$

$$DF = \frac{i^2 \, ESR}{i^2 \, |X_c|} = (\omega C) \cdot (ESR) = 1/Q$$

$$\tan\delta = \frac{ESR}{|X_c|} = DF$$

C = Capacitance
$R_{DL}$ = R dielectric
$R_O$ = R ohmic loss
IR = Insulation Resistance
ESL = Equivalent Series Inductance
ESR = Equivalent Series Resistance Example of Losses in a 2000 P.F. X7R Capacitor DF is a percentage of Xc ≈ dielectric loss tangent Example: 2% DF Dielectric; 2000 picofarad FT   (2.5% MAX Per EIA RS-198C)

| Frequency | Xc (Ω) | DF (Ω) | R (Ω) | ESR = DF+R (Ω) |
|---|---|---|---|---|
| 1 kHz | 79,599.54 | 1591.55 | 0.432 | 1591.98 |
| 1 MHz | 79.58 | 1.59 | 0.432 | 2.02 |
| 10 MHz | 7.96 | 0.159 | 0.432 | 0.59 |
| 100 MHz | 0.796 | 0.016 | 0.432 | 0.45 |
| 500 MHz | 0.159 | 0.003 | 0.432 | 0.44 |

FIG. 29

Example of Losses in a 2000 P.F. COG (NPO) Capacitor

DF is a percentage of Xc

Example: 0.15% DF Dielectric; 2000 picofarad FT

| Frequency | Xc (Ω) | DF (Ω) | R (Ω) | ESR = DF+R (Ω) |
|---|---|---|---|---|
| 1 kHz | 79,577.54 | 119.40 | 0.2 | 119.6 |
| 1 MHz | 79.58 | 0.12 | 0.2 | 0.32 |
| 10 MHz | 7.96 | 0.012 | 0.2 | 0.212 |
| 100 MHz | 0.796 | 0.001 | 0.2 | 0.201 |
| 500 MHz | 0.159 | 0.0 | 0.2 | 0.200 |

FIG. 30

(INSULATOR AND HERMETIC SEAL NOT SHOWN)

BODY FLUID SIDE $$R_{et} = \cfrac{1}{\cfrac{1}{R_{e_1}} + \cfrac{1}{R_{e_2}} + \cdots \cfrac{1}{R_{e_n}}}$$

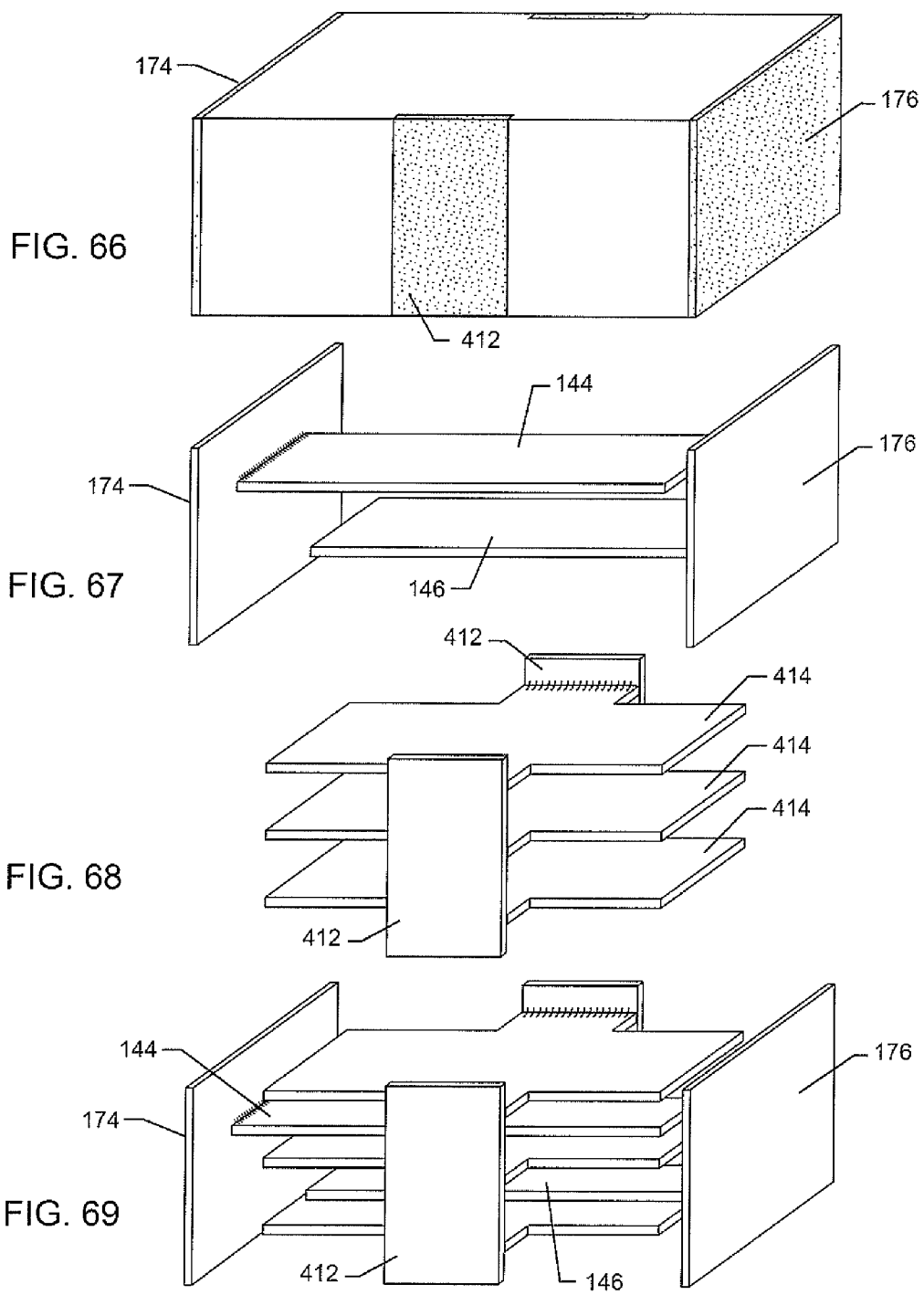

RF FILTER ON A CIRCUIT BOARD FOR AN ACTIVE MEDICAL DEVICE (AMD) FOR HANDLING HIGH RF POWER INDUCED IN AN ASSOCIATED IMPLANTED LEAD FROM AN EXTERNAL RF FIELD

CROSS-REFERENCE TO RELATED APPLICATIONS

The instant application is a continuation of U.S. patent application Ser. No. 14/688,302, filed on Apr. 16, 2015, which is a continuation-in-part application claiming priority to U.S. patent application Ser. No. 14/187,297, filed on Feb. 23, 2014, now U.S. Pat No. 9,014,808, which was a continuation application claiming priority to U.S. patent application Ser. No. 14/088,849, filed on Nov. 25, 2013, now U.S. Pat. No. 8,855,768, which was a continuation application of U.S. patent application Ser. No. 13/408,020, filed on Feb. 29, 2012, abandoned, which claimed priority to U.S. Provisional Application Ser. No. 61/448,069, filed on Mar. 1, 2011, the contents of which are fully incorporated herein with these references.

FIELD OF THE INVENTION

This invention generally relates to the problem of RF energy induced into implanted leads during medical diagnostic procedures such as magnetic resonant imaging (MRI), and provides methods and apparatus for redirecting RF energy to locations other than the distal tip electrode-to-tissue interface. In addition, the present invention provides electromagnetic interference (EMI) protection to sensitive active implantable medical device (AIMD) electronics.

BACKGROUND OF THE INVENTION

Compatibility of cardiac pacemakers, implantable defibrillators and other types of active implantable medical devices with magnetic resonance imaging (MRI) and other types of hospital diagnostic equipment has become a major issue. If one proceeds to the websites of the major cardiac pacemaker manufacturers in the United States, which include St. Jude Medical, Medtronic and Boston Scientific (formerly Guidant), one will see that the use of MRI is generally contra-indicated for patients with implanted pacemakers and cardioverter defibrillators. See also recent press announcements of the Medtronic Revo MRI pacemaker which was recently approved by the U.S. FDA. With certain technical limitations as to scan type and location, this is the first pacemaker designed for MRI scanning. See also:
(1) "Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "1. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel;
(5) "Advanced Engineering Electromagnetics", C. A. Balanis, Wiley, 1989;
(6) Systems and Methods for Magnetic-Resonance-Guided Interventional Procedures, Patent Application Publication US 2003/0050557, Susil and Halperin et al., published Mar. 13, 2003;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, U.S. Pat. No. 7,844,534, Susil et al., issued Nov. 30, 2010. The contents of the foregoing are all incorporated herein by reference.

However, an extensive review of the literature indicates that, despite being contra-indicated, MRI is indeed often used to image patients with pacemaker, neurostimulator and other active implantable medical devices (AIMDs). As such, the safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the International Society for Magnetic Resonance in Medicine (ISMRM), which was held on 5-6 Nov. 2005, it was reported that certain research systems are going up as high as 11.7 Tesla and will be ready sometime in 2010. This is over 100,000 times the magnetic field strength of the earth. A static magnetic field can induce powerful mechanical forces and torque on any magnetic materials implanted within the patient. This would include certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of about 21 MHz to about 500 MHz depending upon the static magnetic field strength. The frequency of the RF pulse for hydrogen scans varies by the Lamour equation with the field strength of the main static field where: RF PULSED FREQUENCY in MHz=(42.56) (STATIC FIELD STRENGTH IN TESLA). There are also phosphorous and other types of scanners wherein the Lamour equation would be different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 2-5 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted lead system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted lead systems actually act as antennas where voltages (EMFs) are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the leadwire system (for example, at the header block of a cardiac pacemaker). This has to do with the wavelength of the signals involved and where they couple efficiently into the system.

Magnetic field coupling into an implanted lead system is based on loop areas. For example, in a cardiac pacemaker unipolar lead, there is a loop formed by the lead as it comes from the cardiac pacemaker housing to its distal tip electrode, for example, located in the right ventricle. The return path is through body fluid and tissue generally straight from the tip electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal pacemaker implant, the implanted loop area is much larger (around 400 square centimeters).

Relating now to the specific case of MRI, the magnetic gradient fields would be induced through enclosed loop areas. However, the pulsed RF fields, which are generated by the body coil, would be primarily induced into the lead system by antenna action. Subjected to RF frequencies, the lead itself can exhibit complex transmission line behavior.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur. Also, distal tip design is very important as it can heat up due to MRI RF induced energy.

The cause of heating in an MRI environment is twofold: (a) RF field coupling to the lead can occur which induces significant local heating; and (b) currents induced between the distal tip and tissue during MRI RF pulse transmission sequences can cause local Ohms Law (resistive) heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD lead geometries. There can also be localized heating problems associated with various types of electrodes in addition to tip electrodes. This includes ring electrodes or pad electrodes. Ring electrodes are commonly used with a wide variety of implanted devices including cardiac pacemakers, and neurostimulators, and the like. Pad electrodes are very common in neurostimulator applications. For example, spinal cord stimulators or deep brain stimulators can include at least ten pad electrodes to make contact with nerve tissue. A good example of this also occurs in a cochlear implant. In a typical cochlear implant there would be sixteen pad electrodes placed up into the cochlea. Several of these pad electrodes make contact with auditory nerves.

Although there are a number of studies that have shown that MRI patients with active implantable medical devices, such as cardiac pacemakers, can be at risk for potential hazardous effects, there are a number of reports in the literature that MRI can be safe for imaging of pacemaker patients when a number of precautions are taken (only when an MRI is thought to be an absolute diagnostic necessity). While these anecdotal reports are of interest, they are certainly not scientifically convincing that all MRI can be safe. For example, just variations in the pacemaker lead length and implant trajectory can significantly affect how much heat is generated. A paper entitled, HEATING AROUND INTRAVASCULAR GUIDEWIRES BY RESONATING RF WAVES by Konings, et al., journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the function of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar and the like. It is very important that excessive current not flow at the interface between the lead distal tip electrode and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. Excessive current at the distal electrode to tissue interface can cause excessive heating to the point where tissue ablation or even perforation can occur. This can be life threatening for cardiac patients. For neurostimulator patients, such as deep brain stimulator patients, thermal injury can cause coma, permanent disability or even be life threatening. Similar issues exist for spinal cord stimulator patients, cochlear implant patients and the like.

Interestingly, the inventors performed an experiment in an MRI scanner with a human body gel-filled phantom. In the phantom, placed in an anatomic position, was an operating pacemaker and a lead. This was during evaluation of the efficacy of bandstop filters at or near the distal tip electrode for preventing the distal tip electrode from overheating. Bandstop filters for this purpose are more thoroughly described in U.S. Pat. No. 7,363,090, the contents of which are incorporated herein by reference. During the experiments, there was a control lead that had no bandstop filter. During a particularly RF intense scanning sequence, Luxtron probes measured a distal helix tip electrode temperature rise of 30 degrees C. Of course, the 30 degrees C. temperature rise in a patient, would be very alarming as it could lead to pacing capture threshold changes or even complete loss capture due to scar tissue formation. An identical lead with the bandstop filter in place only had a temperature rise of 3 degrees C. This was a remarkable validation of the efficacy of bandstop filters for implantable electrodes. However, something very interesting happened when we disconnected the pacemaker. We disconnected the pacemaker and put a silicone lead cap over the proximal end of the lead. Again, we put the gel phantom back inside the MR scanner and this time we measured an 11 degree C. temperature rise on the lead with the bandstop filter. This was proof positive that the housing of the AIMD acts as part of the system. The prior art feedthrough capacitor created a fairly low impedance at the input to the pacemaker and thereby drew RF energy out of the lead and diverted it to the housing of the pacemaker. It has recently been discovered that the impedance, and in particular, the ESR of these capacitors, is very important so that maximal energy can be pulled from the lead and diverted to the pacemaker housing while at the same time, not unduly overheating the feedthrough capacitor.

Accordingly, there is a need for novel low ESR diverting capacitors and circuits which are frequency selective and are constructed of passive components for implantable leads and/or leadwires. Further, there is a need for very low ESR diverter element capacitor(s) which are designed to decouple a maximum amount of induced RF energy from an implanted lead to an AIMD housing while at the same time not overheat. The present invention fulfills these needs and provides other related advantages.

SUMMARY OF THE INVENTION

An embodiment of an active implantable medical device (AIMD) includes a conductive housing. The housing defines a body fluid side located outside the conductive housing and defines a device side located inside the conductive housing. An electrically conductive ferrule is hermetically sealed to a housing opening in the conductive housing. The ferrule has a ferrule opening passing through the ferrule between the body fluid side and the device side. An insulator hermetically seals the ferrule opening. A conductive pathway is hermetically sealed and disposed through the insulator between the body fluid side and the device side. The conductive pathway is in non-conductive relation with the ferrule. The conductive pathway on the body fluid side is connectable to an implantable lead conductor with at least one electrode. A filter capacitor is disposed within the conductive housing on the device side. The filter capacitor includes a dielectric body supporting at least two active electrode plates interleaved with at least two ground electrode plates, wherein the at least two active electrode plates are electrically connected to the conductive pathway on the device side, and the at least two ground electrode plates are electrically coupled to either the ferrule and/or the conductive housing. The filter capacitor also has a dielectric body with a dielectric constant less than 1000. A capacitance is between 10 and 20,000 picofarads. The filter capacitor is configured for EMI filtering of MRI high RF pulsed power by a low equivalent series resistance (ESR), wherein the ESR is the sum of a dielectric loss plus an ohmic loss, wherein the ESR of the filter capacitor at an MRI RF pulsed frequency or range of frequencies is less than 2.0 ohms.

The filter capacitor may be selected from the group consisting of a monolithic ceramic capacitor, a flat-through capacitor, a chip capacitor and an X2Y attenuator.

A circuit board or substrate may be disposed on the device side, wherein the filter capacitor is mounted to the circuit board or substrate and the circuit board or substrate is located inside the conductive housing on the device side of the AIMD. The circuit board or substrate may be disposed adjacent and attached to either the ferrule and/or the insulator. Or, the circuit board or substrate may be disposed distant from and unattached to either the ferrule and/or the insulator.

The filter capacitor may be the first filter capacitor connected to the conductive pathway disposed on the device side. Said differently, there are no other filters capacitors or electronic circuits containing filter capacitors in the conductive pathway between and to the insulator hermetically sealing the ferrule opening and the filter capacitor. An inductor or inductance may be disposed between the filter capacitor and the at least one electrode of the implantable lead conductor.

A diode or back-to-back diodes may be connected at a first diode end to the conductive pathway and connected at a second diode end to either the ferrule and/or the conductive housing. Or a diode or back-to-back diodes may be connected in parallel with the filter capacitor to the conductive pathway and to either the ferrule and/or the conductive housing.

The filter capacitor may be a first capacitor element of a multielement broadband lowpass filter having at least one inductor, the multielement broadband lowpass filter forming one of the group consisting of a reverse L filter, an LL, a Pi and an n-element lowpass filter.

The at least two active electrode plates of the filter capacitor may be electrically connected to the conductive pathway devoid of any intermediate electronic circuits or filters disposed in series between the conductive pathway and the at least two active electrode plates.

The filter capacitor may be an element of a multielement broadband lowpass filter having at least one inductor, the multielement broadband lowpass filter forming one of the group consisting of an L filter, a reverse L filter, an LL, a reverse LL, a T, a Pi and an n-element lowpass filter.

A dielectric loss tangent measured in ohms at the MRI RF pulsed frequency or range of frequencies may be less than five percent of the filter capacitor's ESR. The filter capacitor may be a passive component lowpass filter.

The MRI RF pulsed frequency or range of frequencies may include 64 MHz or 128 MHz. The capacitance may be between 350 and 10,000 picofarads. The filter capacitor's ESR at the MRI RF pulsed frequency or range of frequencies may be less than 0.5 ohms or 0.1 ohms. The dielectric constant may be less than 1000, 200 or 90.

In other embodiments the at least two active and at least two ground electrode plates may also be at least five, ten, twenty, forty or more active and ground plates.

An insulative washer may be placed or located between the filter capacitor and then also either the insulator and/or ferrule.

Another embodiment of an active implantable medical device (AIMD) includes a conductive housing. The conductive housing defines a body fluid side outside the conductive housing and defines a device side inside the conductive housing. An electrically conductive ferrule is hermetically sealed to a housing opening in the conductive housing. The ferrule has a ferrule opening passing through the ferrule between the body fluid side and the device side. An insulator hermetically seals the ferrule opening. A conductive pathway hermetically seals and is disposed through the insulator between the body fluid side and the device side. The conductive pathway is in non-conductive relation with the ferrule. The conductive pathway on the body fluid side is connectable to an implantable lead conductor, wherein the implantable lead conductor has at least one electrode configured to be contactable to biological cells. A filter capacitor is disposed within the conductive housing on the device side. The filter capacitor includes a dielectric body supporting at least two active electrode plates interleaved with at least two ground electrode plates, wherein the at least two active electrode plates are electrically connected to the conductive pathway, and the at least two ground electrode plates are electrically coupled to either the ferrule and/or the conductive housing. The dielectric body has a dielectric constant less than 1000. A capacitance is between 10 and 20,000 picofarads. The filter capacitor is configured for EMI filtering of MRI high RF pulsed power by a low equivalent series resistance (ESR), wherein the ESR is the sum of a dielectric loss plus an ohmic loss, wherein the ESR of the filter capacitor at an MRI RF pulsed frequency or range of frequencies is less than 0.1 ohms, wherein the MRI RF pulsed frequency or range of frequencies comprises 64 MHz or 128 MHz. A dielectric loss tangent is measured in ohms at the MRI RF pulsed frequency or range of frequencies that is less than five percent of the filter capacitor's ESR. The filter capacitor is selected from the group consisting of a monolithic ceramic capacitor, a flat-through capacitor, a chip capacitor and an X2Y attenuator. A circuit board or substrate is disposed on the device side, wherein the filter capacitor is mounted to the circuit board or substrate and the circuit board or substrate is located inside the conductive housing on the device side of the AIMD. The filter capacitor is the first filter capacitor connected to the conductive pathway disposed on the device side. In other words, there are no other filters capacitors or electronic circuits containing filter capacitors in the conductive pathway between and to the insulator hermetically sealing the ferrule opening and the filter capacitor.

The circuit board or substrate may be disposed adjacent and attached to either the ferrule and/or the insulator or the circuit board or substrate may be disposed distant from and unattached to either the ferrule and/or the insulator.

The filter capacitor may be a first capacitor element of a multielement broadband lowpass filter having at least one inductor, the multielement broadband lowpass filter forming one of the group consisting of a reverse L filter, an LL, a Pi and an n-element lowpass filter.

A diode or back-to-back diodes may be connected at a first diode end to the conductive pathway and connected at a second diode end to either the ferrule and/or the conductive housing. A back-to-back diode or diodes may be connected in parallel with the filter capacitor to the conductive pathway and to either the ferrule and/or the conductive housing.

Another embodiment of an active implantable medical device system includes an implantable lead conductor having at least one electrode configured to be connectable to biological cells or tissue and an active implantable medical device (AIMD). The AIMD includes a conductive housing defining a body fluid side located outside the conductive housing and defining a device side located inside the conductive housing. An electrically conductive ferrule is hermetically sealed to a housing opening in the conductive housing, the ferrule having a ferrule opening passing through the ferrule between the body fluid side and the device side. An insulator hermetically seals the ferrule opening. A conductive pathway hermetically seals and is disposed through the insulator between the body fluid side and the device side, where the conductive pathway in non-conductive relation with the ferrule, and wherein a distal end of the conductive pathway is detachably connected to a proximal end of the implantable lead conductor. A filter capacitor is disposed within the conductive housing on the device side. The filter capacitor includes: a capacitance of between 10 and 20,000 picofarads; a dielectric body supporting at least two active electrode plates interleaved with at least two ground electrode plates, wherein the at least two active electrode plates are electrically connected to the conductive pathway on the device side, and the at least two ground electrode plates are electrically coupled to either the ferrule and/or the conductive housing; wherein the dielectric body comprises a dielectric constant less than 1000; and wherein the filter capacitor is configured for EMI filtering of MRI high RF pulsed power by a low equivalent series resistance (ESR), wherein the ESR is the sum of a dielectric loss plus an ohmic loss, wherein the ESR of the filter capacitor at an MRI RF pulsed frequency or range of frequencies is less than 2.0 ohms.

Another embodiment of an active implantable medical device (AIMD), includes: a conductive housing defining a body fluid side located outside the conductive housing and defining a device side located inside the conductive housing; an electrically conductive ferrule hermetically sealed to a housing opening in the conductive housing, the ferrule having a ferrule opening passing through the ferrule between the body fluid side and the device side; an insulator hermetically sealing the ferrule opening; a conductive pathway hermetically sealed and disposed through the insulator between the body fluid side and the device side, where the conductive pathway in non-conductive relation with the ferrule, and the conductive pathway on the body fluid side connectable to an implantable lead conductor having at least one electrode; a primary filter capacitor disposed within the conductive housing on the device side adjacent to the insulator, the primary filter capacitor being a feedthrough filter, wherein the primary filter capacitor is a first filter capacitor connected to the conductive pathway disposed on the device side; a secondary filter capacitor disposed within the conductive housing on the device side, wherein the secondary filter capacitor is selected from the group consisting of a monolithic ceramic capacitor, a flat-through capacitor, a chip capacitor and an X2Y attenuator. Both the primary and secondary filter capacitors each include: a capacitance of between 10 and 20,000 picofarads; a dielectric body supporting at least two active electrode plates interleaved with at least two ground electrode plates, wherein the at least two active electrode plates are electrically connected to the conductive pathway on the device side, and the at least two ground electrode plates are electrically coupled to either the ferrule and/or the conductive housing; wherein the dielectric body comprises a dielectric constant less than 1000; wherein the filter capacitors are configured for EMI filtering of MRI high RF pulsed power by a low equivalent series resistance (ESR), wherein the ESR is the sum of a dielectric loss plus an ohmic loss, wherein the ESR of the filter capacitor at an MRI RF pulsed frequency or range of frequencies is less than 2.0 ohms. A circuit board or substrate is located inside the conductive housing on the device side of the AIMD, wherein the secondary filter capacitor is mounted to the circuit board or substrate.

An embodiment of a circuit board assembly includes: a circuit board substrate configured to be installable inside a conductive housing of an active implantable medical device (AIMD), where the AIMD would include: a conductive housing defining a body fluid side located outside the conductive housing and defining a device side located inside the conductive housing; an electrically conductive ferrule hermetically sealed to a housing opening in the conductive housing, the ferrule having a ferrule opening passing through the ferrule between the body fluid side and the device side; an insulator hermetically sealing the ferrule opening; and a conductive pathway hermetically sealed and disposed through the insulator between the body fluid side and the device side, the conductive pathway in non-conductive relation with the ferrule, and the conductive pathway on the body fluid side connectable to an implantable lead conductor having at least one electrode. A multitude of electronic components are disposed onto the circuit board substrate, the multitude of electronic components configured to control either sensing and/or pacing pulses transmitted through the connectable implanted lead conductor. A filter capacitor is disposed onto the circuit board substrate. The filter capacitor includes: a capacitance of between 10 and 20,000 picofarads; and a dielectric body supporting at least two active electrode plates interleaved with at least two ground electrode plates; wherein the at least two active electrode plates are configured to be electrically connectable to the conductive pathway on the device side; wherein the at least two ground electrode plates are configured to be electrically connectable to either the ferrule and/or the conductive housing; wherein the dielectric body comprises a dielectric constant less than 1000; and wherein the filter capacitor is configured for EMI filtering of MRI high RF pulsed power by a low equivalent series resistance (ESR), wherein the ESR is the sum of a dielectric loss plus an ohmic loss, wherein the ESR of the filter capacitor at an MRI RF pulsed frequency or range of frequencies is less than 2.0 ohms.

An embodiment of feedthrough assembly can be configured to be connectable to a conductive housing of an active implantable medical device (AIMD), the feedthrough assembly includes: an electrically conductive ferrule configured to be hermetically sealable to a housing opening in the conductive housing, the ferrule having a ferrule opening passing through the ferrule, wherein the ferrule defines a first side opposite a second side about the ferrule opening; an insulator hermetically sealing the ferrule opening; a conductive pathway hermetically sealed and disposed through the insulator between the first side and the second side, the conductive pathway in non-conductive relation with the ferrule, wherein the conductive pathway on the first side is configured to be connectable to an implantable lead conductor having at least one electrode; and a filter capacitor disposed on the second side of the ferrule. The filter capacitor includes: a capacitance of between 10 and 20,000 picofarads; a dielectric body supporting at least two active electrode plates interleaved with at least two ground electrode plates, wherein the at least two active electrode plates are electrically connected to the conductive pathway on the second side, and the at least two ground electrode plates are electrically coupled to the ferrule; wherein the dielectric body comprises a dielectric constant less than 1000; and wherein the filter capacitor is configured for EMI filtering of MRI high RF pulsed power by a low equivalent series resistance (ESR), wherein the ESR is the sum of a dielectric loss plus an ohmic loss, wherein the ESR of the filter capacitor at an MRI RF pulsed frequency or range of frequencies is less than 2.0 ohms.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 20 illustrates a cross-sectional view of an MLCC capacitor mounted to separate circuit traces;

FIG. 21 is a schematic representation explaining the elements that are components of the FIG. 20 capacitor's equivalent series resistance (ESR);

FIG. 22 is an equation that relates the capacitance with the capacitor's active area, dielectric constant, number of electrode plates and dielectric thickness;

FIG. 29 illustrates the reactance and real losses of a 2000 picofarad X7R feedthrough capacitor;

FIG. 30 illustrates the reactance and real losses of a 2000 picofarad COG (NPO) capacitor;

FIG. 66 is similar in outline to the flat-through capacitor of FIG. 17;

FIG. 67 shows the internal active electrode plates of FIG. 66 now with the dielectric removed;

FIG. 68 shows the internal ground electrode plates of FIG. 66 now with the dielectric removed;

FIG. 69 shows how the active and ground electrode plates of FIG. 66 nest parallel to one another with the dielectric removed.

DETAILED DESCRIPTION OF THE PREFERRED EMBODIMENTS

Figure 1:
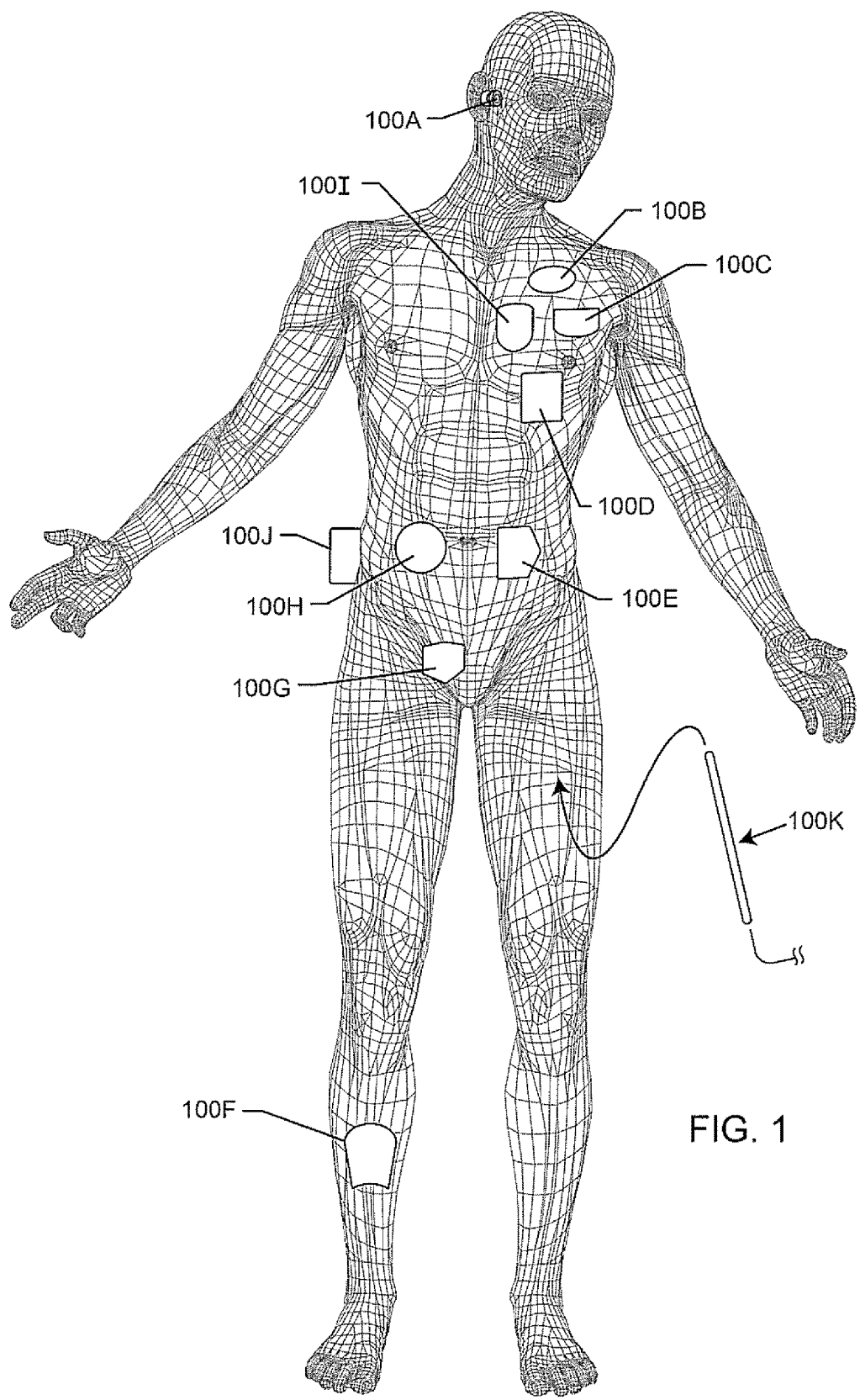
FIG. 1 is a wire-formed diagram of a generic human body showing a number of exemplary implanted medical devices.

FIG. 1 illustrates various types of active implantable medical devices referred to generally by the reference numeral 100 that are currently in use. FIG. 1 is a wire formed diagram of a generic human body showing a number of exemplary implanted medical devices. Numerical designation 100A is a family of implantable hearing devices which can include the group of cochlear implants, piezoelectric sound bridge transducers and the like. Numerical designation 1008 includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. Numerical designation 100C shows a cardiac pacemaker which is well-known in the art. Numerical designation 100D includes the family of left ventricular assist devices (LVAD's), and artificial hearts, including the recently introduced artificial heart known as the Abiocor. Numerical designation 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of implantable bone growth stimulators for rapid healing of fractures. Numerical designation 100G includes urinary incontinence devices. Numerical designation 100H includes the family of pain relief spinal cord stimulators and anti-tremor stimulators. Numerical designation 100H also includes an entire family of other types of neurostimulators used to block pain. Numerical designation 100I includes a family of implantable cardioverter defibrillator (ICD) devices and also includes the family of congestive heart failure devices (CHF). This is also known in the art as cardio resynchronization therapy devices, otherwise known as CRT devices. Numerical designation 100J illustrates an externally worn pack. This pack could be an external insulin pump, an external drug pump, an external neurostimulator or even a ventricular assist device. 100K illustrates the insertion of an external probe or catheter. These probes can be inserted into the femoral artery, for example, or in any other number of locations in the human body.

Referring to U.S. 2003/0050557, Paragraphs 79 through 82, the contents of which are incorporated herein, metallic structures, particularly leads, are described that when placed in MRI scanners, can pick up high electrical fields which results in local tissue heating. This heating tends to be most concentrated at the ends of the electrical structure (either at the proximal or distal lead ends). This safety issue can be addressed using the disclosed systems and methods of the present invention. A significant concern is that the distal electrodes, which are in contact with body tissue, can cause local tissue burns.

As defined herein, an active implantable medical device (AIMD) includes any device or system that is designed to be implanted within a human body either totally or partially and includes at least one electronic circuitry. AIMDs may have primary or secondary batteries as their energy sources. AIMDs may also harvest energy from the body either through mechanical motion or through chemical or through biochemical battery cell type effects. An AIMD may also contain a resonant circuit whereby it captures energy from external pulsing electromagnetic field. An example of this would be what is known in the industry as the Bion©. In general, AIMDs are connected to either a leadwire or are directly connected to electrodes without a leadwire wherein, these electrodes are contactable to biological cells. AIMD electrodes may be used for therapy delivery, sensing of biological signals or both. AIMDs may also be integrated with fiber optic cables and receive their power or signals optically wherein there is an optical converter which may convert the optical signals to either digital signals or to power.

A subclass of AIMDs is known as cardiac implantable electronic devices (CIEDs). CIEDs include all types of pacemakers, implantable cardioverter defibrillators, implantable loop recorders, subcutaneous ICDs and the like. Another subclass of AIMDs includes all types of neurostimulators, including, but not limited to spinal cord stimulators, deep brain stimulators, urinary incontinence stimulators and the like. An AIMD may include an external component, such as an RF transmitter, an RF telemetry device or even a worn wrist watch, which sends signals to an implanted device and its associated electrodes. In other words, the AIMD, as defined herein can have externally worn components in addition to implanted components.

In general, an AIMD usually has a housing which hermetically shields and protects one or more internal electronic circuits. As defined herein, the AIMD has a body fluid side, which is defined as anything on the exterior of the AIMD housing. It also has a device side. The device side, which can also be known as an inboard side, refers to the interior of the AIMD housing and any components or electronic circuits that may be disclosed within it.

As used herein, the lead means an implanted lead, including its conductors and electrodes that have electrodes that are in contact with body tissue. In general, for an AIMD, the term lead means the lead that is outside of the AIMD housing and is implanted or directed into body tissues. The term leadwire as used herein refers to the wiring or circuit traces that are generally inside of the active implantable medical device (AIMD) and are not exposed directly to body fluids.

Figure 2:
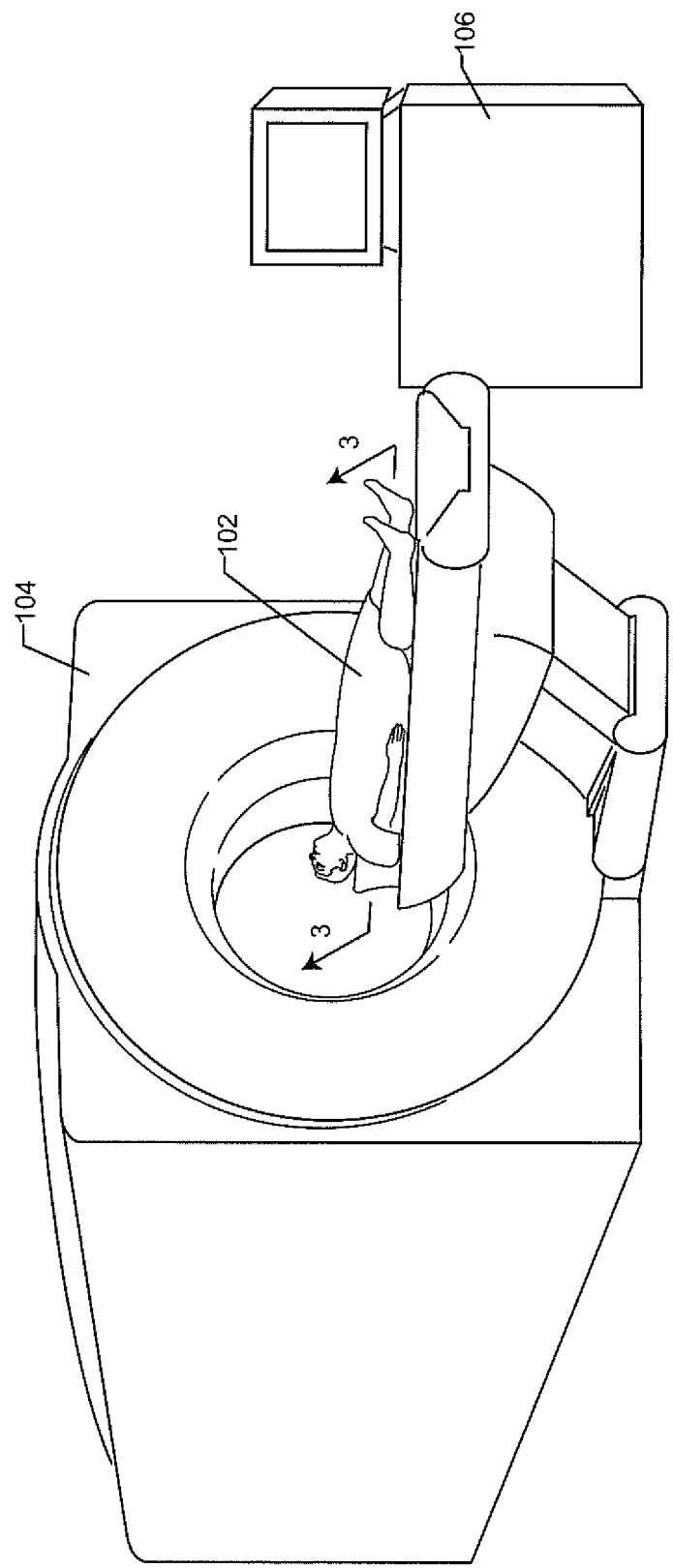
FIG. 2 is a pictorial view of an AIMD patient who is about to be placed into an MRI scanner.

FIG. 2 illustrates an AIMD patient 102 about to be conveyored into an MRI machine 104. Imaging processing equipment is shown as 106.

Figure 3:
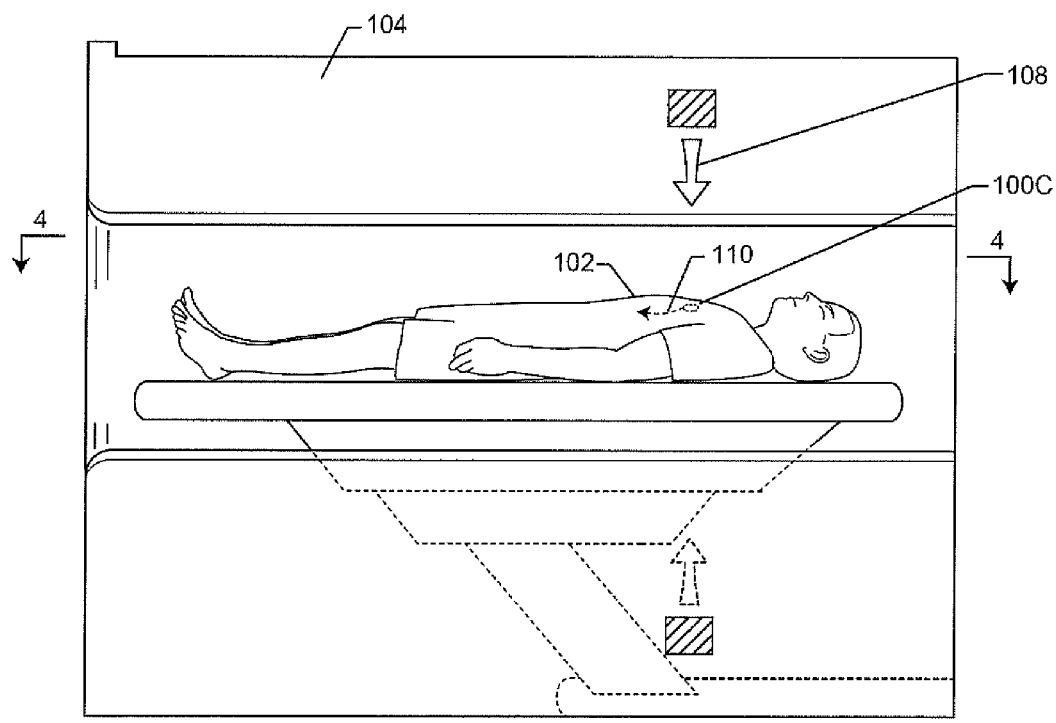
FIG. 3 shows a side view of the patient within the scanner showing an intense RF field impinging on the implanted medical device and its associated lead.

FIG. 3 is a side view showing the patient 102 within the MRI scanner bore 104. Intense RF field 108 is generated by the scanners bird cage coil. As can be seen, this RF field is impinging on both the implanted cardiac pacemaker 100C and its associated leads 110.

Figure 4:
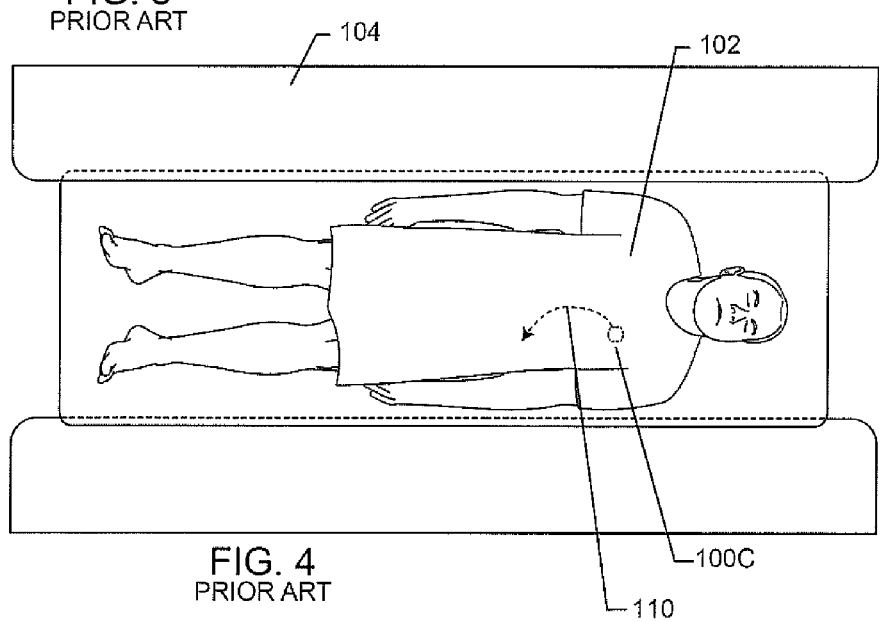
FIG. 4 is a top view of the patient in the MRI scanner showing one location of the AIMD and its associated lead.

FIG. 4 is a top view of the patient 102 inside the MRI scanner bore 104. As can be seen, the pacemaker 100C is in a left pectoral pocket with the leads 110 routed transvenously down into the interior chambers of the heart.

Figure 5:
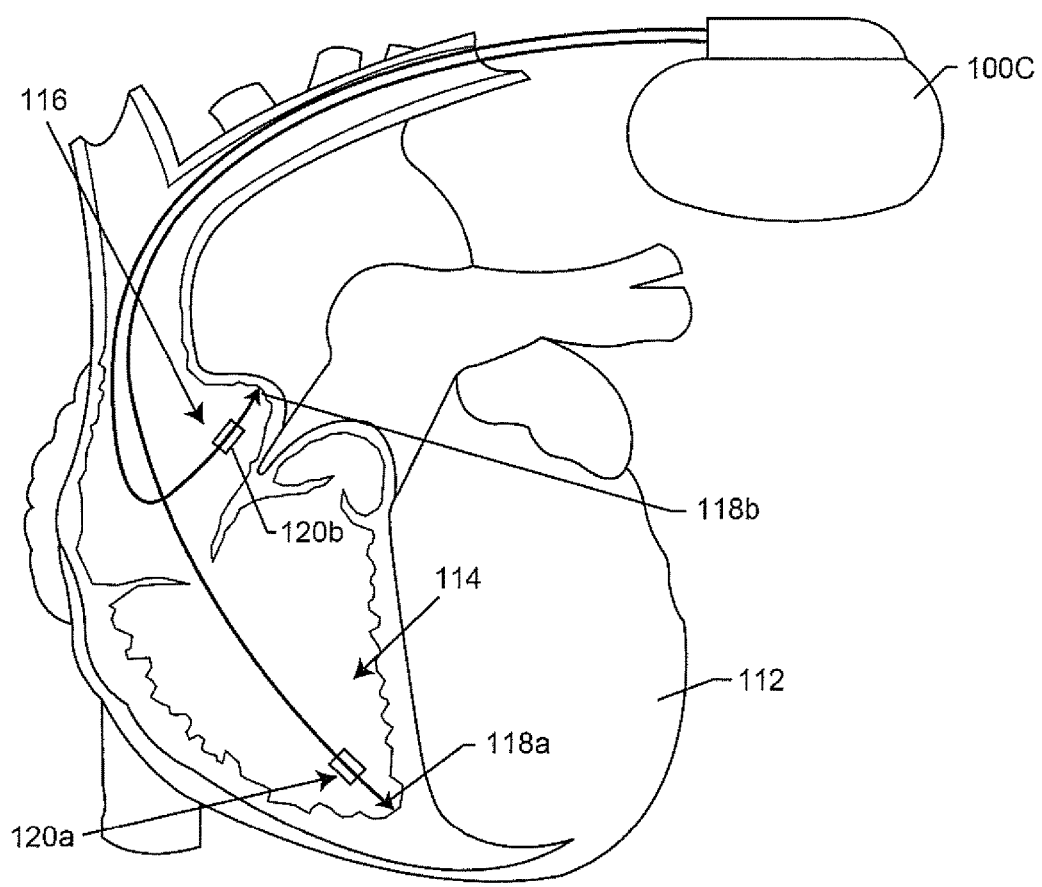
FIG. 5 is a line drawing of a human heart with cardiac pacemaker dual chamber bipolar leads shown in the right ventricle and the right atrium.

FIG. 5 is a line drawing of a human heart 112 with cardiac pacemaker 100C dual chamber bipolar leads shown in the right ventricle 114 and the right atrium 116 of a human heart 112.

Figure 6:
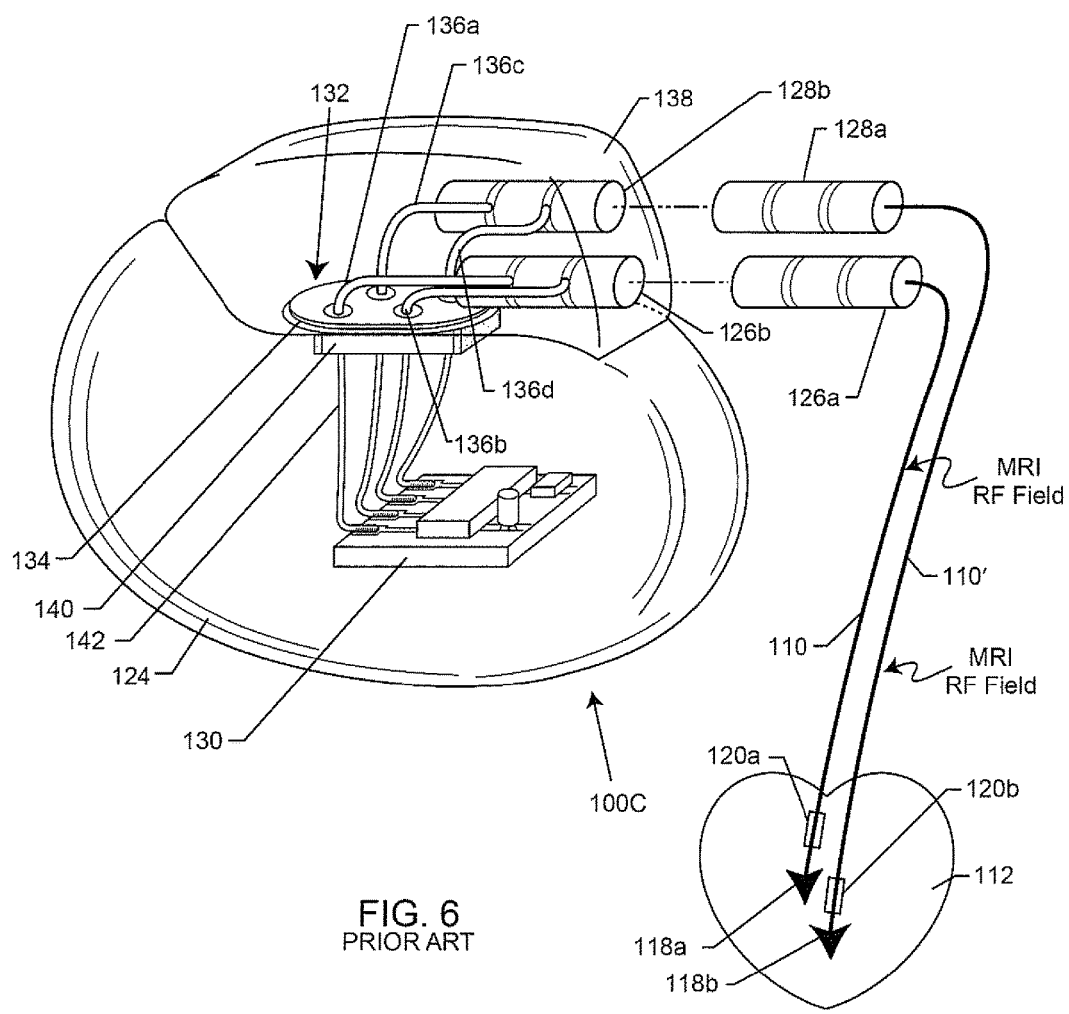
FIG. 6 illustrates a dual chamber cardiac pacemaker with its associated leads and electrodes implanted into a human heart.

Referring once again to FIG. 5, as previously mentioned, it is very important that this lead system does not overheat during MRI procedures particularly at or near the distal tip 118a, 118b electrodes and ring electrodes 120a, 120b. If either or both the distal tip 118a, 118b and ring 120a, 120b electrode become overgrown by body tissue, excessive overheating can cause scarring, burning or necrosis of said tissues. This can result in loss of capture (loss pacing pulses) which can be life-threatening for a pacemaker dependent patient. FIG. 6 is a pectoral view of a prior art cardiac pacemaker 100C showing dual chamber bipolar leads 110, 110' routed to distal tip electrodes 118a and 118b and distal ring electrode 120a and 120b. As can be seen, the leads 110, 110' are exposed to a powerful RF-pulsed field from an MRI machine. This induces electromagnetic energy on the leads which are coupled via ISO Standard IS-1 or DF-1 connectors 126, 128 through header block 138 which connects the leads to electronic circuits 130 inside of the hermetically sealed pacemaker housing 124. A hermetic seal assembly 132 is shown with a metal ferrule 134 which is generally laser welded into the titanium housing 124 of the cardiac pacemaker 100C. Lead wires 136a through 136d penetrate the ferrule 134 of the hermetic seal in non-conductive relation. Glass seals or gold brazed alumina insulators are formed to perfect the hermetic seal which keeps body fluids from getting to the inside of the pacemaker housing 124.

Figure 7:
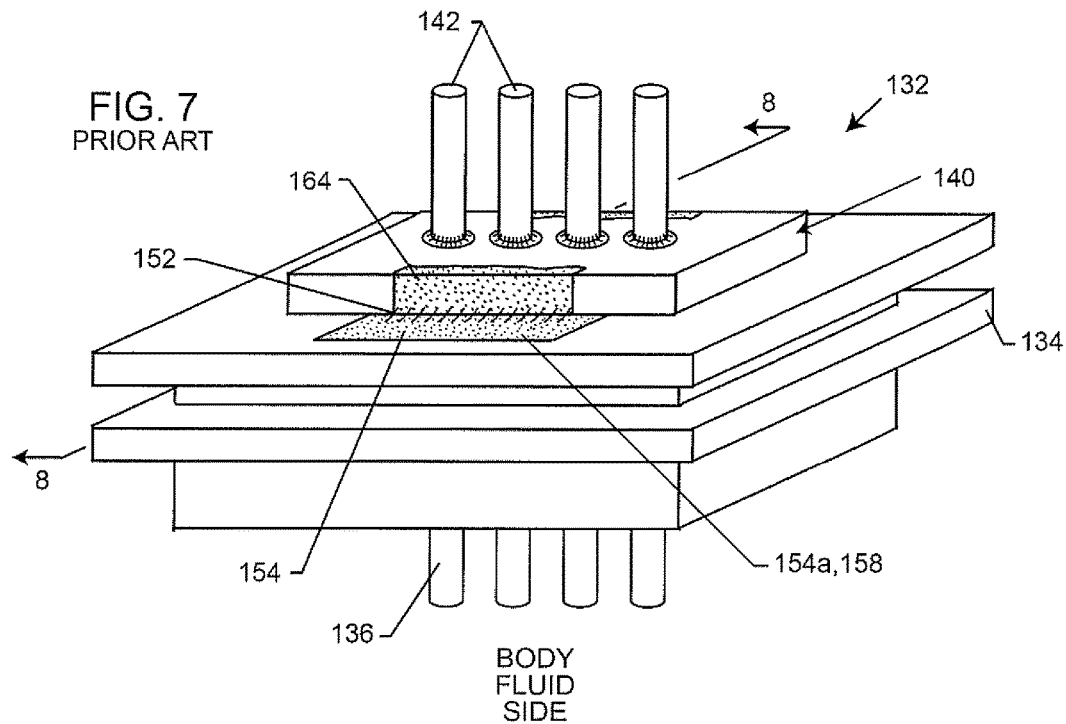
FIG. 7 is a perspective view illustrating the rectangular feedthrough capacitor mounted to a hermetic terminal.
Figure 8:
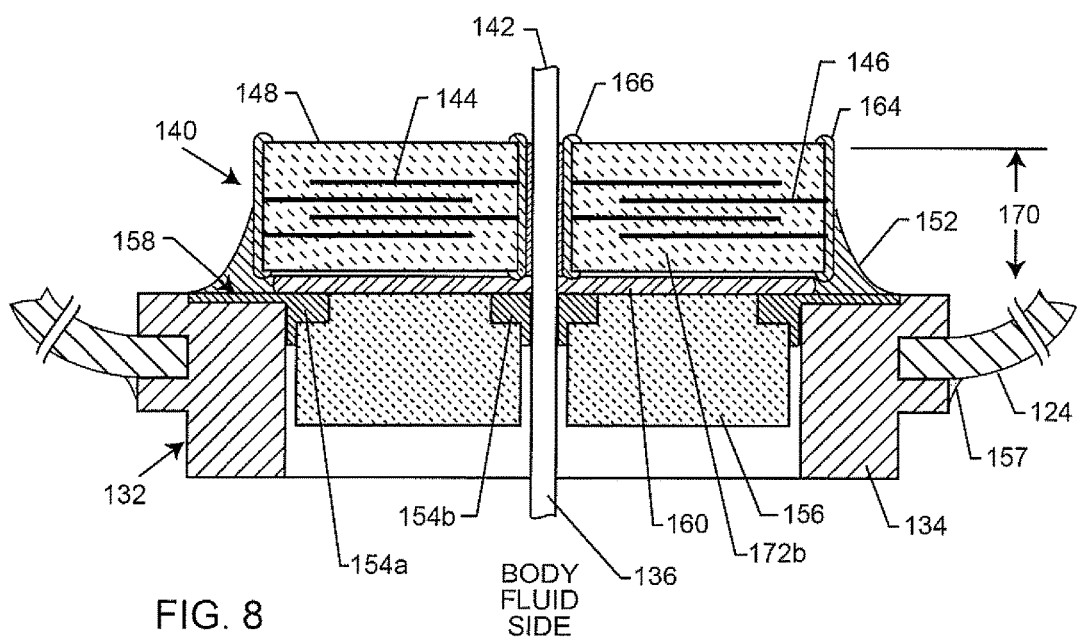
FIG. 8 is an enlarged sectional view taken generally along the line 8-8 of FIG. 7.

FIGS. 7-8 illustrate a prior art rectangular quadpolar feedthrough capacitor (planar array) 140 mounted to the hermetic terminal 132 of a cardiac pacemaker in accordance with U.S. Pat. No. 5,333,095 to Stevenson et al. the contents of which are incorporated herein. Referring back to FIG. 6, one can see that the capacitor 140 is mounted adjacent to the ferrule 132 or the insulator 156. As illustrated in FIGS. 7-8, in a typical broadband or lowpass EMI filter construction, a ceramic feedthrough filter capacitor 140 is used in a hermetic feedthrough assembly 132 to suppress and decouple undesired interference or noise transmission along one or more terminal pins 142, and may comprise a capacitor having two sets of electrode plates 144 and 146 embedded in spaced relation within an insulative dielectric substrate or base 148, formed typically as a ceramic monolithic structure. One set of the electrode plates 144 is electrically connected at an inner diameter cylindrical surface to metallization 166 of the capacitor structure 140 to the conductive terminal pins 142 utilized to pass the desired electrical signal or signals (see FIG. 11). The other or second set of electrode plates 146 is coupled to metallization 164 at a sidewall of the dielectric providing an outer edge surface of the capacitor 140 through metallization to a rectangular ferrule 134 of conductive material. In the prior art, without regard to high frequency capacitor ESR, the number and dielectric thickness spacing of the electrode plate sets 144, 146 varies in accordance with the capacitance value and the voltage rating of the capacitor 140.

In operation, the coaxial capacitor 140 permits passage of relatively low frequency electrical signals along the terminal pins 142, while shielding and decoupling/attenuating undesired interference signals of typically high frequency to the conductive housing 124. Feedthrough capacitors 140 of this general type are available in unipolar (one), bipolar (two), tripolar (three), quadpolar (four), pentapolar (five), hexpolar (6) and additional lead configurations. Feedthrough capacitors 140 (in both discoidal and rectangular configurations) of this general type are commonly employed in implantable cardiac pacemakers and defibrillators and the like, wherein the pacemaker housing is constructed from a biocompatible metal such as titanium alloy, which is electrically and mechanically coupled to the hermetic terminal pin assembly which is in turn electrically coupled to the coaxial feedthrough filter capacitor 140. As a result, the filter capacitor and terminal pin assembly prevent entrance of interference signals to the interior of the pacemaker housing 124, wherein such interference signals could otherwise adversely affect the desired cardiac pacing or defibrillation function.

As one can see in FIG. 7, the conductive polyimide material 152 connects between the capacitor metallization 164 and the gold braze area 154. The gold braze 154 forms a metallurgical bond with the titanium and precludes any possibility of an unstable oxide forming. Gold is a noble metal that does not oxidize and remains very stable even at elevated temperatures. The novel construction methodology illustrated in FIG. 7 guarantees that the capacitor ohmic losses will remain very small at all frequencies. By connecting the capacitor's electrode plates to a low resistivity surface such as gold, one is guaranteed that this connection will not substantially contribute to the capacitor's overall ESR. Keeping the ESR as low as possible is very important for diverting a high amount of RF current such as that induced in the lead system by MRI scanners. One is referred to U.S. Pat. No. 6,765,779 to Stevenson et al., for additional information on electrically connecting to non-oxidized surfaces, the contents of which are incorporated herein by reference.

FIG. 8 is a cross-section of the capacitor shown in FIG. 7. One can see that the gold braze (or weld) areas 154a and 154b that form the hermetic seal between the alumina insulator 156 and the titanium ferrule 134 are desirably on the feedthrough capacitor side. This makes it easy to manufacture the gold bond pad area 158 for convenient attachment of the conductive thermal-setting material 152. In other words, by having the gold braze hermetic seals 154 on the same side as the gold bond pad area 158, these can be co-formed in one manufacturing operation in a gold braze vacuum furnace. Further, a unique insulative material 160 is disposed between the capacitor 140 and the underlying hermetic terminal 132.

Figure 9:
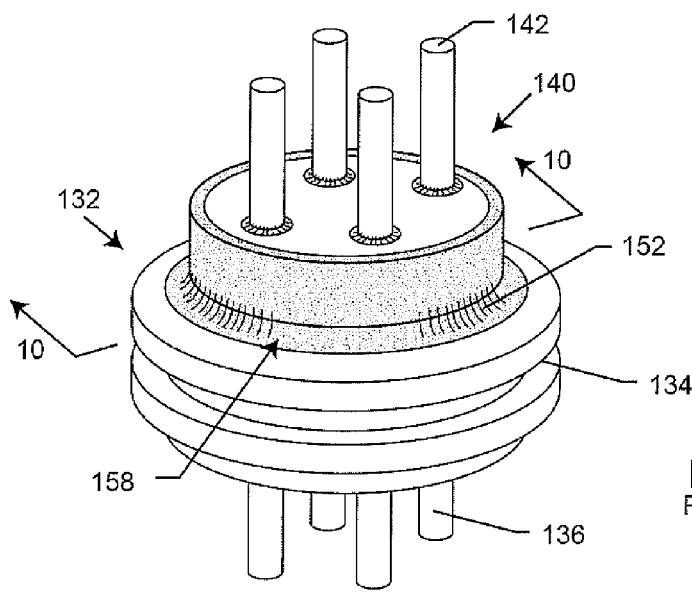
FIG. 9 is a perspective view of a round hermetic terminal showing a quadpolar RF diverter feedthrough capacitor.

FIG. 9 is a quad polar feedthrough capacitor 140 mounted to a hermetic terminal 132 similar to that described in FIG. 7 except that in this case, the structure is round or discoidal.

Figure 10:
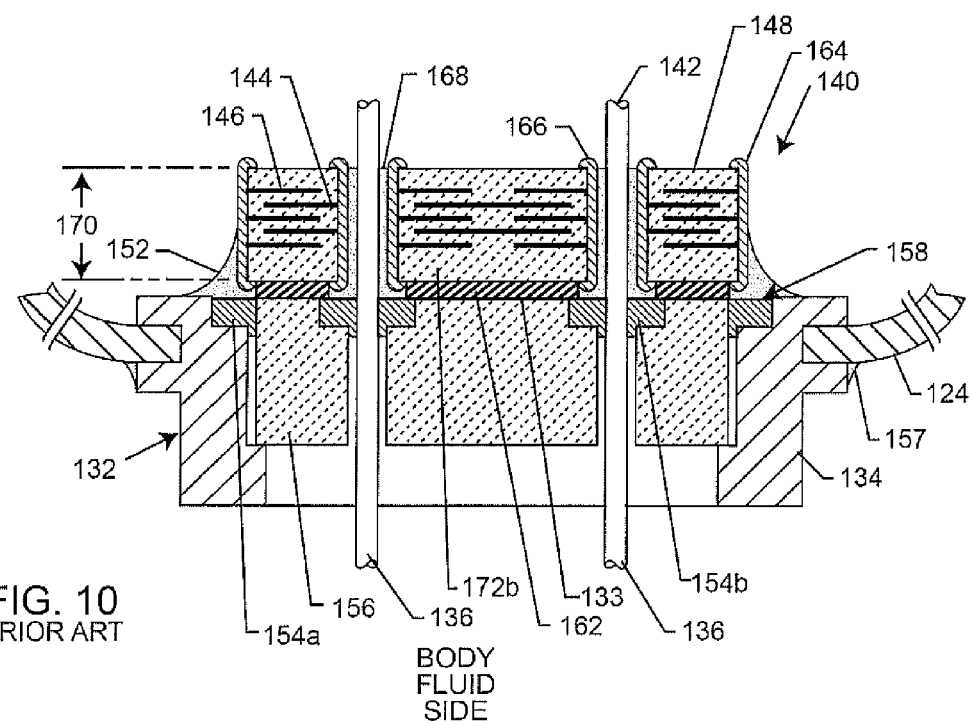
FIG. 10 is an enlarged cross-sectional view taken generally along the line 10-10 from FIG. 9.

FIG. 10 is a cross-sectional view taken generally from section 10-10 from FIG. 9. There are four feedthrough leadwires 142 which extend through the capacitor 140, which has a ground electrode plate set 146 and an active electrode plate set 144.

As shown there are only two active electrodes 144 and three ground electrodes 146. This low electrode plate count results in a feedthrough diverter capacitor 140 that has a relatively high ESR at high frequencies. In a recent experiment conducted by the inventors, a typical EIA X7R 400 picofarad feedthrough capacitor with only four electrode plates had an ESR at 64 MHz of 4.8 Ohms. Re-design of the same geometry (size) capacitor with an EIA NPO dielectric for a 400 picofarad capacitor with over 20 electrodes resulted in an ESR at 64 MHz of approximately 300 milliohms (0.3 Ohms). This sixteen to one reduction in 64 MHz is a dramatic illustration of the importance of designing the AIMD MRI diverter capacitor 140 for low ESR. For example, for an X7R capacitor the impedance would be the square root of the sum of the capacitor's reactance squared plus the ESR squared. A 400 pF capacitor has a reactance of 2.49 Ohms at 64 MHz. This results in a capacitor impedance Z which is equal to −j2.49+4.8 or approximately 5.41 Ohms. Assuming an MRI induced RF voltage at the AIMD input at 64 MHz of 10 Volts, the RF current diverted through the X7R capacitor is 10 Volts divided by 5.41 Ohms which is 1.85 Amps. The power dissipation due to the X7R capacitor's ESR ($I^2R$) is $(1.85)^2(4.8)$=16.43 Watts. This amount of power dissipation is very excessive for such a small component and will cause a temperature rise of over 20 degrees C. On the other hand, a 400 pF NPO capacitor's impedance is equal to −j2.49+0.3 or Z=2.51 Ohms. This lower impedance will result in a much better filter (higher attenuation) and will drop the RF voltage from 10 Volts to approximately 3.71 Volts. This voltage drop is caused by the lead's characteristic impedance and the fact that more current has been drawn through this impedance. This causes a voltage drop in the lead's characteristic impedance as measured at the input to the AIMD. The RF current through the NPO capacitor is then 3.71 Volts divided by Z of 2.51 Ohms which is 1.48-amps. The power dissipation ($I^2R$) is $(1.48 \text{ Amps})^2(0.3 \text{ Ohm})$ which equals 0.66 Watts which will result in a much smaller temperature rise. Accordingly, the low ESR diverter capacitor 210, 410 design of the present invention offers the following advantages: (1) it has a much lower impedance at 64 MHz and is therefore a more effective EMI filter, and; (2) because it offers higher attenuation, it therefore acts to reduce the MRI induced RF voltage at the input to the AIMD; and (3) as will be shown in the present invention, the diverter capacitor 210, 410 can be designed to conduct or convect heat away and dissipate it over a larger surface area. (Note that the above example corrects the parent application's typographical and numerical errors.)

The above examples of ESR and impedance are just illustrated examples of many thousands of possibilities. For active implantable medical devices, in general, capacitance values range anywhere from 300 pF to 15,000 pF. Each design has a different physical geometry in size and internal electrode plates. In other words, there are many other examples that would have different values of ESR. However, the general principles illustrated above do apply across the board. Lower k dielectrics will always mean a higher number of electrode plates and hence, a lower ESR. That means that the low ESR designs will have much less heating of the capacitor itself in an MRI environment.

The capacitor 140 is bonded with an insulating washer 162 to the hermetic terminal 132. An electrical attachment 152 is made using a thermal-setting conductive adhesive between the feedthrough capacitor outside diameter metallization 164 and gold braze surface 158. The necessity to make an oxide free attachment between the feedthrough capacitor 140 and the ferrule 134 is described in U.S. Pat. No. 6,765,779. An insulator 156 such as glass compression, glass fusion seal or alumina ceramic is hermetically sealed to the ferrule 134 by means of gold braze 154a. The four leadwires 142 are also hermetically sealed to the insulator 156 via gold braze rings 154b (there are four of these). The feedthrough capacitor active electrode plates 144 are attached by co-firing to the capacitor feedthrough hole inside diameter metallization 166. Conductive electrical material 168 is used to attach the metallization 166 to each one of the leadwires 142.

Referring once again to FIG. 8, one can see that there are only two active electrode plates 144 and two ground electrode plates 146. A low electrode plate count is typically the case for prior art filtered feedthrough (diverter) capacitors 140 used in AIMD applications such as cardiac pacemakers, ICDs and the like. Another reason that the capacitance value is generally low is that a high capacitance value would load down the output of the AIMD. For example, too high of a capacitance value would distort pacemaker therapeutic pulses and also rob energy from the system. An even more extreme example would be the case of an implantable cardioverter defibrillator, wherein too high of a filter capacitance value would seriously degrade the high voltage monophasic or biphasic shock wave form. In the experience of the inventors, the capacitance value for AIMD diverter capacitor 140 is in a relatively narrow range from 10 to 20,000 picofarads. In most cases, the capacitance value is between 350 and 10,000 picofarads. Having a capacitance value between 350 and 10,000 picofarads effectively attenuates most emitters from which AIMDs can be affected. This includes microwave ovens, cellular telephones and the like, which typically operate in the GHz frequency range. The thickness 170 of the capacitor however, cannot be below a certain minimum or the barium titanate based ceramic capacitor 148 will become too fragile. The entire hermetic terminal 132 and the feedthrough capacitor 140 must be able to withstand thermal cycles and shocks including installation by laser welding 157 into the AIMD housing 124. Accordingly, it is very unusual to see a diverter capacitor 140 thickness 170 of less than 20/1000 of an inch (0.020 inches or 20 mils). Correspondingly, when one looks at a typical prior art feedthrough capacitor 140 for human implant in cross-section, one sees that there are very few electrodes 144, 146 relative to its overall thickness 170. In fact, there are usually a number of blank dielectric (no electrodes) cover sheets/layers 172 added on the top and/or bottom of the capacitor 140 consisting of ceramic material which is co-fired to add mechanical strength. However, there is a serious downside to having very few electrode plates 144, 146, and that is that the high frequency equivalent series resistance (ESR) of the capacitor increases. For prior art AIMD filter or diverter capacitor 140 having significant dielectric and/or ohmic resistance at high frequencies simply does not matter. This is because the power induced from a typical emitter, such as a cellular telephone or microwave oven results in a trivial amount of RF current flowing through diverter capacitor 140. Even in the most extreme examples, only a few milliwatts of heat would be generated within the capacitor structure itself. However, for high power RF current handling applications, such as diverting MRI induced RF energy, the capacitor dielectric loss and high frequency ESR become critical and must be kept as low as possible. Accordingly, it is a feature of the present invention to have a relatively high number of electrode plates 144, 146 (generally greater than 10). However, with a high k barium titanate based ceramic dielectric with a dielectric constant of around 2500, a high number of electrode plates would result in a very high (too high) capacitance value. A way to solve this is to use a relatively low dielectric constant material, such as EIA Standard NPO material. NPO material has a much lower k (generally, in the area of 60 to 90). Accordingly, in order to achieve the desired capacitance value (in the range of 350 to 10,000 picofarads), a much greater number of electrode plates is required. The higher number of electrode plates creates more parallel paths for RF current flow and greatly reduces the ESR of the feedthrough capacitor. One is referred to the equation illustrated in FIG. 22 to explain the relationship between capacitance and the number of electrode plates and other factors.

Figure 11:
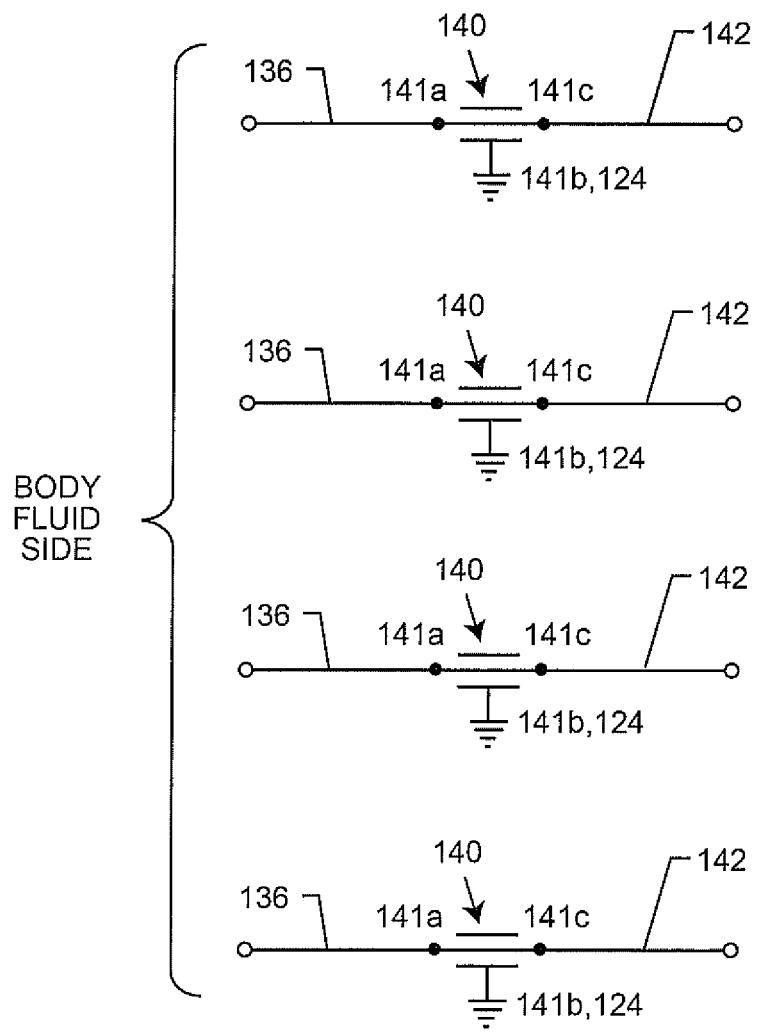
FIG. 11 is an electrical schematic diagram of the quadpolar feedthrough capacitor of FIGS. 7-10.

FIG. 11 is a schematic diagram of the quad polar feedthrough capacitor 140 of FIGS. 7-10. Feedthrough capacitors are three-terminal devices labeled in FIG. 1 as 141*a*, 141*b*, and 141*c*.

Figure 12:
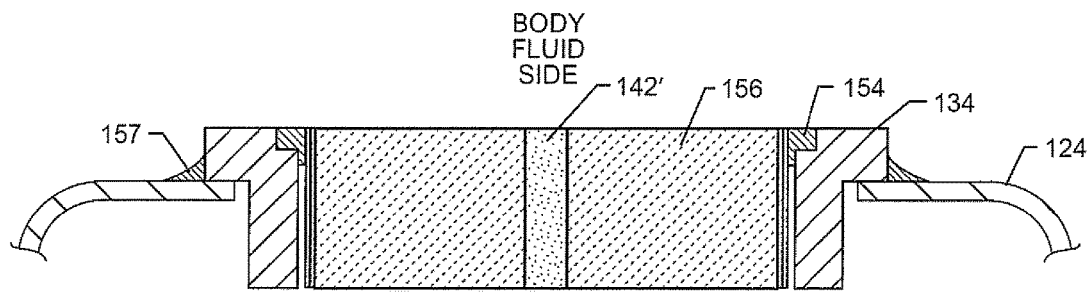
FIG. 12 is a sectional view of an embodiment of a novel hermetic terminal subassembly installed in a housing of an AIMD.

FIG. 12 is a sectional view of an embodiment of a novel hermetic terminal subassembly installed in a housing of an AIMD taken from U.S. Pat. No. 8,653,384 as FIG. 17, the contents of which are incorporated herein with this reference. The outside diameter of the alumina hermetic insulator 156 has metalized surfaces, which are adhesion and wetting surfaces so that gold braze 154 can be melted and hermetically bonded to the alumina hermetic insulator 156 and the ferrule 134 of the hermetic terminal assembly. The ferrule 134 may be installed into the AIMD housing 124 by laser welding 157, or the like. In this embodiment it is a goal to eliminate the highly expensive biocompatible and noble leadwires 142, as previously illustrated. Instead of a feedthrough leadwire 142, this embodiment comprises a pure platinum filled via hole 142'. It is a novel feature of this embodiment that this via hole material 142' be of essentially pure platinum that is co-fired with the essentially high purity alumina ceramic substrate 156.

In general, AIMD hermetic seals have a body fluid side and a device side. In general, the device side (inboard side) is located inside the conductive housing of the AIMD. For example, for a hermetic seal it would have conductive passages or leadwires passing through it. The conductive passages or leadwires would be exposed to body fluid on the body fluid side and on the inboard side or device side, they would be located inside of the AIMD housing and the leads or conductive pathways would be connectable to AIMD internal electronic circuits. As can be seen, the conductive pathway through the insulator 156 between the body fluid side and the device side can be made from a conductive wire 142 or now as a conductive paste 142'. The conductive pathway between the body fluid side and the device side can also be a combination of conductive inserts into conductive pastes and the like.

Figure 13:
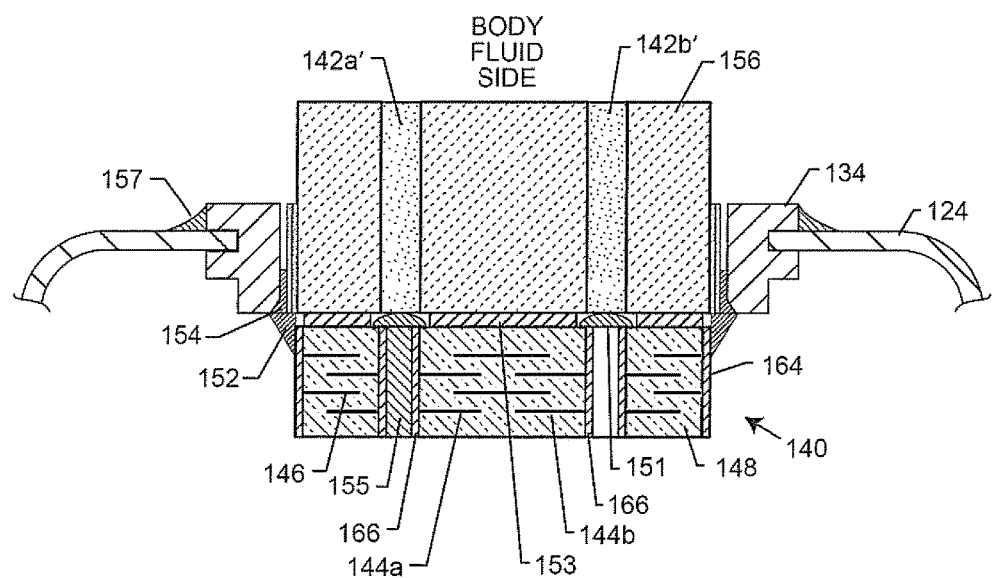
FIG. 13 is a sectional view of another embodiment of a hermetic terminal subassembly now showing a capacitor with a filled and a bore-coated via.

FIG. 13 is a sectional view of another embodiment of a hermetic terminal subassembly now showing a capacitor with a filled and a bore-coated via also taken from U.S. Pat. No. 8,653,384 as FIG. 22. One is directed to U.S. Pat. No. 8,179,658, which is incorporated herein by this reference, which shows a capacitor via within internal metallization 166 electrically connected to a solid feedthrough leadwire. In the present embodiment, the feedthrough capacitor 140 has been mounted directly to the surface of the co-fired high purity alumina hermetic terminal subassembly with one or more pure platinum filled vias 142*a*' and 142*b*'. The feedthrough capacitor 140 is first placed on the bottom surface of the co-fired high purity alumina hermetic terminal subassembly with one or more pure platinum (or equivalent) filled vias. In this embodiment, an adhesively backed insulator washer 153 is used to affix the feedthrough capacitor 140 onto the surface of the alumina substrate 156.

There are two different methods of electrical attachment to the feedthrough capacitor illustrated. In the left hand hole, we have a solid fill of a solder, braze or thermal-setting conductive material 155. A simplified electrical attachment is shown on the right side wherein, a solder bump or ball grid array (BGA) 151 is first dispensed and then the capacitor is aligned and placed over it. Then, temperature is applied to reflow the solder into place as shown. The solder makes electrical contact with the platinum filled via hole 142*a*', 142*b*' and also with the capacitor terminations 166.

In accordance with good EMC principles, the feedthrough capacitor 140 is disposed immediately at the point of EMI ingress into the inside of the device housing 124. In this way, high frequency EMI can be decoupled and diverted to the device housing 124 without adversely effecting AIMD sensitive electronic circuits. Feedthrough capacitor active electrode plate sets 144*a* and 144*b* are both connected to the capacitor inside diameter metallization 166, The capacitor ground electrode plate sets 146 make contact with the capacitor outside diameter or perimeter metallization 164. An electrical connection 152 is made from the capacitor outside diameter ground metallization 164 and the gold braze 154 of ferrule 134. This makes a low impedance oxide free electrical connection which is superior for high frequency performance.

Figure 14:
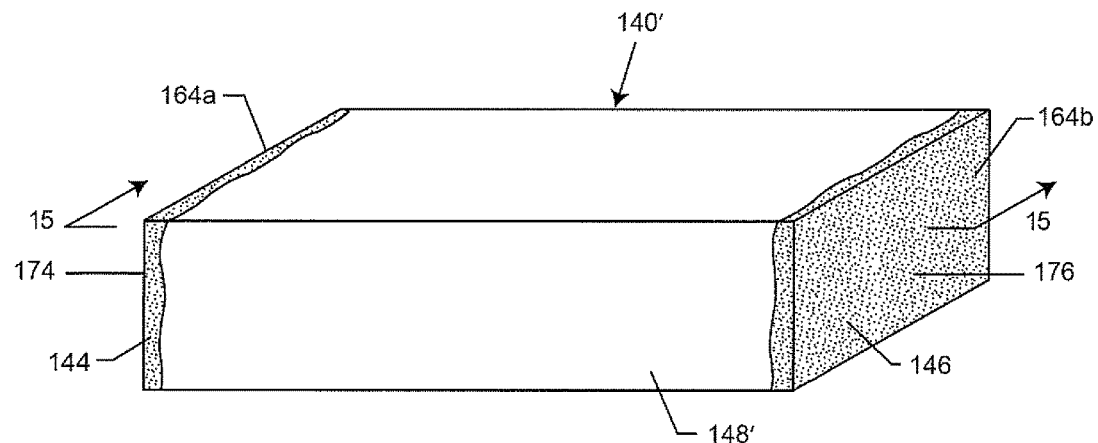
FIG. 14 is a perspective view of a monolithic ceramic capacitor (MLCC)

FIG. 14 is a prior art multi layered ceramic capacitor (MLCC) 140'. These are made by the hundreds of millions per day to service consumer electronics and other markets. Virtually all computers, cell phones and other types of electronic devices have many of these. One can see that the MLCC 140' has a body generally consisting of a high dielectric constant ceramic 148' such as barium titanate. It also has a pair of solderable termination surfaces 164*a*, 164*b* at either end. These solderable termination surfaces 164*a*, 164*b* provide a convenient way to make a connection to the internal electrode plates 144, 146 of the MLCC capacitor 140'. FIG. 14 can also take the shape and characteristics of a number of other types of capacitor technologies, including rectangular, cylindrical, round, tantalum, aluminum electrolytic, stacked film or any other type of capacitor technology.

Figure 15:
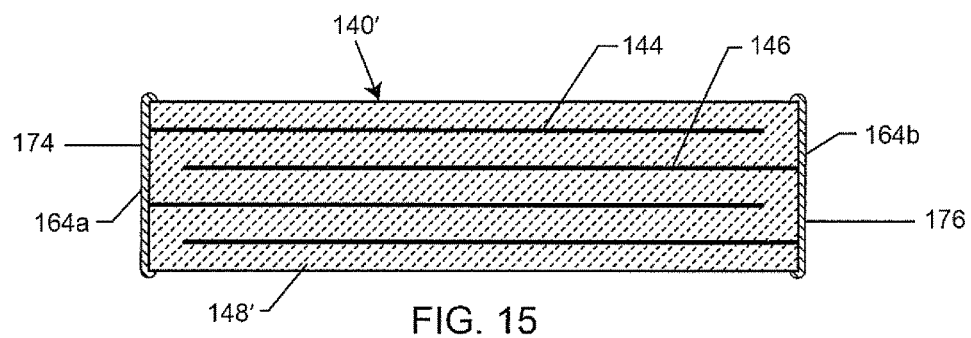
FIG. 15 is a cross-sectional view of the monolithic ceramic capacitor, taken along the line 15-15 of FIG. 14.

FIG. 15 is a sectional view taken from section 15-15 in FIG. 14. The MLCC 140' includes a left hand electrode plate set 144 and a right hand electrode plate set 146. One can see that the left hand electrode plate set 146 is electrically connected to the external metallization surface 164*a*. The opposite, right hand electrode plate set 146 is shown connected to the external metallization surface 164*b*. Prior art MLCC 140' and equivalent chip capacitors are also known as two-terminal capacitors. That is, there are only two ways electrical energy can connect to the body of the capacitor. In FIGS. 14 and 15, the first terminal 174 is on the left side and the second terminal 176 is on the right side. As defined herein, MLCC capacitors are two-terminal devices. In contrast, feedthrough capacitors are three-terminal devices which have very low self-inductance and make excellent high frequency EMI filters.

Figure 16:
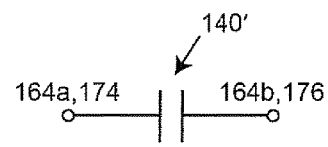
FIG. 16 is an electrical schematic diagram of an ideal MLCC capacitor as illustrated in FIGS. 14 and 15.

FIG. 16 is the schematic diagram of the MLCC chip capacitor 140' illustrated in FIGS. 14 and 15.

Figure 17:
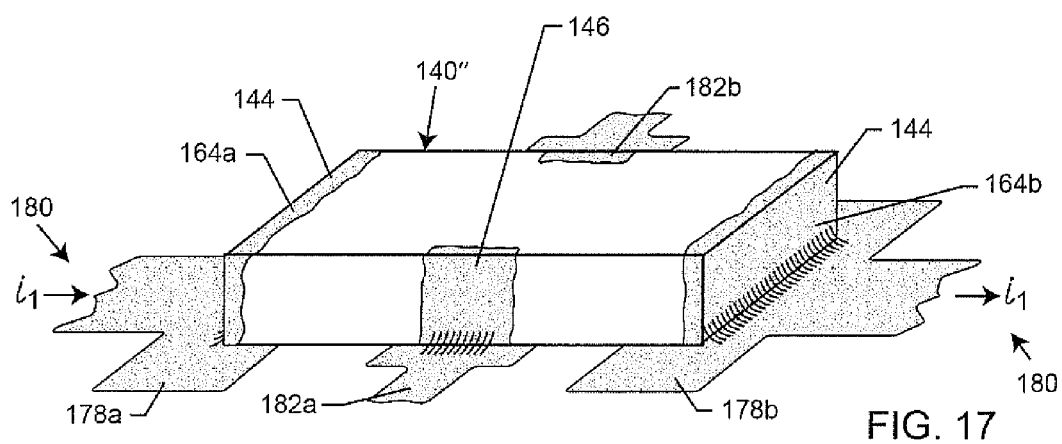
FIG. 17 is a flat-through three-terminal capacitor.

FIG. 17 illustrates another type of prior art 3-terminal filter capacitor known as a flat-through capacitor 140". It is connected at each end to a circuit trace 178a, 178b. A circuit current 180 passes all the way through the capacitor 140". The capacitor 140" is also connected to ground circuit paths 182a, 182b. The overlap of the active electrodes and the ground electrodes creates the capacitance.

Figure 18:
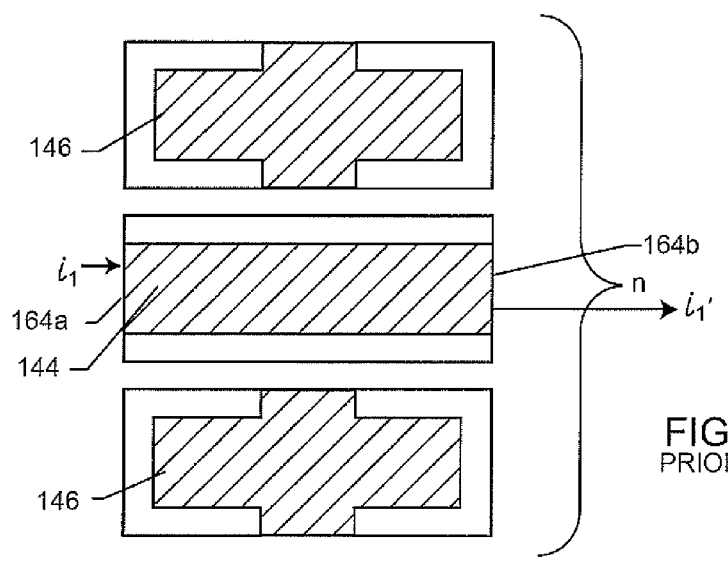
FIG. 18 illustrates the internal electrode plates of the flat-through capacitor of FIG. 17.

FIG. 18 illustrates the internal electrode plates of the flat-through capacitor 140" of FIG. 17. A set of ground plates is illustrated as 146. The through electrode plate 144 is connected to capacitor termination surfaces 164a, 164b.

Figure 18A:
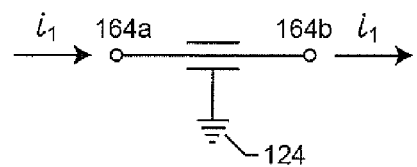
FIG. 18A is the electrical schematic of FIGS. 17 and 18.

FIG. 18A is the schematic of the 3-terminal flat-through capacitor of FIG. 17. One can see that it is a true 3-terminal device consisting of terminals 164a, 164b and ground, which is the AIMD housing 124. As shown, the circuit current passes all the way through the capacitor, as illustrated.

Figure 19:
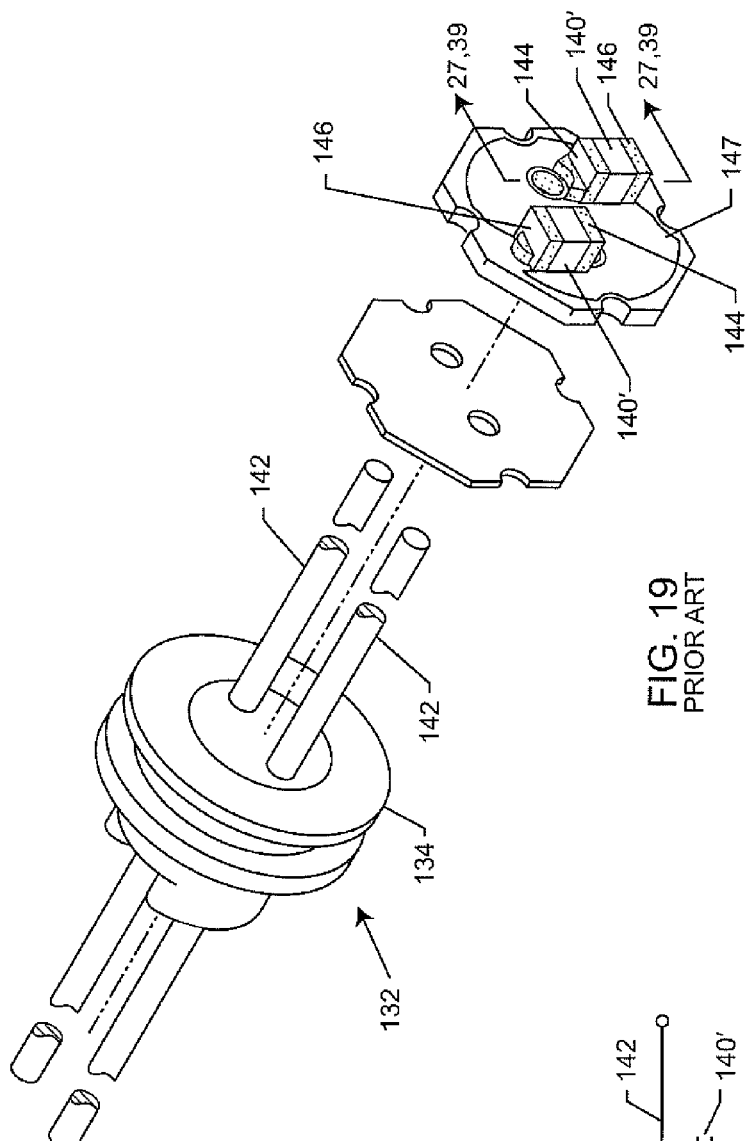
FIG. 19 is a perspective exploded view of a multi-lead hermetic feedthrough with substrate mounted MLCCs showing use of a substrate between the feedthrough and the filter support assembly.

FIG. 19 illustrates a method of attaching MLCC chip capacitors 140' directly to the hermetic terminal 132. In accordance with the present invention, the MLCC capacitors 140' would be of relatively low dielectric constant, like NPO such that they will have a high number of electrode plates thereby minimizing their ESR. This would make them very effective in diverting high levels of RF current at an MRI RF pulsed frequency. One is referred to U.S. Pat. Nos. 5,896, 267 and 5,650,759, both to Hittman et al., which more thoroughly describe the use of MLCC capacitors as filters attached at or near the hermetic terminal of an active implantable medical device. These two patents are incorporated herein by reference.

Figure 19A:
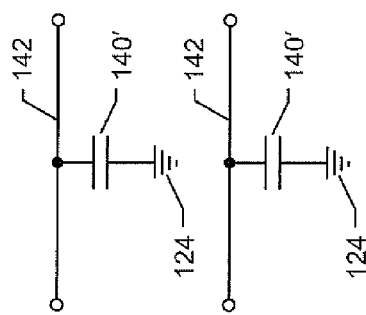
FIG. 19A is the electrical schematic of FIG. 19.

FIG. 19A is the schematic diagram of the bipolar MLCC filter of FIG. 19. As shown, these are 2-terminal capacitors with 1 terminal connected to the leadwire 142 and the other terminal connected to ground, which is also the AIMD housing 124.

FIG. 20 is a cross-section of a typical MLCC capacitor 140', such as those used in FIGS. 14 and 19 (except that the ESR would be high due to the low number of electrodes 144,146). The principles of this cross-section are also equally applicable to any type of feedthrough capacitor 140, such as that described in FIGS. 7 and 9. In general, the equivalent series resistance of a capacitor depends upon a number of very important variables. The capacitor's ESR is the sum of the connection resistance ($R_c$) 184, the resistance of attachment materials ($R_a$) 186, the resistance of capacitor metallization (used to attach to internal electrode plates) ($R_m$) 188, the resistance of the electrodes ($R_e$) 190 and 190' and also the resistance of the dielectric loss tangent ($R_{DL}$) 192. There is also another type of resistance (not shown) which occurs at very high frequency, known as skin effect ($R_s$). This is a situation in which the bulk of the current flow is on the skin of electrodes and circuit connections instead of uniformly distributed throughout a conductor. This has the affect also of increasing a capacitor's ESR. In general, for typical MRI RF pulsed frequencies, skin effect can be ignored (it's mostly a greater than 500 MHz phenomenon).

FIG. 21 is the schematic diagram from FIG. 20 showing that for these purposes, the capacitor's ESR is the sum of the connection resistance ($R_c$) 184, the connection material ($R_a$) 186, the metallization ($R_m$) 188, the electrode plate resistance ($R_e$) 190 and the capacitor's dielectric loss ($R_{DL}$) 192. The capacitor's dielectric loss ($R_{DL}$) 192 is frequency variable, which will be explained in further detail. For a well designed and properly installed capacitor, many of these resistances are so small that they can be ignored. For example, referring once again to FIG. 20, if the capacitor metallization ($R_m$) 188 is well designed and properly attached, it will have a trivially small resistance. In a similar fashion, if the electrical attachment material ($R_a$) 186 is a solder or a proper thermal-setting conductive adhesive, it will also have a trivial amount of resistance. If the system is attached to gold or another similar non-oxidized surface, then the connection resistance ($R_c$) 184 would also be trivially small or about zero. Referring once again to FIG. 21, one can see that the total ohmic losses are $R_o$ 200, and in this case, $R_o$ consists almost entirely of the total electrode plate resistance ($R_e$(total)) 190. This is why it is so important in the present invention to maximize the number of electrode plates. At high frequency, the ohmic loss of the low dielectric constant capacitor is almost entirely due to the resistive loss of the active and ground electrode plates ($R_e$(total) 190).

FIG. 22 gives the equation relating capacitance to the dielectric constant k, the active (overlap area) of the electrode plates A, the number of electrode plates n and the dielectric thickness d. Since the dielectric constant k is directly related to the capacitance C, one can see how dramatically the capacitance would rise when the dielectric constant k is 2500 as opposed to a k below 200 for an EIA Class I dielectric. Assuming a constant dielectric thickness d for a particular voltage rating, the only way to increase the capacitance to its original value, would be to greatly increase the number of electrode plates. In the prior art, this would be counterintuitive. However, in the present invention, this is exactly what we want to do. A high number of electrode plates drives down the high frequency ohmic losses and thereby greatly increases the efficiency of the capacitor to pull RF energy out of an implanted lead during MRI scans. In addition, the high number of electrode plates has a very low equivalent series resistance at the MRI RF-pulsed frequency, thereby significantly reducing the amount of heat that would be produced in the filter diverter capacitor 140.

Figures 23, 24:
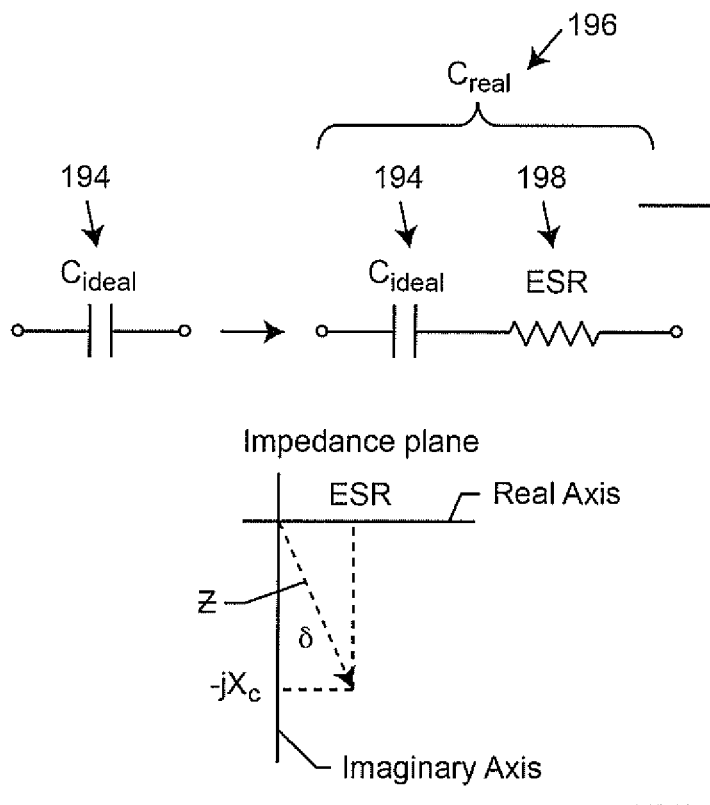
FIG. 23 shows the difference between an ideal capacitor and a real capacitor, including dielectric loss tangent and dissipation factor.
FIG. 24 gives the formulas for capacitive reactance, dissipation factor, equivalent series resistance (ESR) and dielectric loss tangent.

FIG. 23 illustrates an ideal capacitor 194 and also a non-ideal capacitor 196 which consists of an ideal capacitor 194 in series with its ESR 198. For the purposes of the present discussion, a capacitor's series inductance or insulation resistance (a parallel resistance) can both be ignored. This is because the inductance of feedthrough capacitors is quite low at MRI RF-pulsed frequencies. Further, the capacitor's insulation resistance is generally in the megohms or gigohms range, which is so high, it can also be ignored as a parallel path. Also shown is a graph of the impedance plane showing the capacitor ESR in the real axis and the capacitive reactance $-jX_c$ shown on the imaginary axis. The capacitor's loss tangent δ is also illustrated.

In FIG. 24, equations are given for capacitive reactance $X_c$, impedance Z, and dissipation factor DF and also for the tangent of δ which is also defined as dissipation factor DF. Historically, dissipation factor has been expressed as a percent, such as 2.5% maximum. This would mean that the allowable dissipation factor would be 2.5% of the capacitor's capacitance reactance at a particular frequency. Usually, due to dielectric losses, this number is dominated at low frequencies by the capacitor's dielectric loss. The capacitor's dielectric loss is generally related to its dielectric constant and the frequency of the driving energy. For example, if the frequency of an applied sinusoid is relatively low (say 60 Hz) then the crystal lattice of the capacitor has plenty of time to deflect back and forth under the electrical stress and in so doing, produces a significant amount of heat which is a type of real or resistive loss. At 1 kHz, the capacitor dielectric structure (or dipoles, if one uses that theory) vibrates at a higher frequency. As one goes higher and higher in frequency, say to 10 MHz, then for the Class I dielectrics of the present invention, there would be very little movement in the crystal lattice and accordingly, very little heat generated due to dielectric loss. It will be further illustrated how dielectric loss varies with frequency. In the past, particularly as described by testing specifications such as MIL-Std-202, dissipation factor is measured either at 1 kHz, or in some cases, at 1 MHz. Unfortunately, this data is misleading at MRI RF-pulsed frequencies which generally are 21.28 MHz (0.5 T), 64 MHz (1.5 T) or higher. For most dielectrics, the high frequency ohmic loss, due to the capacitor's electrode plates, is so low that it is masked by the capacitor's dielectric loss when measured at low frequencies such as 1 kHz or 1 MHz. This will be explained in subsequent figures.

Figure 25:
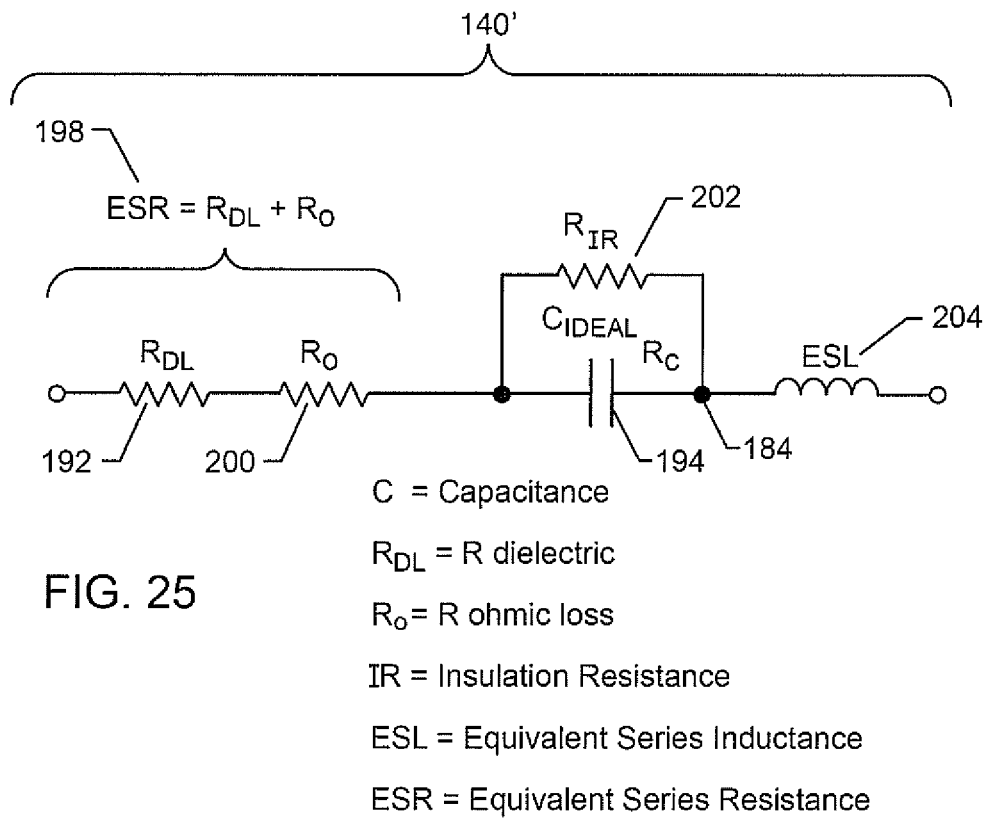
FIG. 25 is an equivalent circuit model for a real capacitor.

FIG. 25 is a more complete schematic for a capacitor, which has been simplified from FIG. 21. ($R_o$) represents ohmic loss 200 which is the sum of the connection loss ($R_c$) 184, the attachment materials ($R_a$) 186, the metallization ($R_m$) 188, and the electrode plate resistance ($R_e$) 190. Assuming that the connection resistance ($R_c$) 184 is very low, such as in attachment to gold, and that the attachment material ($R_a$) 186 has a very low resistivity, such as a thermal-setting conductive adhesive or a solder, and assuming that the capacitor metallization 188 materials have very little ohmic resistance to the electrode plates, then one can assume that the bulk of the entire ohmic loss ($R_o$) 200 is equal to the resistance of the electrode stack ($R_e$(total) 190. As previously described, the resistance of the electrode stack depends on the length, the width and the thickness of the electrodes and importantly, also the number of electrodes that are in parallel. Therefore, reducing the dielectric loss and maximizing the number of electrodes are key featured embodiments of the present invention.

Figure 26:
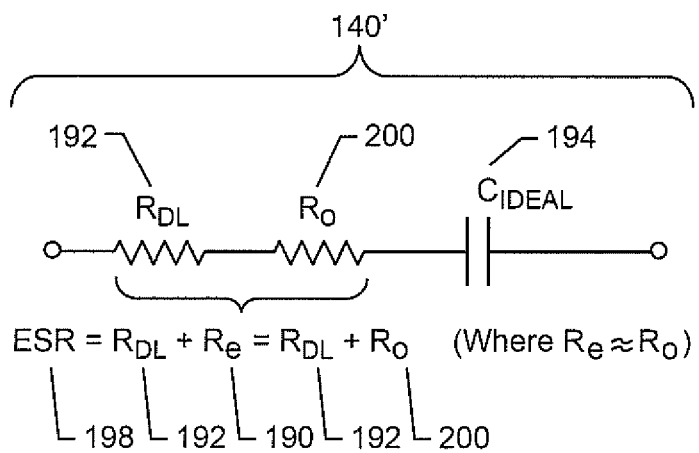
FIG. 26 is a schematic illustrating a simplified model for capacitor ESR.

FIG. 26 is a simplified schematic diagram of the present invention from FIG. 25 showing that the ESR 198 is the sum of the dielectric loss ($R_{DL}$) 192 plus the total parallel resistance of the electrode stack ($R_e$) 190. Referring once again to FIG. 25, one can see that there is a resistor ($R_{IR}$) 202 in parallel with the ideal capacitor C 194. This resistance ($R_{IR}$) 202 is known as the capacitor's insulation resistance. In a high quality capacitor, this resistance value tends to be in the hundreds of megohms or higher and can therefore be ignored as part of the equivalent circuit model for the purposes herein. For three-terminal or physically small MLCCs, the equivalent series inductance (ESL) 204 as shown in FIG. 25 is a very small value and can also be ignored for the purposes herein. In addition, ESL 204 is imaginary and does not contribute to power loss or ESR 198 in a capacitor.

Accordingly, as shown in FIG. 26, the AIMD diverter capacitor 140' ESR 198 is the sum of the dielectric loss ($R_{DL}$) 192, the ohmic losses ($R_o$) 200 and any losses due to skin effect ($R_s$) 206. However, at MRI RF frequencies, skin effect is negligible and may be ignored. Referring once again to FIG. 26, assuming that the capacitor has good metallization, oxide free connection to the ferrule and good electrical attachment materials, then the ohmic losses ($R_o$) 200 are completely dominated by the resistance of the electrodes ($R_e$) 190. Accordingly, for the purposes of the present invention, the ESR 198 is generally equal to the dielectric loss 192 plus the electrode losses ($R_e$) 190. Both of these parameters must be carefully controlled for the high power RF diverter capacitor 140' of the present invention.

It has been shown that dielectric loss is a frequency variable. At MRI RF pulsed frequencies, for an EIA Class I ceramic capacitor, the dielectric loss drops to a very low value (it is essentially zero). Therefore, in the present invention, which is based on EIA Class I dielectrics, the diverter capacitor's 140' ESR 198 is primarily determined by the total resistance of its electrode plates ($R_e$) 190.

Figure 27:
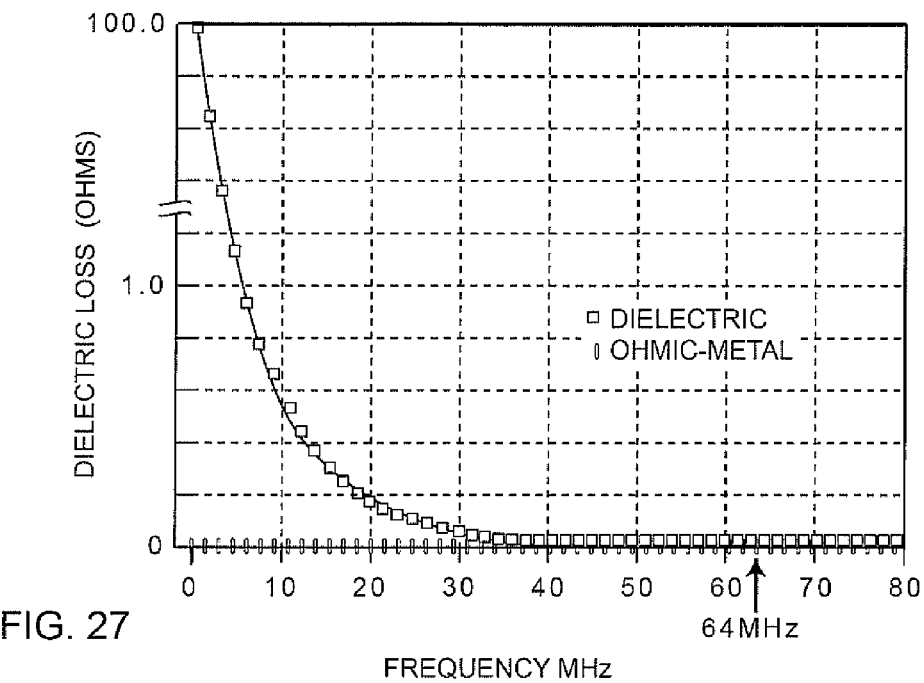
FIG. 27 is a graph illustrating capacitor dielectric loss versus frequency.

FIG. 27 illustrates the dielectric loss in ohms for a relatively low dielectric constant ceramic capacitor. One can see, at low frequencies, the dielectric loss in ohms can be over 100 ohms or even much greater. However, as one increases in frequency, one can see that the dielectric loss drops and is nearly zero at 64 MHz (1.5 T MRI scanner RF-pulsed frequency).

Figure 28:
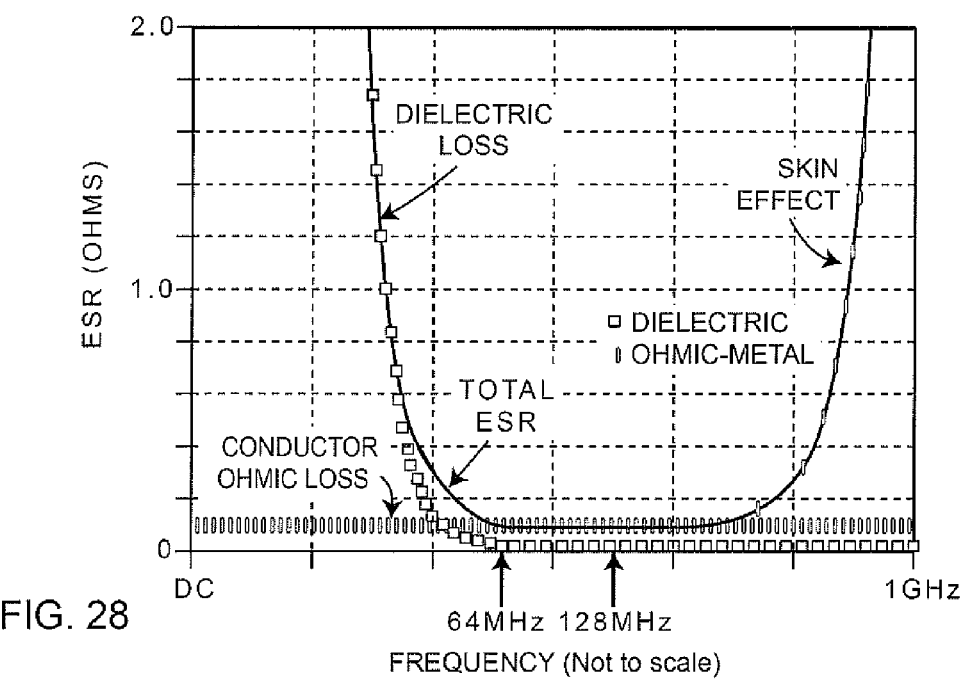
FIG. 28 is a graph illustrating normalized curves which show the capacitor equivalent series resistance (ESR) on the y axis, versus frequency on the x axis.

FIG. 28 shows a U-shaped composite curve. It is the summation of capacitor ohmic loss which includes the total resistance of capacitor electrode plates, electrical attachment materials, capacitor metallization, and electrical connection material. As one can see, ignoring skin effect, the conductor ohmic loss for the capacitor is relatively constant from low frequency all the way to very high frequencies. For a Class I dielectric, the capacitor dielectric loss (marked with small squares) is a very high value at low frequency, and then drops to near zero at MRI RF frequencies such as 64 MHz and 128 MHz. Skin effect is also shown, which would be an ohmic loss for two-terminal type capacitors. The total ESR is the solid line, which is the summation of the capacitor dielectric loss, the capacitor conductor ohmic loss and skin effect. The present invention is directed to make sure the center of this U-shaped curve falls on the range of MRI RF-pulsed frequencies.

FIG. 29 is a table showing an example of losses (actually measured) for a prior art 2000 picofarad X7R (2500 k) feedthrough capacitor. This particular capacitor had a dielectric constant of about 2500. One can see that at 1 kHz, the dissipation factor is about 1591.55 ohms, which when added to the ohmic losses, results in an equivalent series resistance of about 1591.98 ohms. Even at 1 MHz for this capacitor, there is about 1.59 ohms of dissipation factor loss, which when added to the about 0.432 ohms of ohmic loss, yields an ESR of about 2.024 ohms. As one can see, again referring to MIL-Standard-220 and many other test specifications, measuring the capacitor's real losses, at 1 kHz and 1 MHz, is not a useful way to analyze the capacitor's losses at MRI RF-pulsed frequencies. For this, one needs to look in the range from 10 to 500 MHz and realize that as the dissipation factor drops, the ohmic losses still dominate and one ends up with a significant ESR ranging from about 0.59 to about 0.434 ohms.

FIG. 30 dramatically illustrates the difference when one uses an EIA Class I dielectric, such as COG (NPO), which has a dielectric constant of less than about 200. Because of this low dielectric constant, one is forced to use a very high number of electrode plates. This has the effect of greatly reducing the capacitor's ohmic losses. In addition, Class I dielectrics have a lower dissipation factor, particularly at high frequency. Comparing 100 MHz, one can see for the COG dielectric, the ESR is about 0.201 ohms at 100 MHz, which is a significant reduction compared to the X7R capacitor. In the preferred embodiment (illustrated in FIGS. 32-70), the ESR would drop to below 0.1 ohms, which would result in a significantly reduced heat generation in the present invention diverter capacitor 210.

Figure 31:
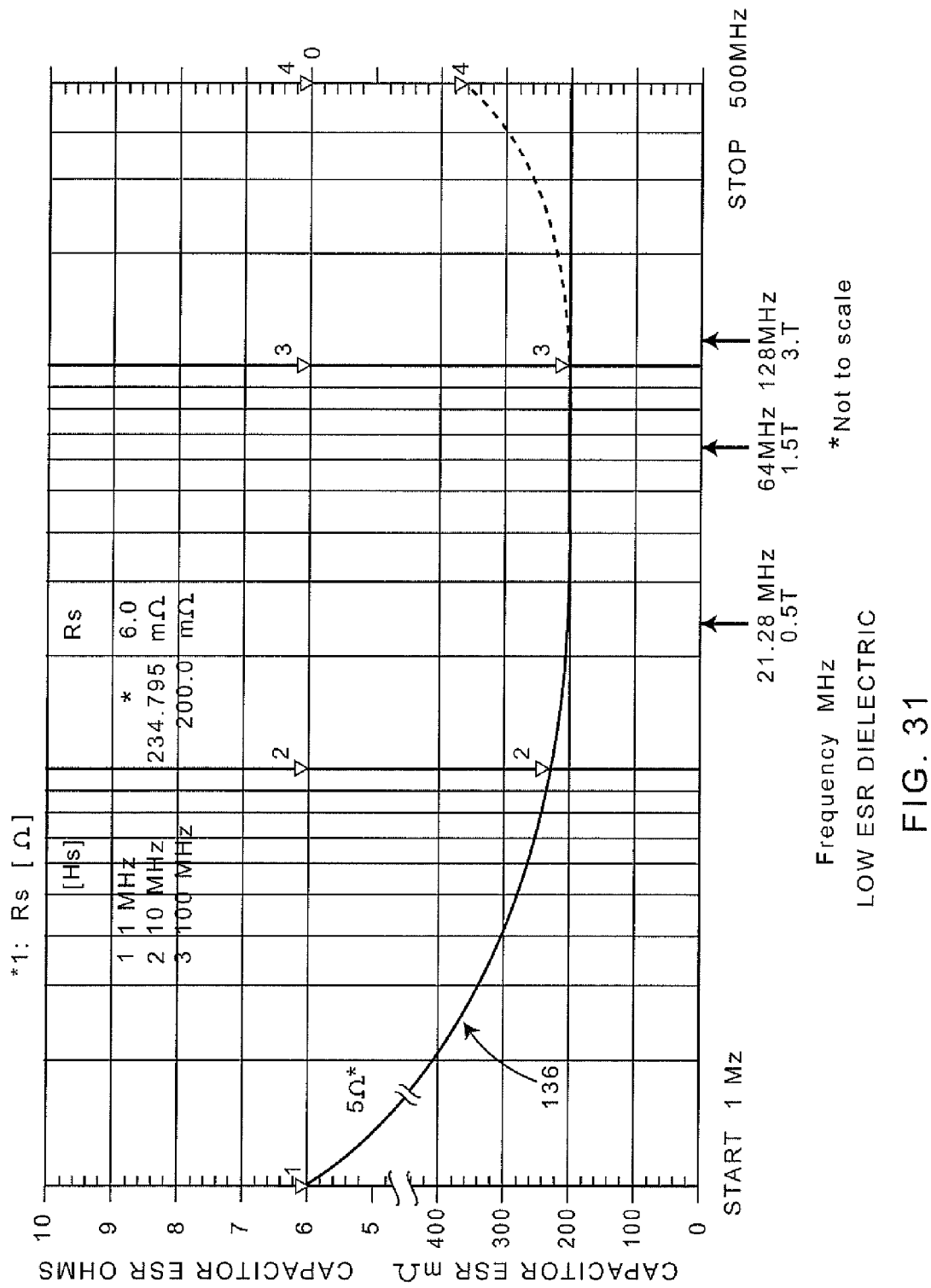
FIG. 31 is a graph illustrating capacitor equivalent series resistance versus frequency as illustrated in a sweep from an Agilent E4991A materials analyzer.

FIG. 31 is a scan of the capacitor's ESR taken from an Agilent Materials Analyzer. At the start frequency of 1 MHz, one can see that the capacitor's 210 ESR is on the order of 6 ohms, which is very high. However, by using a EIA Class I dielectric, by the time one reaches about 21.28 MHz (the frequency of a 0.5 T MRI scanner), the dielectric loss has flattened out. The only loss left is the ohmic loss of the capacitor, which at 100 MHz is only 200 milliohms. Also shown are the RF-pulsed frequencies for a 1.5 Tesla scanner (64 MHz) and a 3 Tesla scanner (128 MHz).

Since the 1960s it has been a common practice in the capacitor industry to measure capacitance and dissipation factor at 1 kHz. The dissipation factor is usually defined as a percentage, for example, 2.5% maximum. What this means is that the dielectric loss resistance can be no more than 2.5% of the capacitive reactance at a certain frequency (usually 1 kHz). For example, if the capacitive reactance for a particular capacitor was 80,000 ohms at 1 kHz with a 2% dissipation factor this would equate to 1600 ohms of resistance at 1 kHz. FIG. 31 also illustrates that the dielectric loss essentially goes to about zero at high frequency. For typical low dielectric constant Class 1 ceramic capacitors, frequencies above 10-20 MHz will be sufficiently high so that the dielectric loss is no longer a factor in the capacitor ESR measurement. In summary, the ESR of the capacitor 210 varies with the capacitance value, the number of electrode plates, and the length and width of the electrode plates. Accordingly, a wide range of "normal" ESR readings can be obtained for many types of capacitors. For one particular capacitor a normal ESR reading might be 0.05 ohms and for another design as much as 10 ohms.

Figures 32, 33:
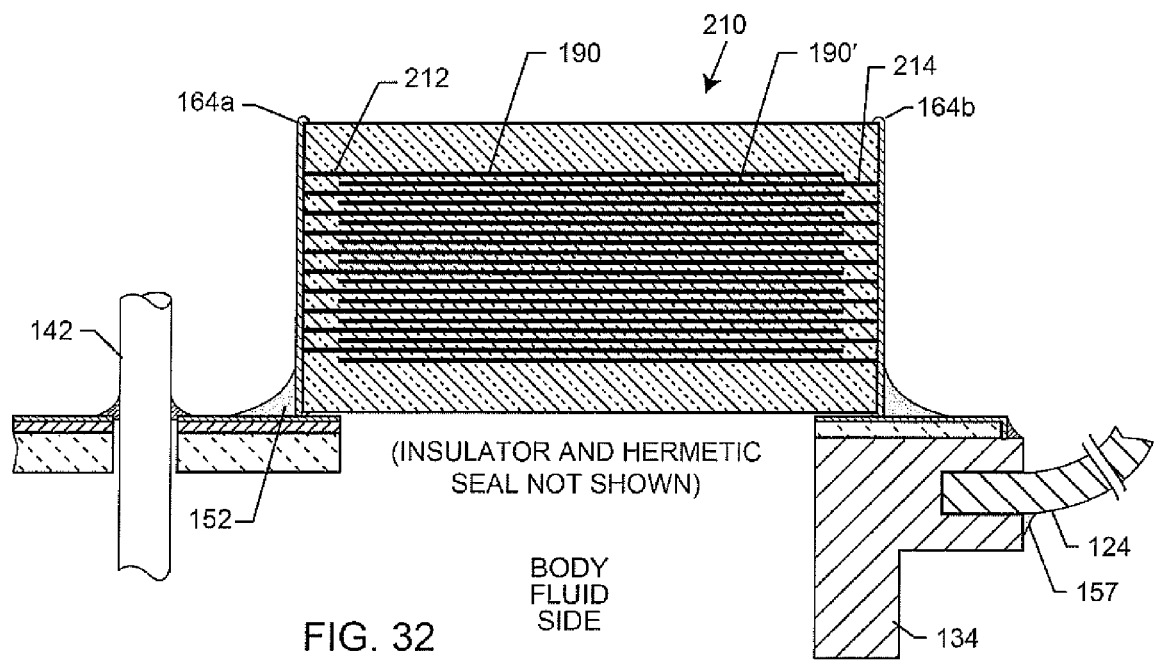
FIG. 32 is a cross-sectional view of a lower k MLCC with an increased number of electrode plates to minimize ESR.
FIG. 33 is an equation showing that the total high frequency electrode resistive losses drop in accordance with the parallel plate formula for capacitor electrodes.

In the present invention, as shown in the embodiment of FIG. 32, maximization of the number of electrode plates in order to reduce the electrode resistance ($R_e$) becomes paramount. In general, in order to increase the number of electrode plates, the effective capacitance area (ECA) can be minimized and the dielectric constant lowered so that one ends up with a relatively high number of electrode plates. One might ask, why doesn't one simply make the electrode plates much thicker in order to decrease their resistance? It would be true that making the electrode plates very thick would reduce their resistance, however, there would be an undesirable consequence. The capacitor would no longer be a monolithic layer and would simply represent a sandwich somewhat like a deck of cards that is ready to come apart at the first thermal shock or piezoelectric effect. It is a basic tenet of ceramic engineering that electrodes be thin enough, and contain enough ceramic powder such that when sintered, the ceramic capacitor structure become truly monolithic. This leaves the designer with only a few effective ways to control the capacitor's ESR. For a given geometry, which is usually dictated by the AIMD design, there are very few degrees of freedom in the length, width and geometry of capacitor electrode plates. Accordingly, in the present invention, maximizing the number of electrode plates becomes a key design factor. This goes hand in hand with the capacitor's dielectric constant k. In other words, reducing the dielectric constant means that the number of capacitor electrode plates must increase to achieve the same capacitance value. This naturally reduces the capacitor's ESR and increases its ability to handle high levels of RF current. Another reason to keep the ESR 198 of the diverter capacitor's 210 extremely low is so it does not overheat while diverting high levels of RF current to the EDS housing 124 of the AIMD 100. The RF currents are literally conducted through the capacitor's 210 electrode plates 212, 214 and hence through the electrode plate resistance ($R_e$) 190. Electrode plate resistance ($R_e$) 190 is the sum total of the resistance of all of the electrode plates 212, 214 acting in parallel. If the electrode plate resistance ($R_e$) 190 were high, then there would be a tremendous amount of $I^2R$ power loss that occurs and the capacitor 210 would rapidly get very hot and perhaps destroy itself and/or the surrounding electrical connections or materials. Another reason to keep the capacitor 210 ESR 198 relatively low is so that it represents a very low impedance Z at the MRI RF pulsed frequency. This will increase its ability to draw energy from the implanted lead 110 and divert it as an energy dissipating surface to the AIMD housing 124. If the capacitor represented too high of an impedance, this would reduce the current, but would also mean that more energy was undesirably left in the implanted lead 110. Lowering the impedance Z of the diverter capacitor 210 also means that it will be a better EMI filter by offering increased attenuation at the MRI RF pulsed frequency.

However, the most important reason of all to keep the overall resistance 190 of the electrode plates extremely low (in other words, extremely low ESR) is to prevent the overheating of the primary filter capacitor 210 itself. It has been demonstrated that overheating of this capacitor causes the adjacent AIMD housing 124 to overheat. This is highly undesirable in a human incision pocket. Typically, the AIMD is placed under the skin, under the fat or even under a muscle. There are various FDA and CEM42 Standards that limit the amount of heating in various types of body tissues. In general, the amount of this heating is limited to 4° C. (that can vary with body tissue). For example, for a deep brain stimulator, a subdural implanted AIMD must have a much lower temperature rise due to the extreme thermal sensitivity of brain matter. This is in contrast to a pectoral pocket created for cardiac pacemaker or ICD, which represents less thermally sensitive tissues and fats. In any event, it is a major feature of the embodiments herein to prevent the overheating of the primary filter component in order to minimize or eliminate AIMD can 124 heating.

In general, the filter capacitor 410, 210 of the present invention may have at least 10 electrode plates. However, with a k up to one thousand, one could envision a design of a capacitor having an intermediate dielectric constant of say 400. In this case, it might be possible to design a capacitor with 5 electrode plates (depending upon their length and width) and still have a low enough ESR in accordance with the present invention. (For example, 5 active electrode plates with 5 ground electrode plates.) Alternatively, the number of electrode plates could be as high as 20, 40 or even 100 or more, but the critical parameter is that the capacitor's equivalent series resistance never exceeds 2 ohms at the MRI RF-pulsed frequency. In various embodiments, the ESR would be <0.5 ohms or 0.1 ohms.

FIG. 32 illustrates a cross-section of a multilayer ceramic capacitor MLCC 210 of the present invention which is very similar to the prior art MLCC 140' illustrated in FIGS. 14, 19 and 20. FIG. 32 can also be equivalent to any of the aforementioned feedthrough capacitors. In the present invention, feedthrough capacitors or MLCCs can act as high power RF energy diverters. Energy diverters using an energy dissipation surface 134, 124 are more thoroughly described in Published Application Nos. 2010/0217262 and 2010/0023000, the contents of which are incorporated herein by reference. The key difference is that the number of electrode plates, both active 212 and ground 214, has been substantially increased in order to reduce the capacitor's 210 ESR 198 at the MRI RF pulsed frequency to below 2 ohms. In a particularly preferred embodiment, the capacitor's ESR 198 would be below 1 ohm. As previously mentioned, a way to accomplish this without the capacitance value becoming too high would be to decrease the dielectric constant such that a high number of electrode plates would be required. In a particularly preferred embodiment, the dielectric material would be an EIA Standard Class I type such as NPO. Referring once again to FIG. 32, one can see the active (left hand) electrode plates 212 and the ground electrode plates (right hand) 214 stacked in interleaved relation. An electrical attachment material 152 is shown which connects the capacitor metallization 164a and 164b to the ferrule of a hermetic terminal 134. In general, the electrical connection material 152 would be highly electrical conductive, but not necessarily highly thermally-conductive. In summary, the capacitor 210 embodied in FIG. 32 is based on an EIA Class I dielectric, which means its dielectric constant is relatively low and its temperature coefficient, as given by standard ANSI/EIA-198-1, published Oct. 29, 2002, with reference to Table 2 permissible capacitance change from 25 degrees C. (ppm/degree C.) for Class I ceramic dielectrics. This indicates that the maximum allowable change varies from +400 to −7112 parts per million per degrees centigrade. As previously mentioned, a particularly preferred embodiment would be the COG dielectric, which is also commonly referred to as NPO.

FIG. 33 is an equation showing the effect of the parallel plate resistances. FIG. 33 gives the equation for the total resistance of the capacitor's electrode plates ($R_{et}$) 190 as the parallel summation of all of the capacitors' electrode plates 212, 214 ("n" electrode plates).

Figure 34:
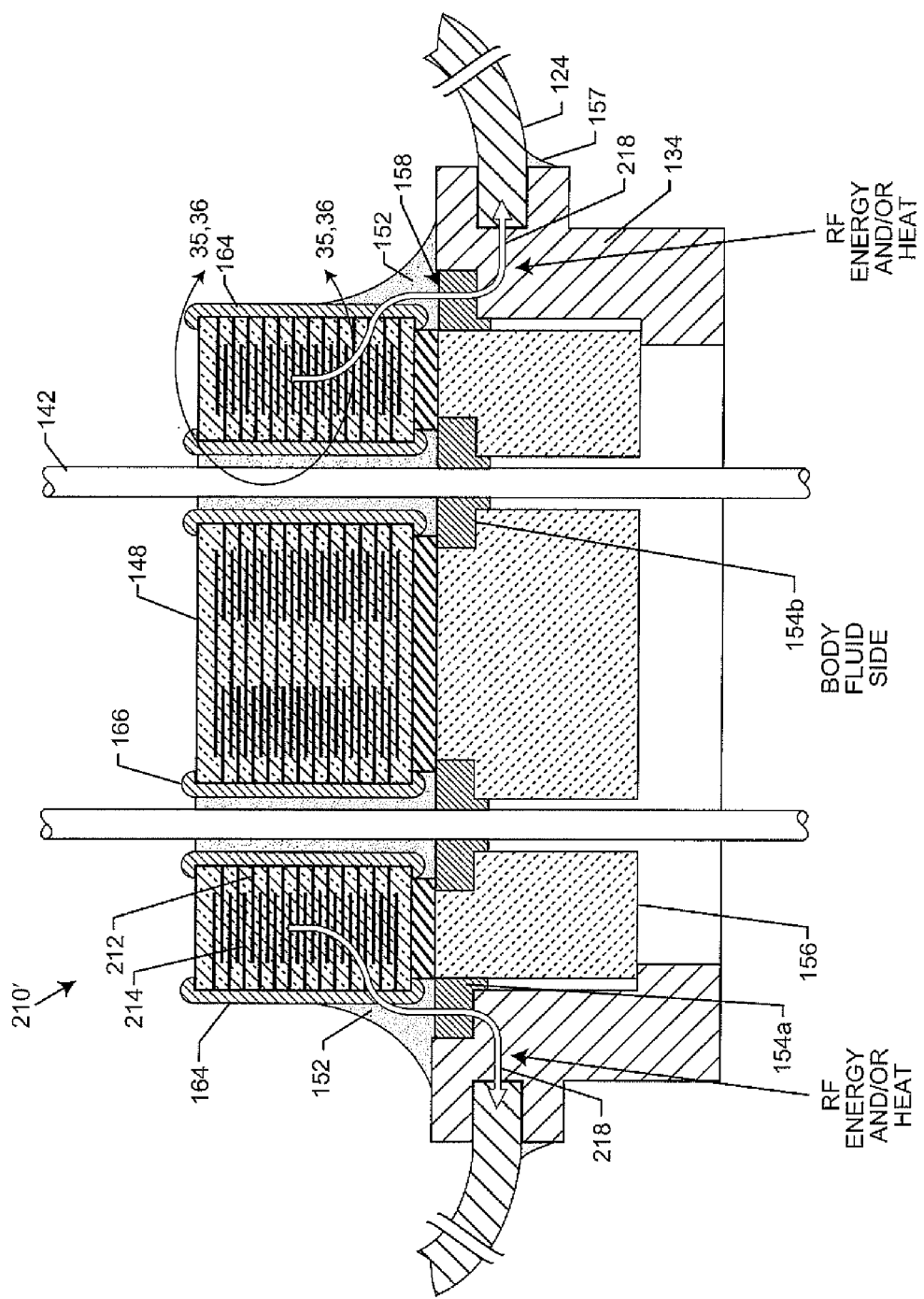
FIG. 34 is a cross-sectional view of a quad polar feedthrough capacitor similar to FIGS. 9 and 10 except that it is low ESR and designed for maximal heat flow.

FIG. 34 is very similar to the cross-section of the quad polar capacitor previously described in FIG. 9-10. Again, the number of electrode plates 212, 214 have been increased in accordance with the present invention such that the FIG. 34 quad polar diverter capacitor 210' has a high frequency ESR 198 generally less than 2 ohms. Referring once again to FIG. 34, one can see that the capacitor outside diameter (ground) metallization 164 is attached using a conductive material 152 to a gold surface 158 on ferrule 134. All of these connections, when properly done, have negligible resistance. Accordingly, the capacitor's 210' ESR 198 at high frequency is made up of the total of the resistance ($R_e$) 190 of the ground electrode plates 214 and the resistance ($R_{e'}$) 190' of the active electrode plates 212 all acting in parallel. As previously stated, for Class I dielectrics, the capacitor's dielectric loss 192 can be ignored at MRI RF pulsed frequencies since it becomes negligible at RF-pulsed frequencies. Also, for a feedthrough capacitor geometry, skin effect 206 is also negligible. Referring once again to FIG. 7-8, one can see a similar rectangular quadpolar capacitor that is attached to a gold braze surface 158.

Figure 35:
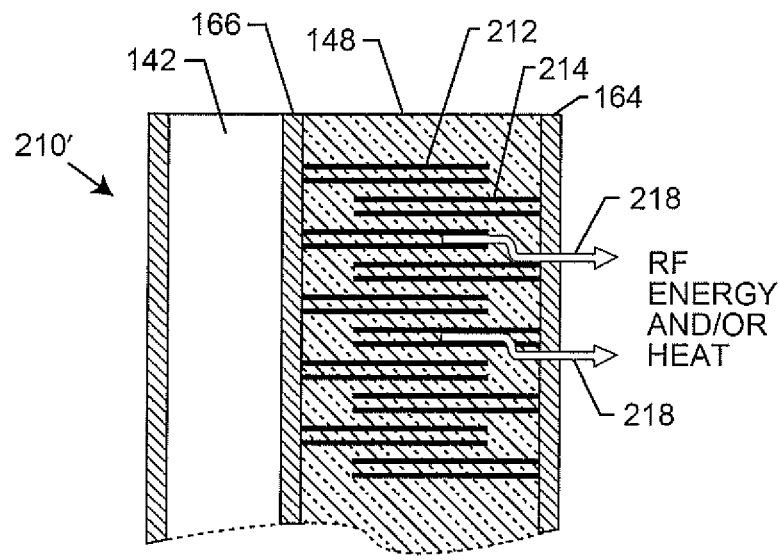
FIG. 35 is a partial section taken from section 35-35 from FIG. 34 illustrating dual electrode plates to minimize capacitor ESR and maximize heat flow out of the capacitor.

FIG. 35 is taken from section 35-35 from FIG. 34 and illustrates a doubling of the capacitor's active 212 and ground 214 electrode plates. Doubling the electrode plates 212, 214 is very effective since both plates are still exposed to the capacitor's internal electric fields and therefore, both sets of doubled plates will have electrode plate displacement currents (RF currents). This has the effect of greatly increasing the number of electrode plates as illustrated in the equation in FIG. 33, which significantly reduces the overall electrode plate resistance. Dual electrodes are shown in U.S. Pat. No. 5,978,204 to Stevenson el al., the contents of which are incorporated herein by reference. In the '204 patent, the dual electrodes were utilized to facilitate high pulse currents, for example, in an implantable defibrillator application. Double electrodes are very useful in the present invention to drive down electrode plate resistance, thereby driving down the capacitor's 210' high frequency ESR 198 and also to increase the conduction of RF energy and/or heat 218 out of the capacitor 210' during exposure to high power MRI RF-pulsed environments.

Figure 36:
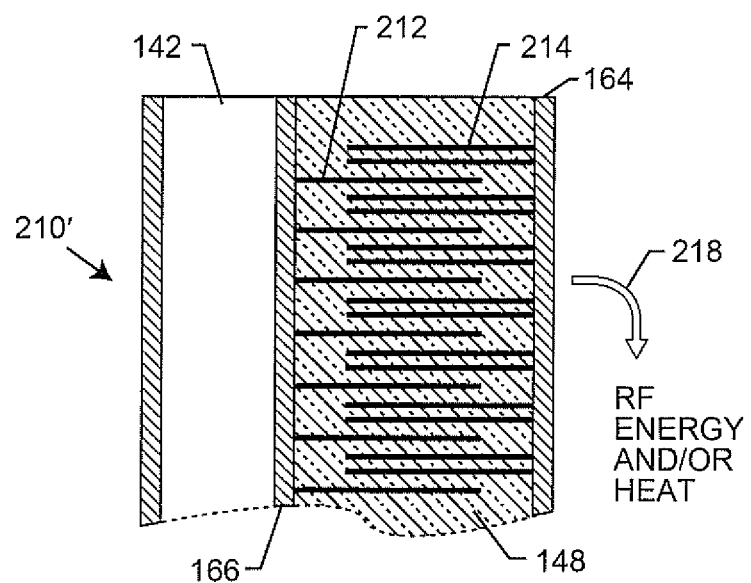
FIG. 36 is similar to FIG. 35 except that just the ground electrode plates have been doubled.

FIG. 36 is very similar to FIG. 35 except in this case, only the ground electrode plates 214 have been doubled. Increasing the number of ground plates 214 is particularly efficient in the removal of heat. As shown, the ground plates 214 are utilized to conduct heat away from the diverter capacitor 210' and direct it through the ferrule of the hermetic seal 134 to the housing 124 of the AIMD 100, which has a relatively large surface area. The relatively large surface area of the AIMD 100 means that a great deal of RF or thermal energy can be dissipated without concentrating it in a small location, which would lead to a very high temperature rise and possibly damage surrounding body tissue damage.

Figure 37:
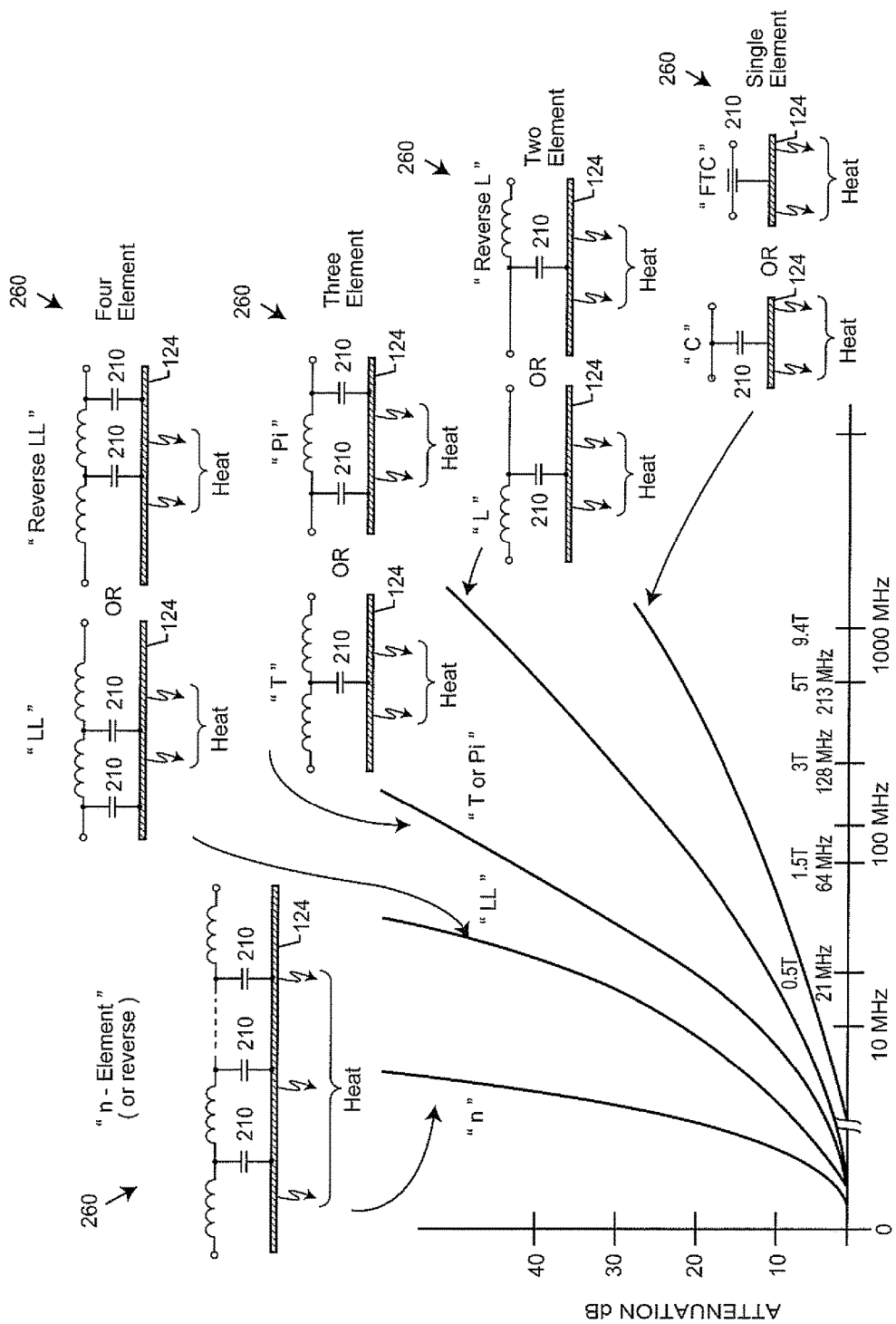
FIG. 37 illustrates a family of lowpass filters indicating the present invention can be anything from a simple diverter capacitor 140 to an "n" element lowpass filter.

FIG. 37 illustrates a family of lowpass filters 260 that all incorporate diverter capacitors 210 of the present invention. As can be seen, these lowpass filters 260 incorporate a variety of capacitors 210 ranging from a simple MLCC chip capacitor "C" to a 3-terminal "feedthrough capacitor-FTC". These capacitors 210 can be combined in various ways with inductors to form "L," "reverse L," "T," "Pi," "LL," or "reverse LL" or "n-element" lowpass filters. In other words, any of the high power RF handling diverter capacitors of the present invention can be combined with any of the lowpass filter circuits as illustrated in FIG. 37 for the purpose of protecting AIMD electronics from EMI while at the same time pulling MRI induced energy from an implanted lead.

Figure 38:
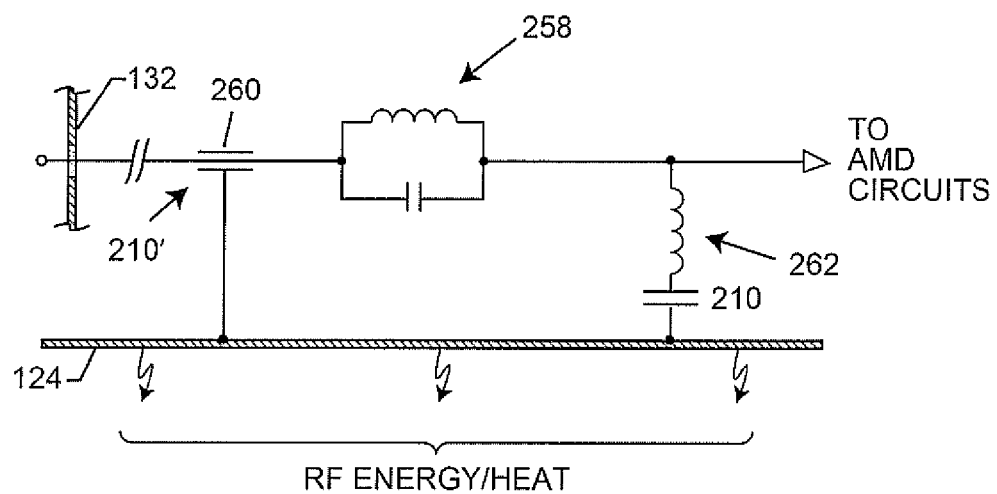
FIG. 38 illustrates a feedthrough diverter capacitor, a bandstop filter and an L-C trap.

FIG. 38 is similar to FIG. 82 from publication 2014/0168850 (which illustrated an electrical schematic embodying an AIMD where the lead enters the AIMD at a hermetic seal 132 and then encounters the low pass filter elements of 260 of FIG. 37) except in this case, the general lowpass filter 260 is in its simplest form. In this case, the general lowpass filter 260 is a feedthrough capacitor 210' which is in turn, connected in series with a bandstop filter 258 which is in turn connected with an L-C trap filter 262 disposed between the circuit trace or lead wire and the AIMD housing 124.

Figure 39:
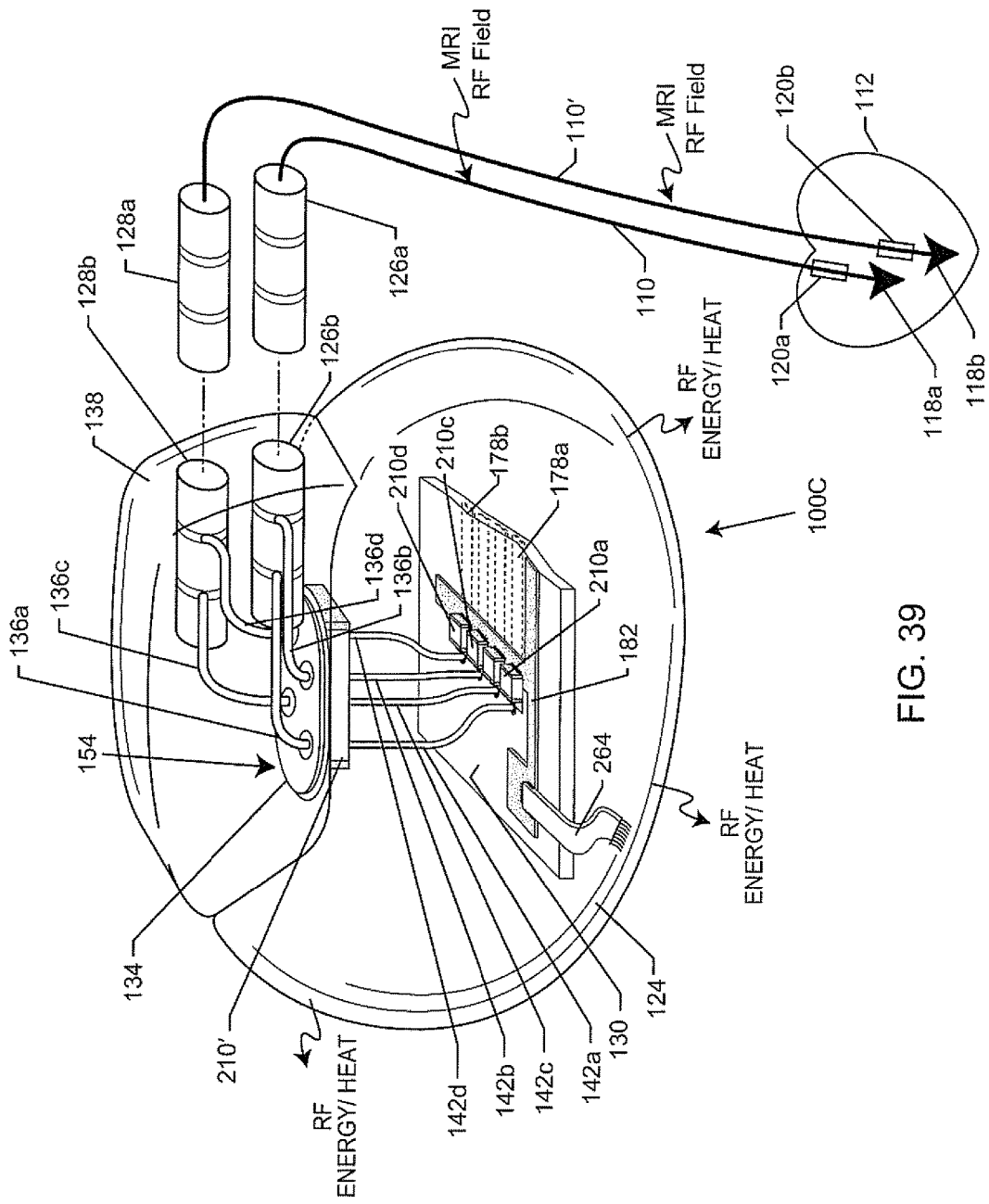
FIG. 39 illustrates a cardiac pacemaker with a diverter feedthrough capacitor and also a circuit board mounted chip capacitor filter which forms a composite filter and also spreads out heat generation.

FIG. 39 shows a dual chamber bipolar cardiac pacemaker 100C with leads implanted into the right atrium and right ventricle of the heart 112. As shown, header block 138 comprises industry standard IS-1 connectors 126, 128. MRI energy is shown being induced on the implanted leads 110 and 110'. As this energy enters the pacemaker housing 124, it encounters diverter capacitor 210'. The diverter capacitor 210' is designed to dissipate high RF power in accordance with the present invention. Accordingly, diverter capacitor 210' has a low dielectric loss at high frequency and also very low high frequency ESR. In this case, there is a secondary row of MLCC chip capacitors 210a through 210d that are mounted at a location distant from the primary diverter capacitor 210'. In this case, the primary diverter capacitor could have a lower capacitance value and the rest of the capacitance is comprised of either board mounted capacitors 210a through 210d or the like. As shown, the circuit board comprises a ground circuit trace 182 that is connected through a low impedance RF conductor or strap 264 conducted to the AIMD housing 124. This low impedance is important to conduct MRI RF currents efficiently to the housing 124 of the AIMD. In order to spread out heat, multiple straps 264 can be used (not shown). A major advantage of the structure shown in FIG. 39 is that by spreading out the filtering function, RF heat or MRI RF energy induced heat is dissipated or spread out over much larger areas. This avoids hot spots on the AIMD housing 124.

Figure 39A:
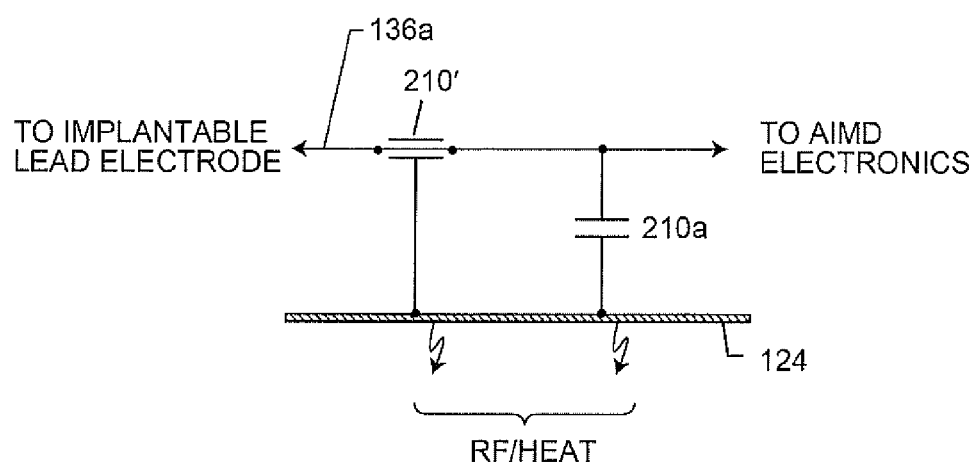
FIG. 39A illustrates the electrical schematic of FIG. 39.

FIG. 39A is the electrical schematic of one of the leadwire circuits 136a of the cardiac pacemaker of FIG. 39. The first low ESR feedthrough capacitor 210' is shown in parallel with the 2-terminal capacitors 210a. It will be appreciated that all four of the quad polar leads 136a through 136d have the same schematic parallel construction.

Referring once again to FIG. 39, one can see that the at least two leadwires 136a through 136d extend from the body fluid side through the hermetic terminal 154 in non-conductive relationship and then through feedthrough capacitor 210'. These leadwires then extend down inside the AIMD housing 124 to either via holes or circuit trace lands on circuit board 130. The other end of the MLCC chip capacitor 210a through 210d is electrically connected through the landing pad or to the via hole to the leadwires 142a-d. For the purposes of this invention, we will refer to the internal electrode plates of the MLCC chips 210 as having ground and active electrode plates. The ground electrode plates are connected to the capacitor's end termination and are therefore, electrically connected to the circuit trace 182. The capacitor's active electrode plate set is electrically connected to the at least two leadwires 142a-d. It will be appreciated by those skilled in the art that circuit board 130 could be an alumina ceramic board, it could be a single layer board, it could be a multilayer board, it could be made of fiberglass or FR4 or any number of materials that circuit boards are made of. It will also be appreciated that a connection from the active side of the capacitors 210 could be accomplished by a flex cable (not shown). The flex cable would replace the leadwires 142a through 142b on the inside of the AIMD housing (or inboard side) and the flex cable would connect to shortened leadwires adjacent the feedthrough capacitor 210'. The use of a flex cable greatly simplifies and facilitates the assembly of the AIMD internal circuits. It should also be noted that the circuit traces 182 and the embedded circuit traces 178 of circuit board 130 (and other circuit traces not shown) can be made from a variety of materials. Since these are inside the hermetically sealed and biocompatible AIMD housing 124, the circuit traces need not be biocompatible themselves. In fact, they could be made of copper, silver, platinum or any other highly conductive material. In an alternative embodiment (FIG. 39B), the chip capacitors 210a could also be mounted directly to the flex cable instead of to the circuit board 130.

Figure 39B:
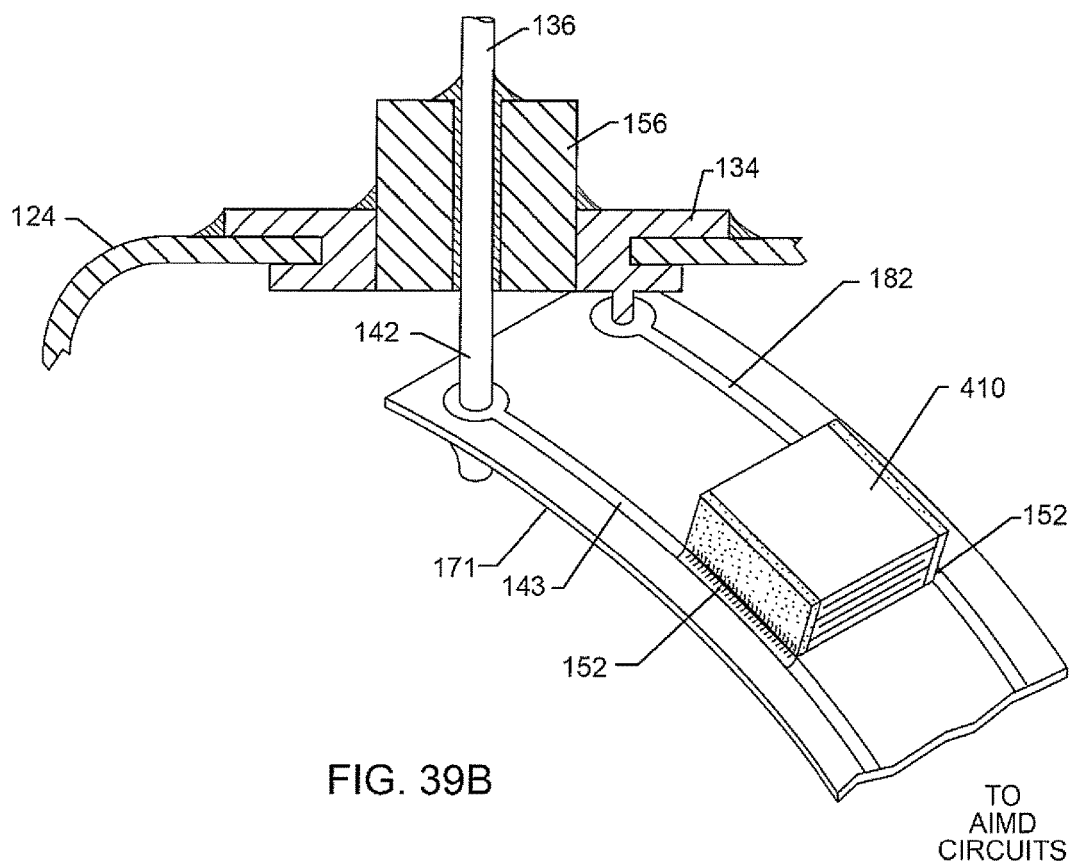
FIG. 39B is a sectional view now showing the capacitor mounted to a flexible connection.
Figure 39C:
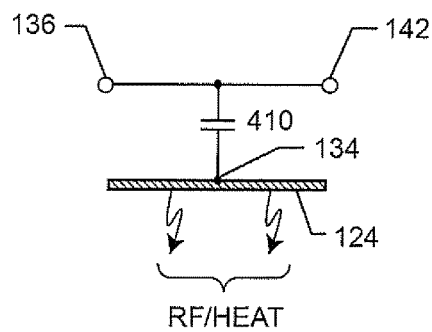
FIG. 39C illustrates the electrical schematic of FIG. 39B.

FIG. 39B illustrates a unipolar hermetic terminal assembly consisting of a ferrule 134, an alumina insulator 156 and a leadwire 136 on the body fluid side wherein, the same leadwire is labeled 142 on the inboard side (or the body side). Shown is a flex cable 171 wherein, one of the circuit traces is connected to the hermetic pin of the feedthrough. There is also a second circuit trace which is connected to ground, which is the potential of the ferrule 134. Importantly, the ferrule 134 is welded to the AIMD housing 124. The chip capacitor 410, which has a k of <1000 in accordance with the present invention, is shown electrically connected between the grounded circuit trace 182 and the active circuit trace 143, which is electrically connected to the feedthrough pin 142, 136. Electrical connection material 152 is shown, which can be a solder, a thermal-setting conductive adhesive or the like.

Referring once again to FIG. 39, one can see that the chip capacitors 210 are considerable distance from the point of leadwire ingress through the hermetic terminal ferrule 134. The structure shown in FIG. 39B puts the MLCC capacitor 410 closer to the point of leadwire ingress 142. This is also the point of ingress of undesirable EMI signals that may be picked up on an implanted lead. Having the chip capacitors as close as possible to the hermetic seal is desirable since it cuts down the inductance or inductive loop inside the device. This helps to prevent the so-called "genie-in-the-bottle" effect wherein, once EMI is inside the AIMD housing, it can cross-couple, reradiate or couple through antenna action to sensitive electronic circuits thereby causing disruption. At MRI RF-pulsed frequencies, this is not a particular concern since for a 1.5 T scanner, the RF-pulsed frequency is 64 MHz. The wavelength of a 64 MHz signal is so long that it really does not effectively re-radiate once inside an AIMD housing. However, if the MRI filter capacitor 410 is also to be used as a broadband low pass filter, for example, where it must filter out very high frequency signals above 1 GHz, such as those signals from cellular telephones, then it is desirable to have the chip capacitor 410 as close as possible to the point of leadwire ingress. Using a chip capacitor for both diverting of MRI RF-pulsed frequencies and also to act as a broadband low pass filter means that one desirably places the MLCC capacitor as close as possible to the point of leadwire ingress. This is shown in FIG. 19 with capacitors 140, which of course, could be capacitors 410 in accordance with the present invention. One is also referred to FIG. 54, which places the MLCC capacitors 410 directly at the point of leadwire ingress of the AIMD housing where the capacitor 410 is connected to the terminal pin and to the gold braze of the ferrule, thereby providing the lowest impedance connection possible. Mounting chip capacitors directly at the point of leadwire ingress is further taught by U.S. Pat. Nos. 5,650,759 and 5,896,267, the contents of which are herein incorporated by reference.

Figure 40:
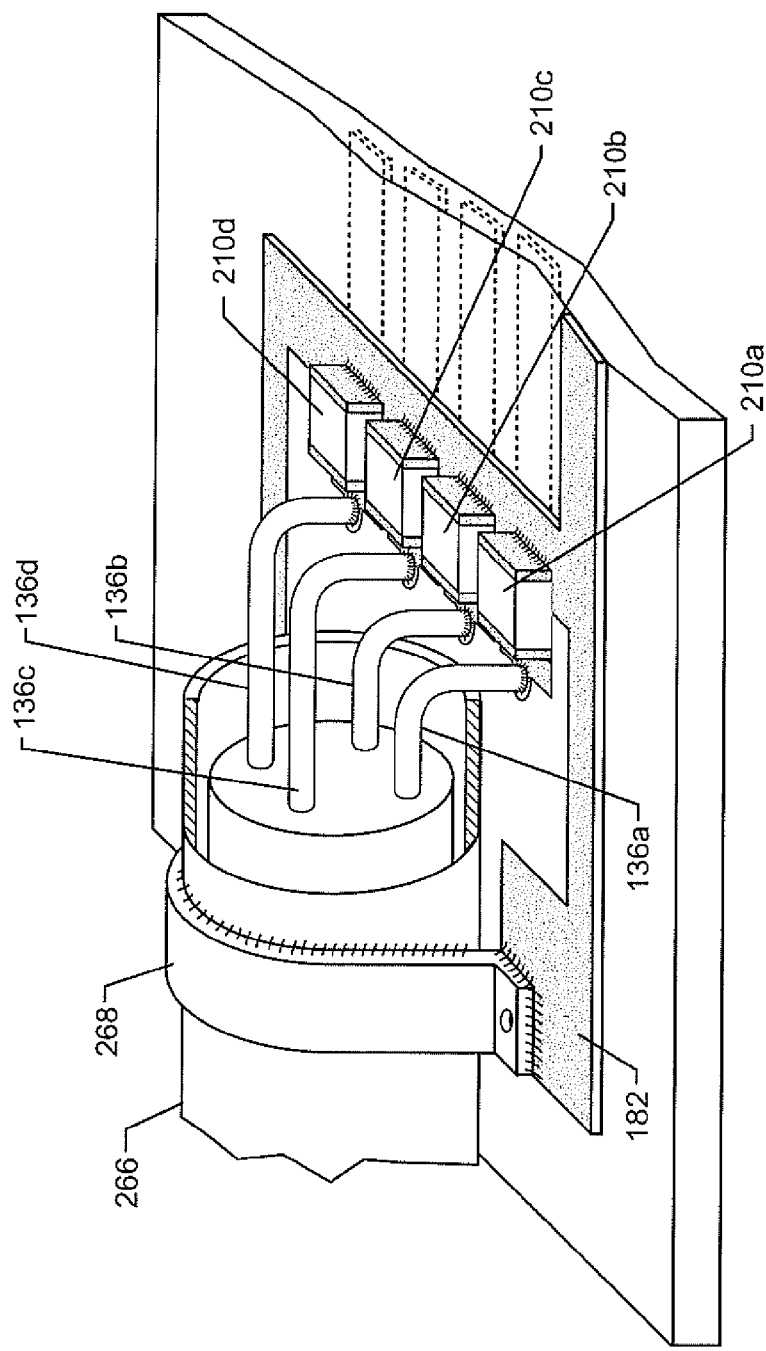
FIG. 40 is a fragmented perspective view of an EMI shield conduit mounted to a circuit board having multiple MLCC chip capacitors.

FIG. 40 shows an alternative embodiment to FIG. 39. A circuit board and chip capacitors 210a through 210d as previously described in FIG. 39 are shown. However in this embodiment, the grounded circuit trace 182 does not need a ground strap or conductor 264 to the AIMD housing. Instead, a shielded conduit assembly 266 is attached to the ferrule of the hermetic terminal (not shown). This shielded conduit 266 is grounded with a strap 268 which is connected to the ground circuit trace 182. This type of EMI shielded conduit assembly is more thoroughly described in U.S. Pat. No. 8,095,224 to Truex et al., the contents of which are incorporated herein by reference.

Figure 41:
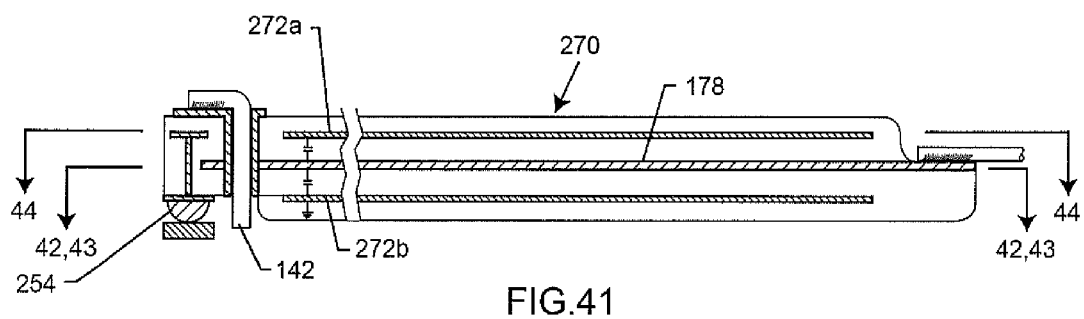
FIG. 41 is a cross-sectional view of an improved flex cable embodying the present invention.

FIG. 41 shows a cross-sectional view of a flex cable or circuit board 270. The flex cable or circuit board 270 is attached on the left using a ball grid array (BGA) type attachment 254. Attachment 254 is further connected to a conductor 142 that goes through a hermetic seal 132 of an AIMD (not shown). These types of flexible circuit traces or substrates are also described in U.S. Pat. No. 8,095,224 to Truex et al., the contents of which are incorporated herein by reference.

Figure 42:
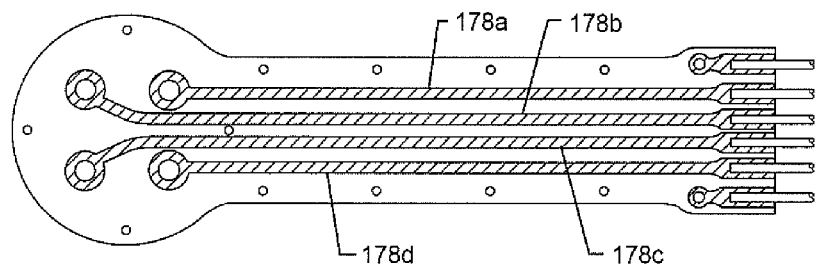
FIG. 42 is a sectional view taken along line 42-42 of FIG. 41.

FIG. 42 shows a cross sectional view generally taken from section 42-42 of FIG. 41 and shows the conductive circuit traces 178a through 178d.

Figure 43:
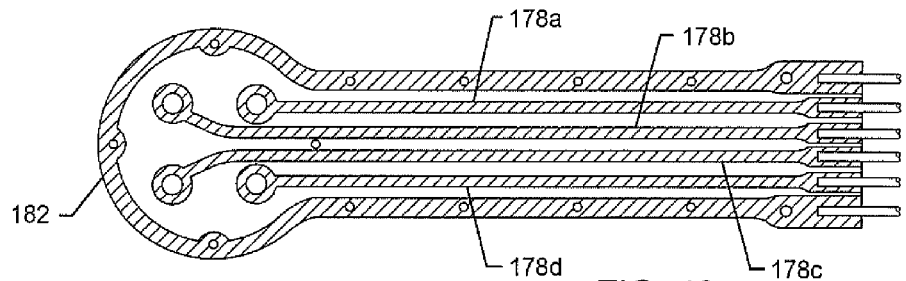
FIG. 43 is a sectional view taken along the line 43-43 of FIG. 41, illustrating an alternative to the internal circuit traces described with respect to FIG. 42.

FIG. 43 illustrates a cross sectional view generally taken from section 43-43 of FIG. 41 and shows an optional embodiment wherein a ground shield 182 surrounds the four circuit traces 178a through 178d.

Figure 44:
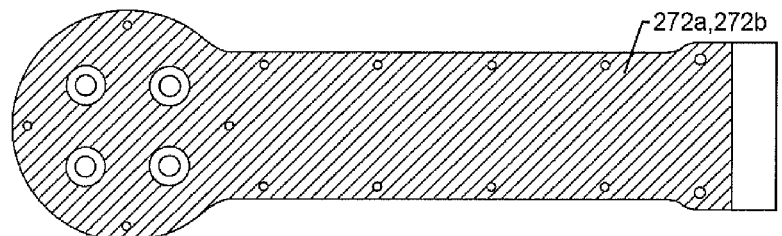
FIG. 44 is a sectional view taken along line 44-44 of FIG. 41, illustrating one of a pair of coaxially surrounding shields disposed about the circuit trace.

FIG. 44 is a cross sectional view taken generally from section 44-44 of FIG. 41 and illustrates shield layers 272a, 272b. These shield layers 272a, 272b are designed to surround each of the circuit trace layers 178 as previously described in FIG. 42 or 43. These shields 272a, 272b are not absolutely required, but greatly assist in preventing re-radiation of electromagnetic interference inside of the AIMD housing 124. This re-radiation of EMI can be very dangerous as it can couple to sensitive AIMD circuits and disrupt the proper functioning of the AIMD.

Figure 45:
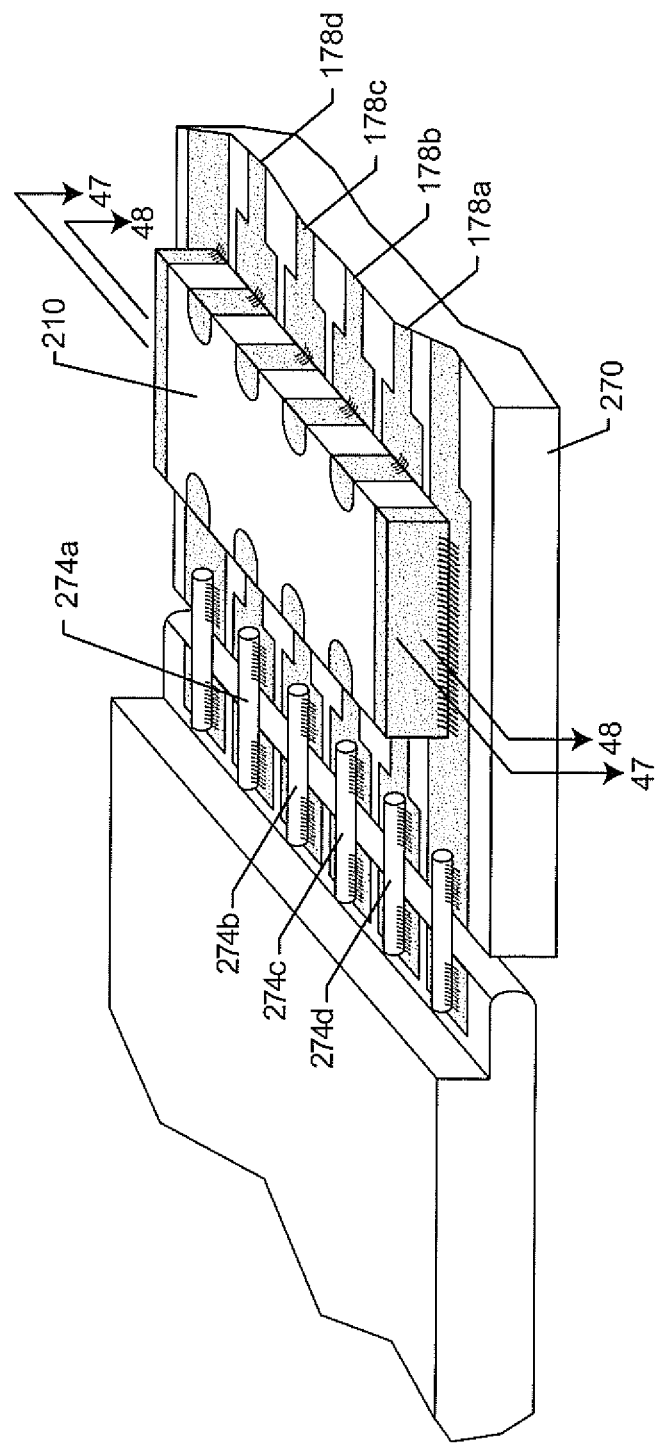
FIG. 45 is a perspective view of the flex cable of FIG. 41 connected to a circuit board or substrate having a flat-through capacitor.

FIG. 45 illustrates an embodiment in which the circuit traces 178*a* through 178*d* of FIGS. 41 through 44 are connected to a circuit board or substrate 270. Electrical attachments 274 are made to active circuit traces and in turn to a multi-element flat-through diverter capacitor 210. This three-terminal flat-through capacitor is very similar to that previously described in FIGS. 24 and 25 except that it has four capacitors embedded in a single structure. Capacitor 210 may replace the individual capacitor 210*a* through 210*d* as previously illustrated in FIG. 39 or capacitors 210*a* through 210*d* as previously described in FIG. 40.

Figure 46:
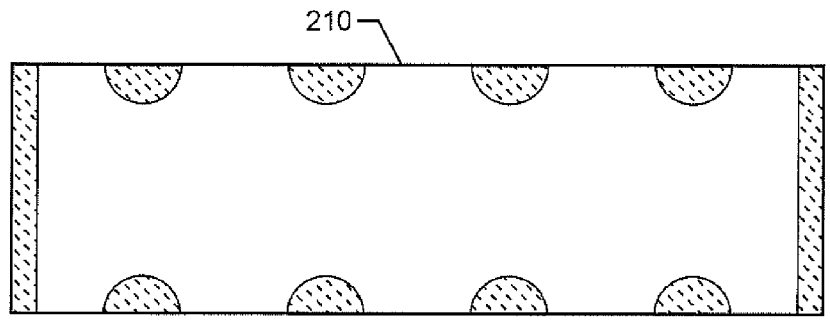
FIG. 46 is the top view of the flat-through capacitor from FIG. 45.

FIG. 46 shows a top view of the flat-through diverter capacitor 210 of FIG. 45.

Figure 47:
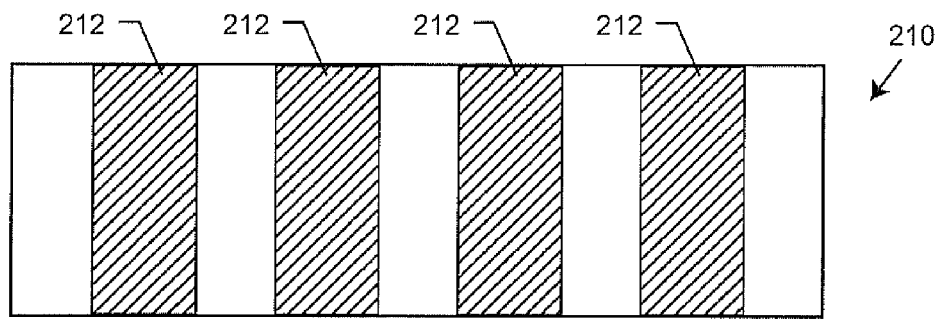
FIG. 47 illustrates the active electrode plates of the flat-through capacitor of FIGS. 45 and 46.

FIG. 47 is a cross sectional view taken generally from section 47-47 of FIG. 45 and shows the active electrode plates 212 of the flat-through diverter capacitor 219 of FIG. 45.

Figure 48:
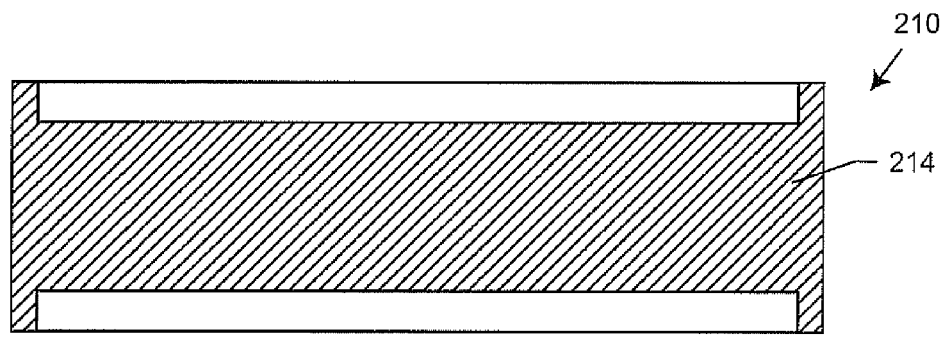
FIG. 48 illustrates the ground electrode plate set of the flat-through capacitor of FIGS. 45 and 46.

FIG. 48 is a cross sectional view taken generally from section 48-48 of FIG. 45 and shows the ground electrode plate 214 set of the flat-through capacitor 210 of FIG. 45.

Accordingly, from all of the foregoing it will be appreciated that this invention addresses the problems created when the radio frequency (RF) pulsed field of MRI couples to an implanted lead in such a way that electromagnetic forces (EMFs), voltages and current are induced in the lead. The amount of energy that is induced is related to a number of complex factors, but in general, is dependent upon the local electric field that is tangent to the lead and the integral electric field strength along the lead. In certain situations, these EMFs can cause currents to flow into distal electrodes or in the electrode interface with body tissue. It has been documented that when this current becomes excessive, that overheating of the lead or its associated electrodes can occur. In addition, overheating of the associated interface with body tissue can also occur.

There have been cases of overheated electrode damage to cardiac tissue which has resulted in loss of capture of cardiac pacemaking pulses. Furthermore, with respect to neuro-stimulators, neurological tissue damage severe enough to result in brain damage or multiple limb amputations have also been documented.

The present invention relates generally to methods and apparatus for redirecting RF energy to locations other than the distal tip electrode-to-tissue interface. In addition, the present invention provides electromagnetic interference (EMI) protection to sensitive active implantable medical device (AIMD) electronics. The redirection of this RF energy is generally achieved by the use of frequency selective devices, such as inductors, capacitors and filtered networks. As described in U.S. Pat. No. 7,689,288, to Stevenson et al., the contents of which are incorporated herein by reference, filtered energy dissipation networks can range from a single capacitor, such as a feedthrough capacitor, to more complex filters that may include L-C traps and/or L-C bandstop filters co-operating in various ways with C, L, Pi, T or n-element lowpass filters. In general, this is accomplished through frequency selective lowpass filters or series resonant LC trap filters wherein the RF energy can be redirected to another surface or is converted to heat. In all of the above described frequency selective networks, it is the capacitor(s) (co-operating with other circuit elements) which divert energy from an implantable lead conductor to the conductive housing 124 of an AIMD. The relatively large surface area of the AIMD housing 124 acts as an energy dissipating surface (EDS) wherein a significant amount of the MRI energy can be harmlessly dissipated without significant temperature rise. However, the lowpass filter also known as diverter capacitor elements must be designed to handle a very high amount of RF current and power. Accordingly, the capacitor's internal resistive or real losses known as equivalent series resistance (ESR) must be kept quite low. The present invention is directed to various embodiments of MRI diverter capacitor designs that minimize the diverter capacitor's equivalent series resistance (ESR). In addition, the capacitor is also designed to direct heat to relatively large surface area heat dissipation surfaces, thereby creating an efficient heat removal system. These high RF power/low ESR diverter capacitors are an important feature of the filter network of the present invention for diverting induced RF energy from an implanted lead conductor to an energy dissipating surface, particularly a conductive housing 124 of an AIMD.

These implantable lead systems are generally associated with AIMDs, such as cardiac pacemakers, cardioverter defibrillators, neurostimulators and the like. The present invention can also be incorporated with external devices, such as external pacemakers, externally worn neurostimulators (such as pain control spinal cord stimulators), catheters, probes and the like. It will be shown that for a given geometry constraint, a preferred means of reducing the diverter capacitor's ESR is to select the most ideal dielectric type so that its dielectric loss tangent (dielectric losses) is insignificant at the MRI RF pulsed frequency(ies). Of particular importance in the present invention is selection of a capacitor dielectric with the proper dielectric constant (k) value. The preferred capacitor dielectric will have a k of a sufficiently low value to thereby increase the number of active and ground electrode plates in the capacitor. This design feature dramatically reduces the ohmic losses in the capacitor at high frequency. Therefore, to accomplish a relatively high electrode plate count, a low k capacitor dielectric is used. A non-limiting example of one such dielectric material is an EIA standard, Class I dielectric material, COG, which is also known as NPO (negative-positive-zero). (Refer to EIA Standard ANSI/EIA-198-1-F-2002).

In general, at first glance, using a Class I dielectric is counterintuitive. For example, consider a typical X7R MLCC dielectric, with a dielectric constant of around 2500. With such a high efficiency dielectric material having a relatively high dielectric constant, it would be possible to build, for example, a 1000 picofarad filter capacitor with two to four electrode plates. Now consider using a Class 1 COG dielectric, wherein the dielectric constant is less than 100. A typical capacitor comprising the COG dielectric material would generally require greater than 20 or even 40 electrode plates to achieve the same capacitance value. Such a design would, however, provide a capacitor with a relatively large thickness and would also require significantly more precious metal in its manufacturing. A capacitor of this design is generally not desired.

Nonetheless, the benefit of incorporating a COG dielectric material within the capacitor design is generally a reduction of the capacitor's ESR at MRI RF-pulsed frequencies. If designed properly, the RF energy heat that is produced when positioned within an MRI scanner can be significantly reduced such that heat that results from RF energy does not pose harm to biological tissue.

One purpose of these low ESR diverter capacitors and related lowpass filter circuits is to provide electromagnetic interference (EMI) filtering in order to protect sensitive AIMD electronic circuits from malfunctioning in the presence of MRI RF noise. Another purpose of these circuits, as described in the present invention, is to draw MRI induced energy out of the lead and redirect said energy to the AIMD housing. This has the effect of reducing the energy that would reach the distal tip electrode or the interface with body tissue. By redirecting said energy to locations at a point distant from the distal electrodes, ideally the AIMD housing, this minimizes or eliminates hazards associated with overheating of said distal electrodes during diagnostic procedures, such as MRI.

For maximum RF energy transfer out of the lead, frequency selective diverter circuits are needed which decouple and transfer energy which is induced onto implanted leads from the MRI pulsed RF field to an energy dissipating surface. Importantly, while decoupling and transferring such energy, it is extremely important that the diverter circuits do not themselves overheat thereby creating hot spots on the AIMD housing, which could damage tissue, for example, in a pacemaker pectoral pocket. Recent experiments by the inventors have seen temperature rises from 4 to 10 degrees C. on the pacemaker housing directly over the location of the feedthrough capacitor during a 4 watt/kilogram MRI scan. In general, in the prior art, MLCC capacitors are really not indicated for high power RF applications. The reason for this is that the impedance (capacitive reactance) drops so low that extremely high RF currents end up flowing through the capacitor's electrode plates. During a 4 watt/kilogram MRI scan where 16 to 20 volts may be induced at the AIMD input, the diverter capacitor may be handling anywhere from 0.5 to 4 amps of RF current. If the ESR of the capacitor, for example, was 0.5 ohms and the capacitor was diverting 2 amps, then the $I^2R$ loss would be on the order of 2 watts. Two watts of dissipation on this small component would cause it to overheat significantly. The present invention fulfills these needs and provides other related advantages.

The RF diverting circuits, in general, conduct MRI induced RF energy from the lead or its associated lead wires to an EDS such as the housing 124 of the AIMD. The design of the diverter circuit is very important. First of all, the diverter circuit should appear as a very low impedance at MRI RF frequencies such that a maximum amount of RF energy is diverted from the lead conductor to the EDS. In addition, it is also desirable that the diverter element be designed such that it does not overheat.

Furthermore the mounting location of the diverter capacitor within an AIMD is also typically constrained by proper EMI design practices. Generally, EMI filters are designed such that undesirable RF energy is diverted at the point of lead ingress to the AIMD housing, as opposed to letting the EMI inside the AIMD housing and trying to filter it further downstream, such as on an internal circuit board. In a preferred embodiment, at least one of the low ESR diverter capacitors of the present invention is mounted directly to the multi-pin hermetic seal terminal of the AIMD. This is an ideal location both to divert RF energy before it can enter the AIMD housing but is also optimal for heat conduction and dissipation. Even with low ESR, the diverter capacitor will still be dissipating a significant amount of energy. This means, even with low ESR, the diverter capacitor is creating heat which must be conducted or convected away so that a hot spot does not occur on the AIMD housing at or near the filter capacitor. Therefore, by diverting both the RF energy and heat to the relatively large surface area of the housing of the AIMD the MRI RE energy can be dissipated with only a small temperature rise that does not adversely affect body tissue.

It should be pointed out that the general principle of placing the primary filter capacitor (energy diverter) at the point of leadwire conductor ingress in the AIMD housing is generally the preferred EMI design practice. For relatively low frequencies, such as an MRI RF pulsed frequency of 64 MHz, it would be perfectly acceptable to place the primary filter diverter capacitor on a circuit board remote from the hermetic terminal otherwise known as the point of leadwire ingress. In summary, having primary low ESR diverter capacitors only on a remote circuit board is not the optimal way to, at the same time, provide for high frequency filtering of AIMD electronics, but it would be acceptable for MRI compatible AIMDs, such as MRI conditionally approved pacemakers.

Figure 49:
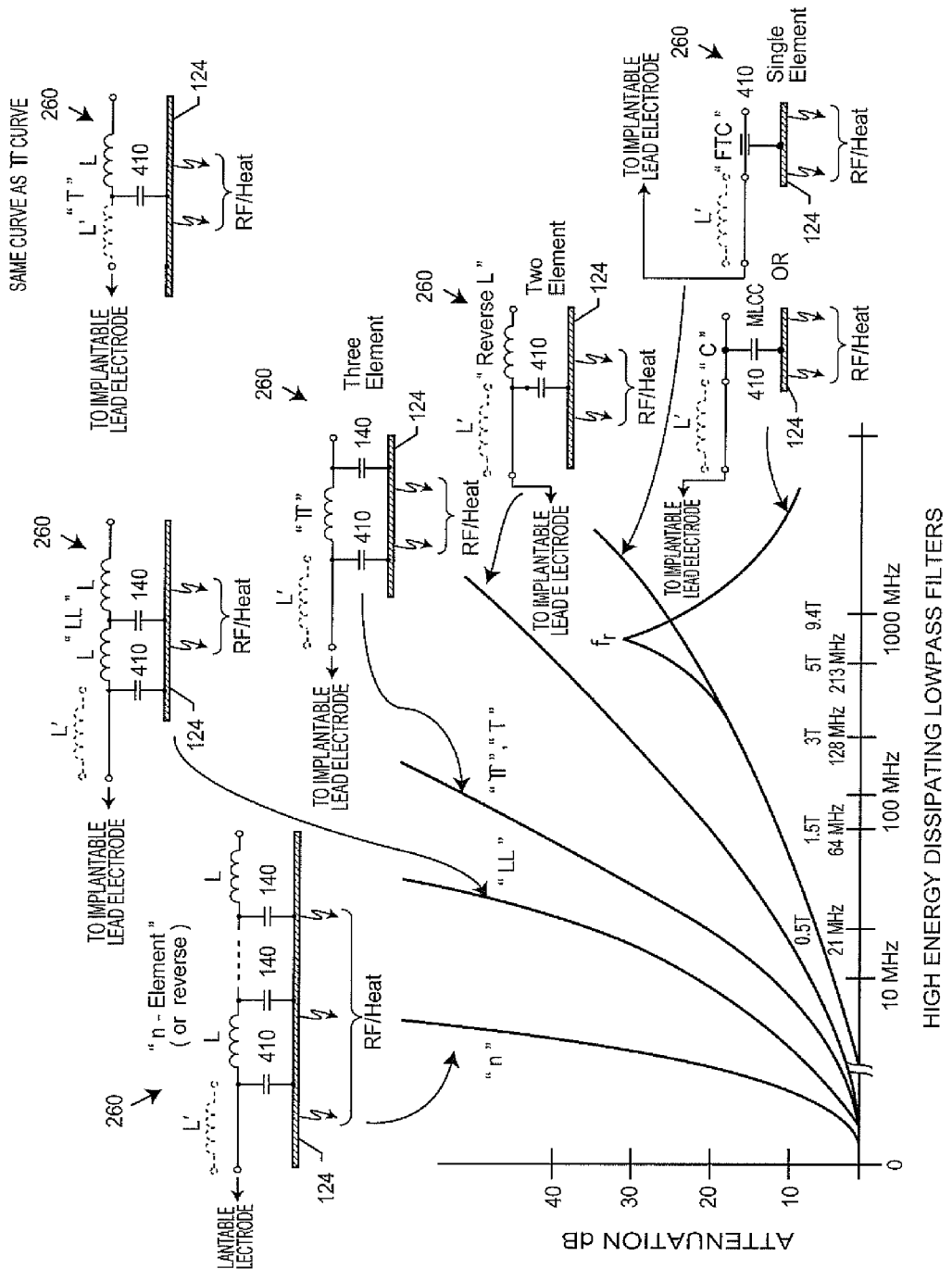
FIG. 49 illustrates a family of low pass filters, which is very similar to the family of low pass filters described in FIG. 37.

FIG. 49 illustrates a family of low pass filters, which is very similar to the family of low pass filters described in FIG. 37. Referring once again to FIG. 49, these are also known as EMI filters. This is because EMI filters are low pass filters, meaning that they allow low frequencies to pass and provide a substantial amount of attenuation to higher frequencies. In every one of the circuits of FIG. 49, there is a capacitor element 410 that is directed towards the implantable lead electrode (body fluid side). This is the path from an electrode, which is contacted with biological cells along the conductor of an implantable lead through the hermetic seal of the AIMD and along that same conductor, directly to capacitor 410. In accordance with the present invention, capacitor 410 must be a very high RF power, a low ESR handling capacitor so that the capacitor 410 and hence the AIMD will not overheat in an MRI environment. One will also note that the "n" element filter has been revised so that there is no longer an inductor directed toward the implanted lead electrode. The version of the LL filter, with the inductor directed to the implanted lead electrode has also been eliminated. In addition, the version of the 2-element or L filter, with the inductor toward the implanted lead electrode has also been eliminated. This is because, in the present invention, it is very important that the primary high power RF handling capacitor have a direct connection from its active electrode plates through the hermetic seal to the one or more electrodes of an implantable lead.

Referring once again to FIG. 49, for the n-element, LL and Pi (□) filters, one can see that there are two capacitors 410 and 140 separated by an inductor. In the present invention, it is critical that capacitor 410 have an ESR <0.5Ω at the MRI RF pulsed frequency and a dielectric constant <1000. This is in order that it have high electrode plate count and have a very low equivalent series resistance at MRI pulsed frequencies. The capacitor element 140 could be constructed of a low ESR construction the same as capacitor 410 or it could be constructed as prior art filter capacitors have been constructed in the past and that is with conventional ceramic dielectrics with a k>1000. Another way of looking at this is that the first capacitor directed toward the implanted electrode is the work horse and is going to do the bulk of the diverting of RF energy from the lead and diverting it to the AIMD housing where the energy and or heat could be dissipated over a large surface area.

The first EMI filter ever designed for an active implantable medical device was in the mid-1970s for the Xytron Medtronic pacemaker. These were unipolar feedthrough capacitor EMI filters that had a k of above 1200. The principle designer on this filter design project was Robert Stevenson, one of the co-inventors herein. The next EMI filter to be designed for cardiac pacemaker was in 1979 for a St. Jude pacemaker. Robert Stevenson worked with St. Jude Vice President Buehl Truex to design in this filter, which generally had a k above 2200. The inventors herein have spent their entire careers designing EMI filters for a variety of applications, including AIMD applications.

There has never been a case where the primary (work horse) passive EMI low pass filter has had a k below 1200. In addition, the inventors have either been asked to bid, have been aware of, or have cross-sectioned and analyzed explants of other manufacturer's EMI filters and have found the same thing to be true and that is, they have been built around a dielectric structure that has a k of at least 1200. For the last 30 years, almost all the primary EMI filters (the work horse filter) has been designed with a k of greater than 1200.

There are several reasons why the industry has always been at a k of about 1200 and generally above 2100 to 2200. The first important reason is that active implantable medical devices must be very small in size and very low in weight. Another consideration is cost. By using a high k dielectric, one needs fewer electrode plates and can build the capacitor much thinner and in a much smaller overall volume or footprint. This is ideal for all AIMDs, again where size and weight are critical. Until the MRI application came along, which this patent identifies, it was never contemplated to do what is completely counter-intuitive and that is to use a lower k capacitor.

The parent invention claims primary (work horse) passive diverter capacitors of less than 200 k. There is a general reason for this and that is the major material suppliers in the ceramic dielectric industries, such as Ferro offer dielectrics above 1200 k or below 200 k. The dielectrics below 200 k are known as Class 1 dielectrics. These Class 1 dielectrics find broad application in military and space applications that have never been used in the past for the primary EMI low pass filter capacitor for an AIMD. There is a vast desert in terms of material supply in the industry and that there are almost no suppliers of dielectric materials between 200 and 1000 k. There are a couple of specialty ceramic powder manufacturers, one of which is called Dimat, Inc. They offer a range of specialty dielectrics, including an N2200, which has a dielectric constant of 250; an N3300, which has a dielectric constant of 400; an N4700, which has a dielectric constant of 600; and, an N5250, which has a dielectric constant of 700. There is also another company called MRA Materials, which offers a dielectrics with a k of 485 and also a dielectric with a dielectric constant of 600.

First of all, none of the specialty or niche dielectrics have ever been used as the primary low pass EMI filter for an AIMD. The present invention claims that the primary EMI filter capacitor, which is directly connected through wiring to an implanted lead conductor with distal electrodes, be of less than 1000 k. There is a practical reason for this. In some cases, the capacitance value can be considerably high, such as 1800 pF. Building this capacitor out of a common commercially available dielectric, such as NPO (with a k of 90) results in a capacitor that has so many electrode plates that it becomes too thick to fit into the cardiac pacemaker. Accordingly, the inventor's developed an intermediate k dielectric (between 200 and 1000 k), which will present an ideal tradeoff between volumetric efficiency, a lower k, a higher number of electrode plates and accordingly, an ESR of less than 0.5 ohms that will meet all of the design criteria, including small in size, low in weight and low in cost.

In the embodiments herein, it is also possible to split the function of the primary or work horse diverter or low pass filter capacitor and break it up into two areas. One is referred to FIG. 39, which shows that the primary diverter capacitor can be broken up into two different capacitors, such as a feedthrough capacitor 210' and a board mounted capacitor 210. In a particularly preferred design, the capacitor 210 would have a dielectric constant of less than 1000 and even preferably less than 200. And for a needed capacitance value overall of 1800 pF, the high-energy, low ESR capacitor 210' could be 800 pF and the board mounted capacitors, which could be conventional technology with a dielectric constant above 1000, could be 1000 pF. These capacitors would add up in parallel to give 1800 pF, which is the design goal, but in this case, capacitor 210' is thinner thereby facilitating packaging between said capacitor and the circuit board structure. The values of 800 and 1000 pF are chosen at random and are not necessarily representative of any particular design. In other words, capacitor 210 could be 200 pF and capacitors 210a could be 1600 pF or any other possible combination one could imagine.

In summary, there has never been a primary filter (work horse) capacitor with a direct connection to the conductor of an implantable lead with an electrode in contact with body tissues ever built with a dielectric constant of less than 1000. It has been pointed out that one of the reasons for this is that designing a capacitor with a dielectric constant of less than 1000 is completely counter-intuitive for incorporation into AIMDs. It is only the advent of MRI compatible pacemaking systems and leads and the recent discovery that the primary filter capacitor itself can overheat and lead to excessive AIMD can (housing 124) heating when implanted in the human pocket that makes primary filter capacitors with a k less than 1000 suddenly an attractive design solution. This is because the dielectric constant of these capacitors when below 1000 leads to such a high number of electrode plates that the capacitor's ESR is so low that when the capacitor diverts (up to 6 amps) MRI RF frequencies, it will itself not overheat. The capacitor's ESR at high frequency is primarily an ohmic loss and given that all other electrical connections are solid, the ESR is largely correlative to the resistance of the electrode plate. When one increases the number of electrode plates, this ESR resistance drops significantly.

In the embodiments herein, the goal is to drop ESR so much that insignificant heat is produced by the filter capacitor itself so that undue AIMD implant pocket heating does not occur. The FDA and the industry generally limit implant pocket heating to about 4 degrees Centigrade. It has been demonstrated by the inventors that the combination of overheating of prior art primary low pass filter capacitors with a k greater than 1200 can by themselves result in the AIMD housing and the corresponding human pocket overheating significantly above 4 degrees C. The herein disclosed embodiments solves that problem and has other related advantages.

Referring once again to FIG. 37, there is an inconsistency between the "LL" and "reverse LL" as compared to the "L" and "reverse L." Referring to the LL filter, one can see that there is a capacitor 210 on the left side of the circuit. For the reverse LL, there is an inductor on the left side of the circuit. This is somewhat inconsistent with the teachings of the L filter wherein, the inductor is first directed to the left side (as opposed to the capacitor 210 for the LL configuration). For the reverse L filter, capacitor 210 is directed to the left. There really is no industry standard on what constitutes a reverse L or a reverse LL. In fact, when manufactured, they could be installed by the user in either direction, which would further confuse the issue. Accordingly, in the present invention, it is shown both ways to indicate that there really is no standardization between the words LL and reverse LL or L and reverse L. The reference in the claims to the LL, the reverse LL, the L and the reverse L filters refer to the specific electrical schematic shown in FIGS. 37 and 49 and also in other detailed schematic drawings.

Referring once again to FIG. 49, one will see that for the single element capacitor, it can be a two-terminal device 410 "C" or a single element feedthrough capacitor "FTC." It will be understood by those skilled in the art that any of the capacitors 410 shown in FIG. 49, could be two-terminal capacitors or feedthrough capacitors "FTC."

Referring once again to FIG. 49, one can see that the insertion loss versus frequency curve for the three-terminal feedthrough capacitor of FTC does not have a significant resonant dip versus frequency. However, when one refers to the insertion loss curve for a single element MLCC chip capacitor 410, one can see that it has a significant self-resonance $f_r$ as shown. This resonant frequency $f_r$ is because in the capacitor equivalent circuit, as previously shown in FIG. 25, the MLCC chip capacitor has significant equivalent series inductance 204. When a capacitor has equivalent series inductance, there is always going to be some frequency at which the capacitive reactance is equal and opposite to the inductive reactance. This is known as the capacitor's self-resonant frequency. One can see that there is an insertion loss peak at the capacitor's self-resonant frequency $f_r$. This would go to infinity if it were not for the capacitor's equivalent series resistance. In other words, this would go to infinite attenuation in dB if not for the capacitor's equivalent series resistance (ESR). The problem for the MLCC capacitor occurs at frequencies above its self-resonant frequency $f_r$. At higher frequencies, above the self-resonant frequency, the inductive reactance becomes increasingly dominant, which undesirably reduces the filter attenuation in dB. Well mounted feedthrough capacitors tend to have essentially zero equivalent resistance 204, as shown in FIG. 25 and therefore, have a more ideal filter response curve versus frequency.

Figure 49A:
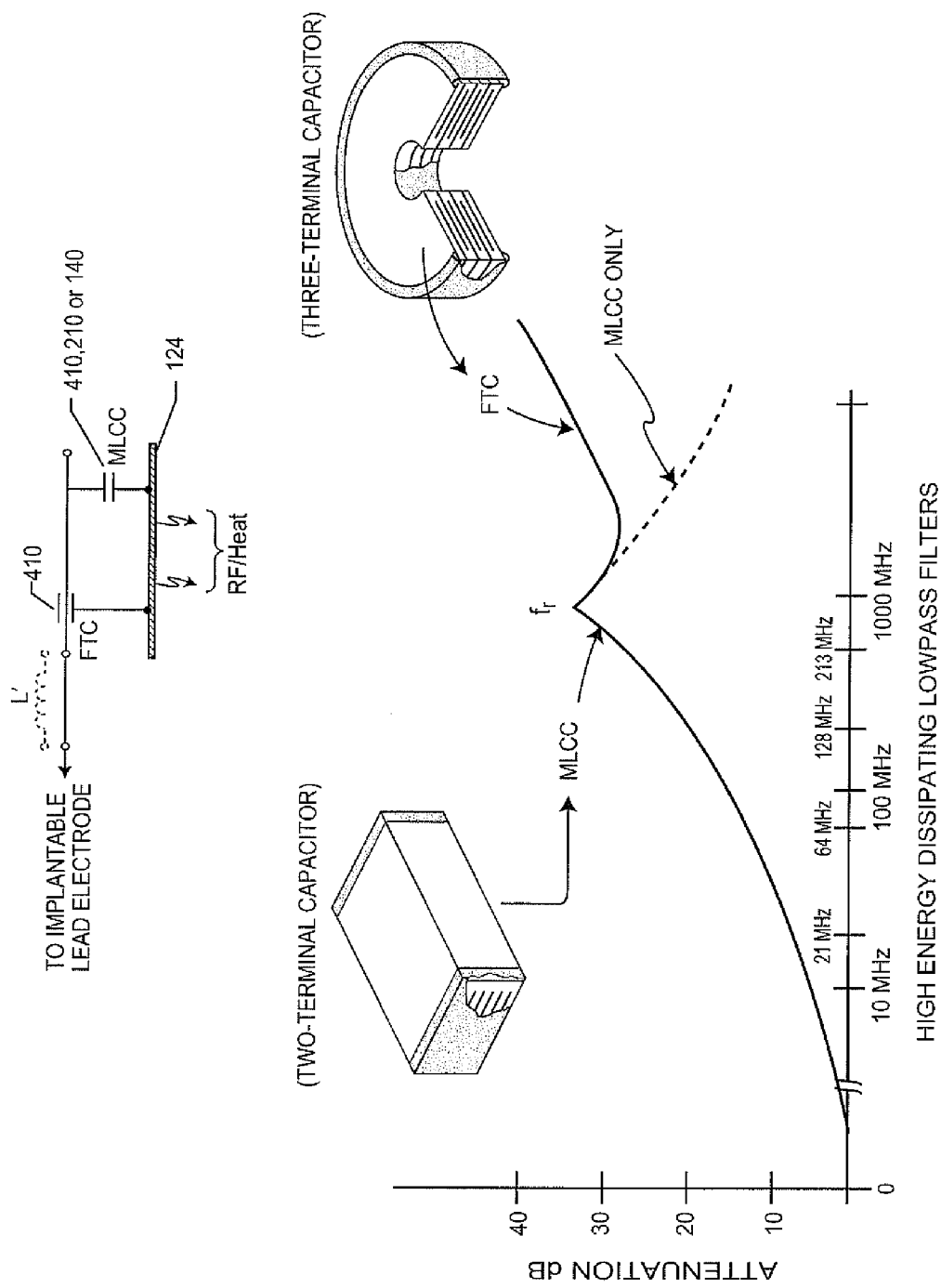
FIG. 49A is similar to FIG. 49 now showing the attenuation curve for a feedthrough capacitor with chip capacitor.

FIG. 49A reads on FIG. 39 and FIG. 39A, In FIG. 39, it was described that one could split up the primary filter capacitance into a feedthrough capacitor 210' and a board-mounted capacitor 210a. Referring once again to FIG. 49A, the schematic diagram is redrawn showing a feedthrough capacitor 410 in accordance with the present invention wherein, the feedthrough capacitor has a k<1000 and extremely low ESR properties (an ESR of <2 ohms at the MRI RF-pulsed frequency). The circuit board-mounted MLCC chip capacitors (410, 210, 140) are shown in parallel with the primary feedthrough capacitor 410. The MLCC chip capacitor 410, 210 or 140, can have a k of <1000 in accordance with the present invention (410), can have a k<200 (210) or be a prior art MLCC capacitor having a k>1000 (140). Also shown in FIG. 49A is the composite insertion loss curve of the feedthrough capacitor in parallel with the MLCC chip capacitor. One can see what would happen if we only have the MLCC capacitor as shown as a dashed line. However, the feedthrough capacitor having zero series inductance picks up the degradation and insertion loss that would occur from the MLCC only and therefore provides an overall/combined broadband low pass filter performance which is ideal for an EMI filter and an MRI filter.

Referring back again to FIG. 49, one can see that each one of the low pass filter circuits has a phantom inductor L' drawn with dashed lines. This is in order to recognize that all conductors have some amount of series inductance and that some amount of inductance will be in series between the primary work horse capacitor 410 and the distal lead conductor electrode. It is very desirable in the present invention that this inductance L' be kept as low as possible. If this inductor became too large, then a large inductive reactance would occur at MRI RF-pulsed frequencies, thereby reducing the amount of energy that could be pulled from the lead. In other words, it is desirable that the first thing that is connected to the implantable lead electrode along the path of the implantable lead electrode be the work horse capacitor 410 so that it can draw maximal energy out of the lead. It is also critical that this work horse capacitor 410 be very low in ESR so that it does not overheat while drawing literally amps of MRI induced energy out of the lead system. Many implantable leads themselves are made of spiraled or of coiled construction. Some of these are insulated and some of these are not insulated. The uninsulated lead conductors tend to short together, particularly when going through torturous paths, such as bends in a venous system. Therefore, their parasitic conductance will vary significantly due to design and lead trajectory differences. In summary, the phantom inductors L', shown in FIG. 49, simply acknowledge that some parasitic inductance can be associated with the direct connection of the primary work horse capacitor 410 and a distal electrode. It is particularly important that the parasitic inductance be minimized from the point of leadwire ingress into the AIMD housing. That is, from the conductor that passes through the hermetic seal insulator in non-conductive relation, it is very important that there be very little inductance or insignificant parasitic inductance between the work horse capacitor 410 and that point of leadwire penetration into the AIMD housing.

Figure 50:
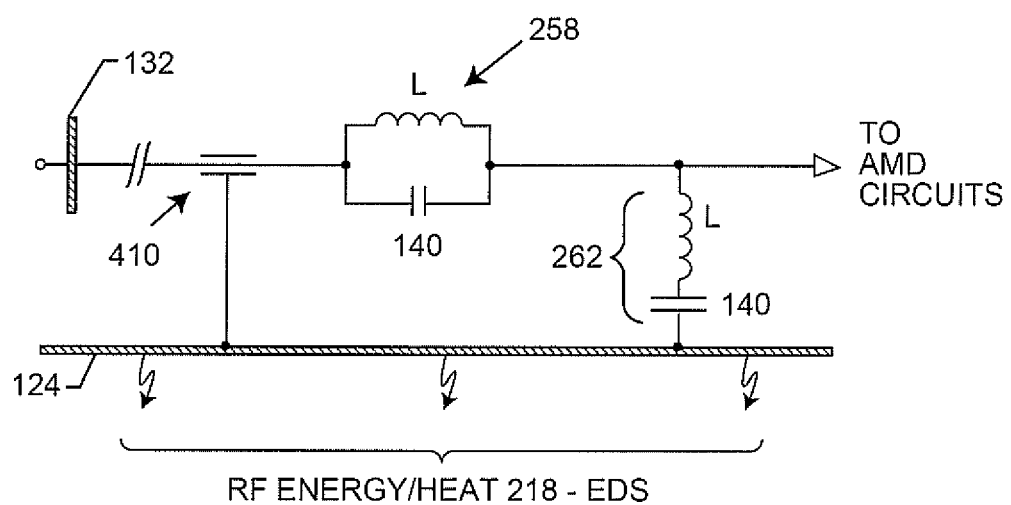
FIG. 50 illustrates that the high energy dissipating low ESR capacitor can be used in combination with other circuits.

FIG. 50 illustrates that the high energy dissipating low ESR capacitor 410 can be used in combination with other circuits, such as bandstop filter 258 and L-C trap filter 262 consisting of capacitor 140 and inductor L. Again, the capacitor of a bandstop filter 258 and the capacitor 140 of the L-C trap can be conventional prior art filter capacitors. However, capacitor 410 is the work horse and must be very low in ESR in accordance with the present invention.

Figure 51:
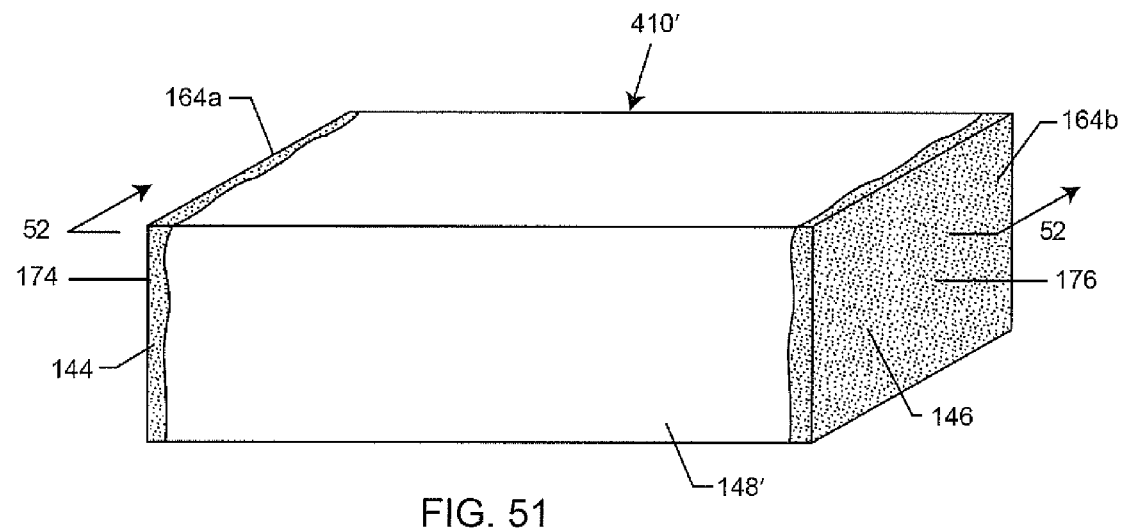
FIG. 51 shows a perspective view of an MLCC capacitor that is similar in its exterior appearance to the prior art MLCC capacitor previously described in FIGS. 14 and 15.
Figure 52:
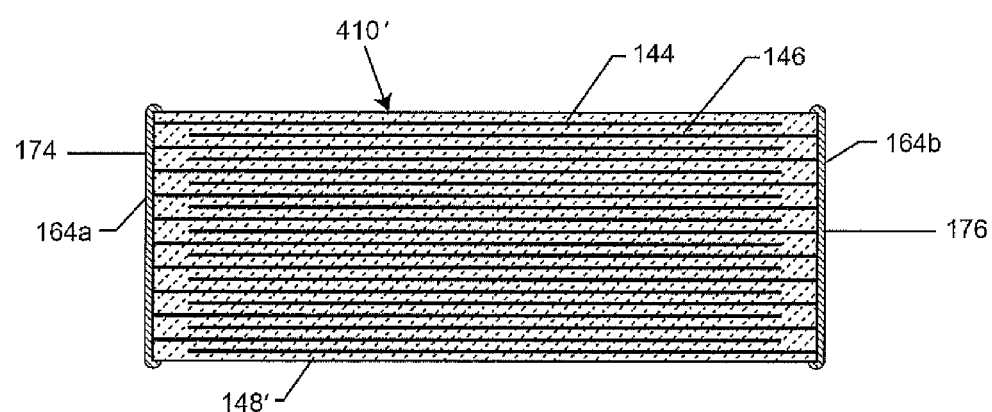
FIG. 52 is a sectional view taken along lines 52-52 of FIG. 51.
Figure 53:
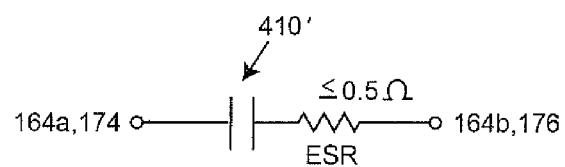
FIG. 53 is the electrical schematic representation of FIGS. 51 and 52.

FIG. 51 and FIG. 52 shows an MLCC capacitor that is similar in its exterior appearance to the prior art MLCC capacitor previously described in FIGS. 14 and 15. In accordance with the present invention, the MLCC capacitor of FIGS. 51 and 52 has a k<1000 and an ESR of <0.50 at the MRI RF-pulsed frequency. Also, in accordance with the present invention, it has a relatively high number of active and ground electrode plates 144, 146 compared to the prior art chip capacitor previously illustrated in FIGS. 14 and 15. FIG. 53 is the electrical schematic of FIGS. 51 and 52 showing in that a preferred embodiment the ESR is less than 0.5 Ohms.

Figure 54:
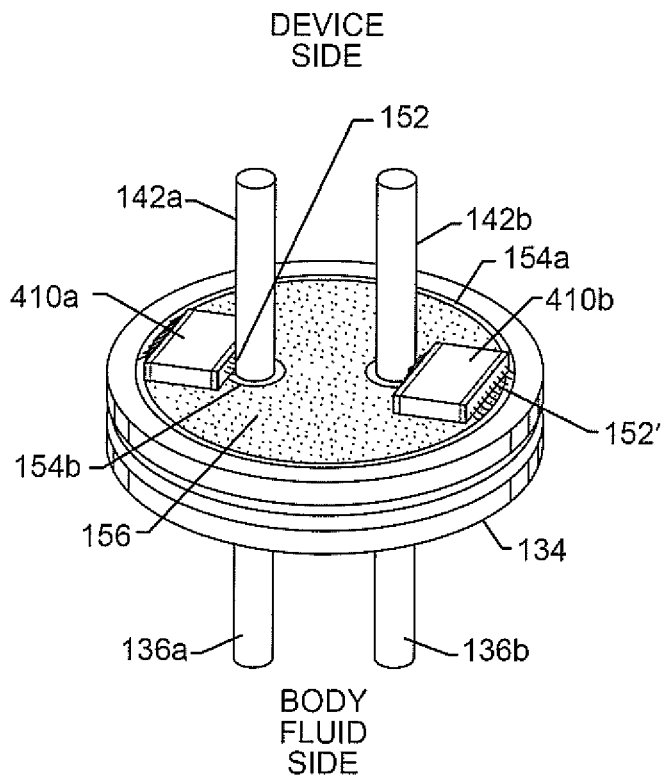
FIG. 54 is a bipolar hermetic seal having a ferrule and two leads passing through the conductive ferrule in insulative relationship.
Figure 55:
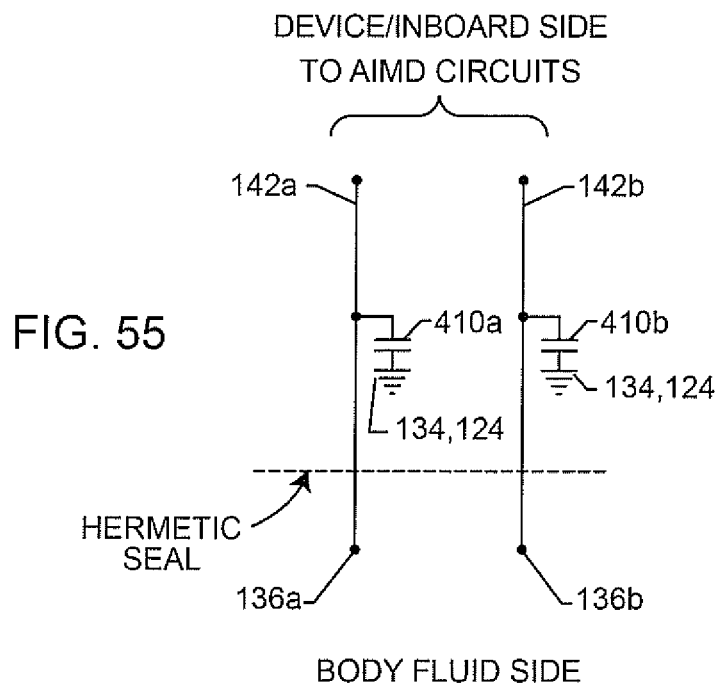
FIG. 55 is the electrical schematic representation of FIG. 54.

FIG. 54 is a bipolar hermetic seal having a metallic ferrule 134 and two leads 142a and 142b passing through the conductive ferrule in insulative relationship. There are two MLCC chip capacitors 410a and 410b, as previously illustrated in FIGS. 51 and 52. These chip capacitors are electrically connected between each one of the respective leads and to the ground of the ferrule. Shown is an attachment to a gold bond pad/braze 154a on the ferrule in order to provide an oxide free and very low resistance electrical connection to the titanium ferrule 134. This is more thoroughly described in U.S. Pat. No. 6,765,779, the contents of which are incorporated herein by reference. FIG. 55 is a schematic diagram of the bipolar filtered hermetic terminal of FIG. 54.

Referring now back to FIG. 19, one will appreciate that the MLCC capacitors of FIGS. 51 and 52 of the present invention could also be adapted to the substrate 147. That is, the chip capacitors could be mounted on the circuit board or substrate, which is then mounted to the hermetic terminal adjacent to the ferrule and/or insulator. Such circuit boards and substrates could be mounted immediately adjacent to the terminal or adjacent the hermetic terminal or even at a remote location.

Figure 56:
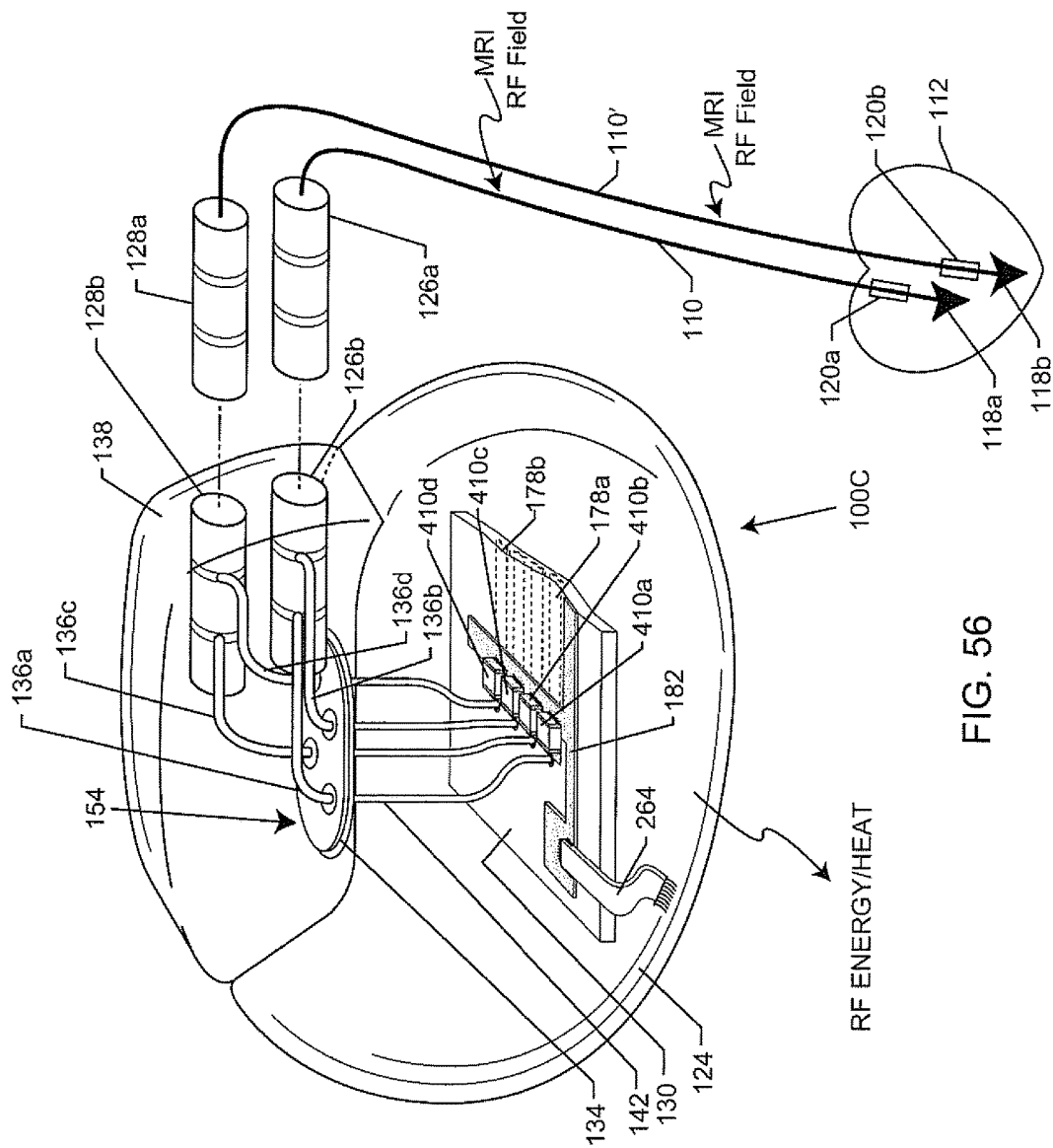
FIG. 56 is similar to FIG. 6 showing a breakaway cross-section of a typical AIMD with novel capacitors mounted to an internally disposed circuit board.

FIG. 56 is similar to FIGS. 6 and 39 showing a breakaway cross-section of a typical AIMD, such as a cardiac pacemaker. Referring back to FIG. 6, one will see that there is a typical prior art feedthrough capacitor 140 shown adjacent the ferrule of the hermetic terminal 134. As described herein, prior art feedthrough capacitors 140, for primary EMI filtering of AIMDs, have always been built from dielectric materials >1000 k.

FIG. 56 shows a circuit board 130 similar to the circuit board 130 previously illustrated in FIG. 6. However, in this case, there is a quadpolar hermetic terminal 154 and there are four MLCC chip capacitors 410a through 410d. These chip capacitors are low ESR chip capacitors in accordance with FIGS. 51 and 52. In accordance with the present invention, these extremely low ESR chip capacitors will draw a great deal of RF energy from the implanted lead when it is in an MRI environment. It is important that this RF energy be efficiently dissipated to the AIMD housing 124 where it can be dissipated as RF energy and heat. One will notice that there is a wide low inductance ground circuit trace 182. Therefore, between each one of the quadpolar leads 136, there is an MLCC chip capacitor connected to ground. This efficiently diverts RF energy from the lead conductors 136 to the ground circuit trace 182. There is an RF grounding strap 264 shown which is relatively wide compared to its width. This greatly reduces the inductance and makes it more efficient at high frequencies for diverting the RF energy to the AIMD housing 124. In general, in another embodiment, the width of the strap will be >4 times its thickness.

Figure 56A:
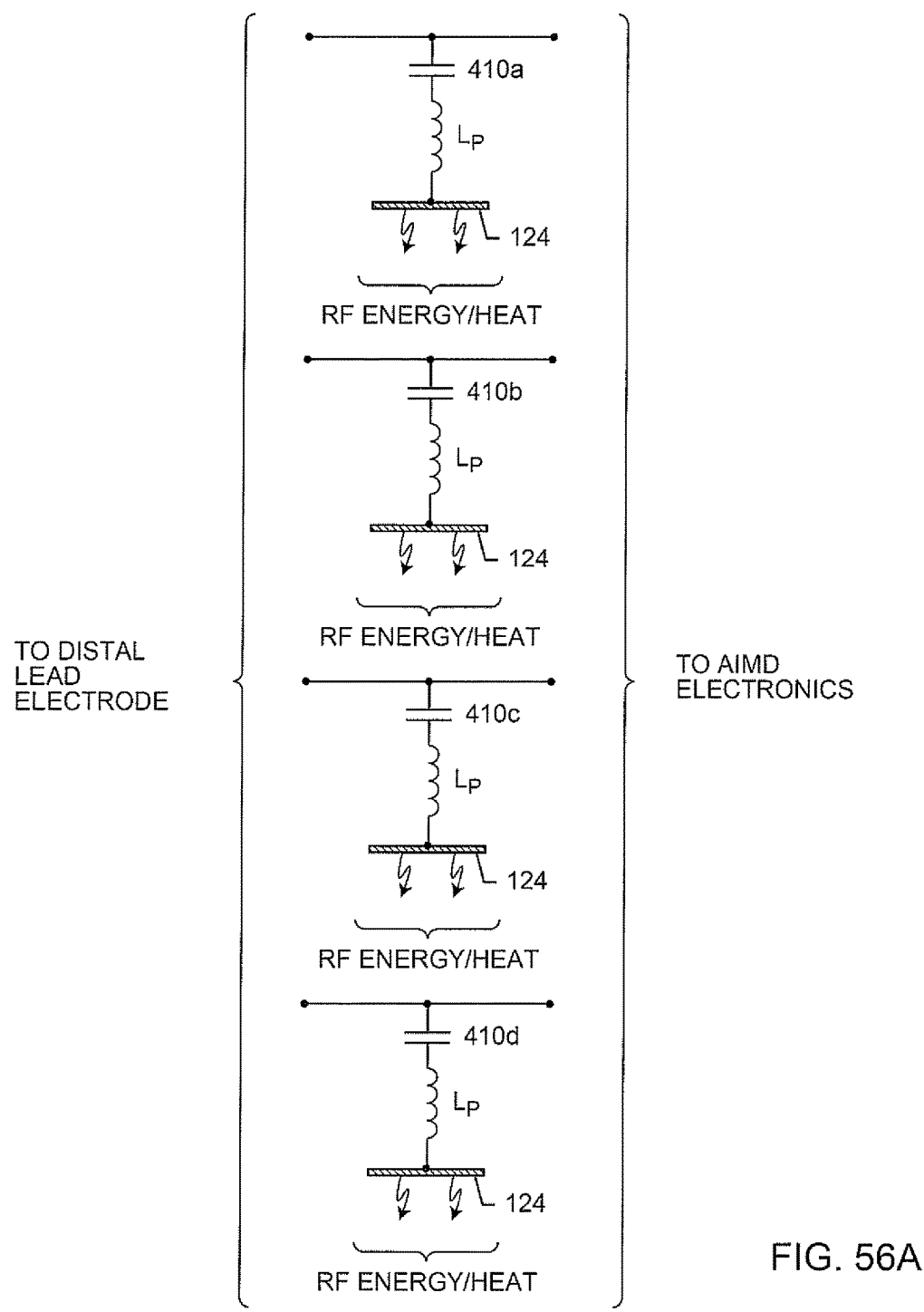
FIG. 56A is the electrical schematic of FIG. 56.

FIG. 56A is a schematic diagram of the MLCC primary work horse filters illustrated in FIG. 56. Shown are the work horse low ESR capacitors 410a through 410d. In series with each one of these capacitors is shown a parasitic inductance Lp. This inductance results from the inductance of the leadwire from the length of the leadwire from the point of leadwire ingress through the hermetic seal to the circuit board connection to the capacitor 410. It also includes the inductance of the circuit trace 182 and the ground strap 264. It is desirable to keep this parasitic inductance as low as possible. That is why the circuit traces 182 are relatively wide and the ground strap 264 is relatively wide. It is also important to minimize the inductance of the lead between the hermetic seal and the active end (non-ground end) of the primary filter capacitors 410. This could be done by making the wire shorter, larger in diameter or flat/rectangular or a combination of all of the above.

Referring once again to FIG. 56, one can see that the leadwires 136 are directed to via holes in the multilayer of circuit board 130. There is a metallization about the via hole to which the capacitors 410a through 410d are attached on the left side (or active electrode side). The leads pass through the via in the circuit board 130 to another layer where they contact active circuit traces, which are shown as dashed lines (hidden lines). This completes the circuit from the leadwires 136 underneath the primary filter capacitors 410 and underneath the ground circuit trace 182 where they connect to other via holes (not shown). These not shown via holes would be connected to other AIMD electronics, such as an ASYC electronics chip or the like.

Figure 57:
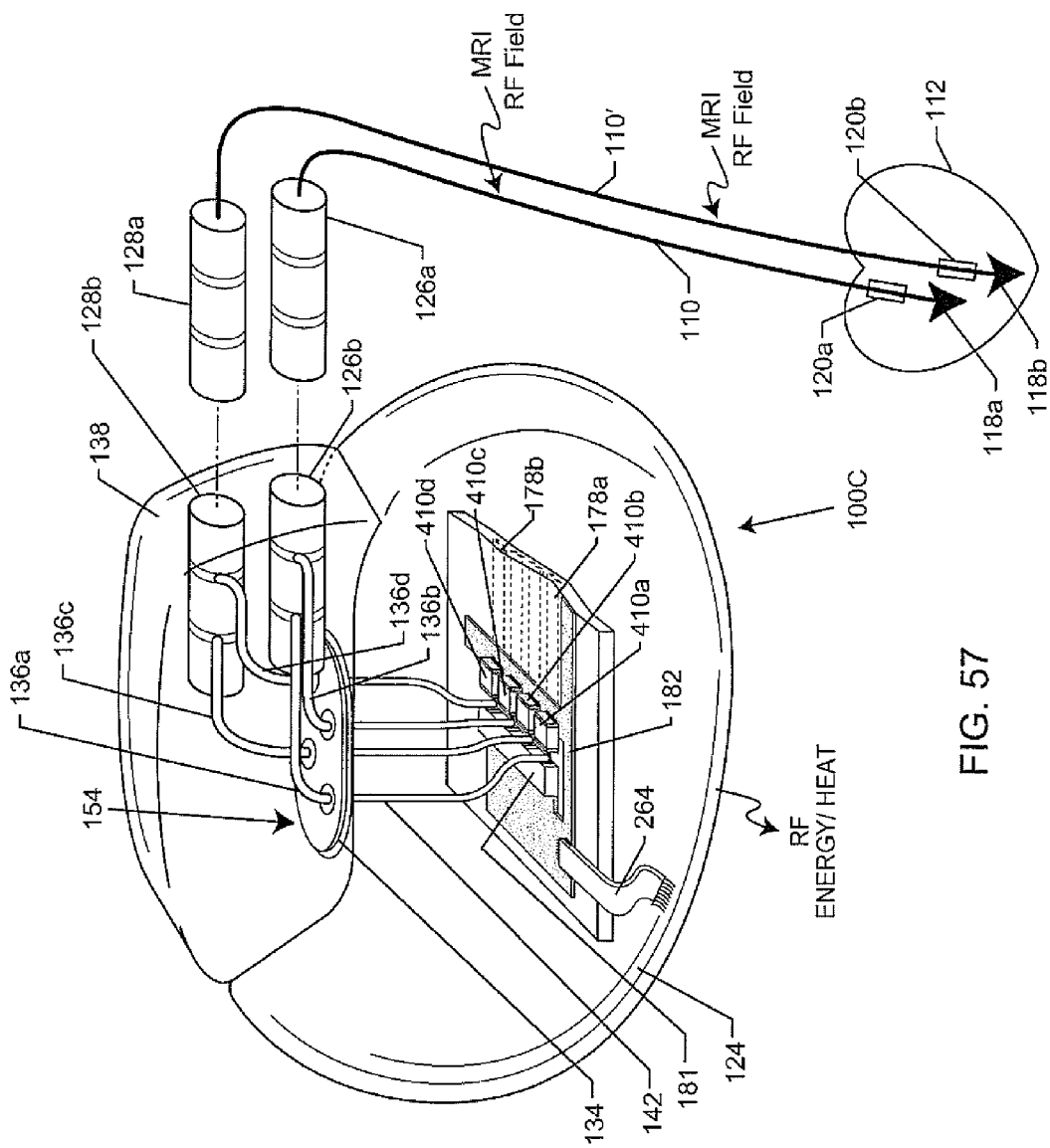
FIG. 57 is very similar to FIG. 56 except that a diode array has been added.

FIG. 57 is very similar to FIG. 56 except that a diode array 181 has been added. It is very common in the input circuitry of AIMDs to provide an overvoltage diode protection array mainly against the use of automatic external defibrillators (AEDs). AEDs can induce a very large high voltage pulse into implanted leads and this high voltage can be undesirably directed toward sensitive AIMD electronic circuits. The diodes protection pack 181 provides high voltage over protection between each one of the quad polar leads 136 and to ground or AIMD housing 124.

Figure 58:
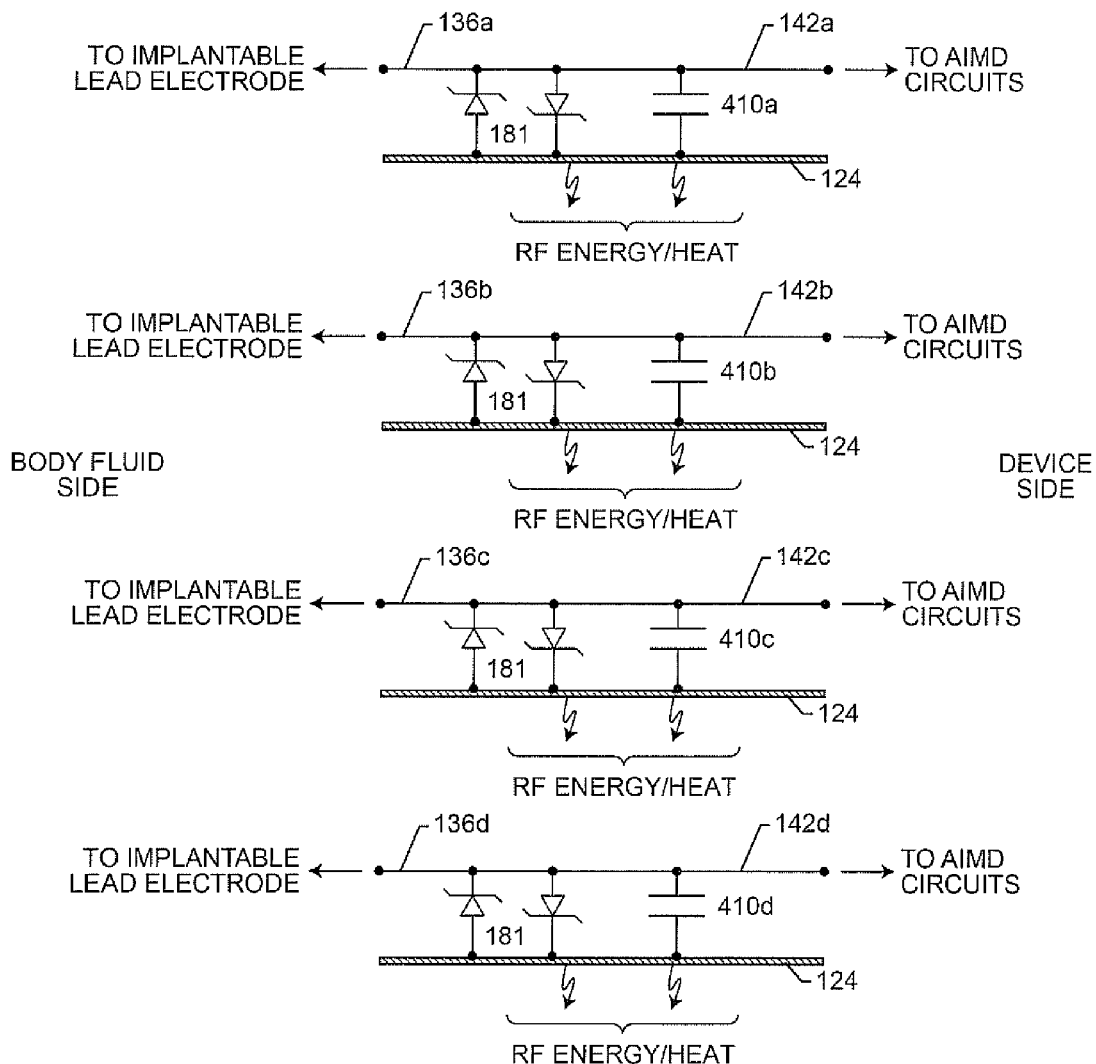
FIG. 58 is the electrical schematic representation of FIG. 57.

This is better understood by referring to the schematic diagram of FIG. 58 which represents FIG. 57. One can see that there still is a continuous electrical circuit connection 136a to 136d from the low ESR high RF-energy dissipating capacitors 410a through 410d of the present invention. Again, in each case the capacitor 410 remains the work horse as the primary diverter of high frequency MRI RF energy to the case housing 124. Note that the circuit ground symbols in FIG. 57 are all connected to the AIMD housing 124 through ground strap 264.

Figure 59:
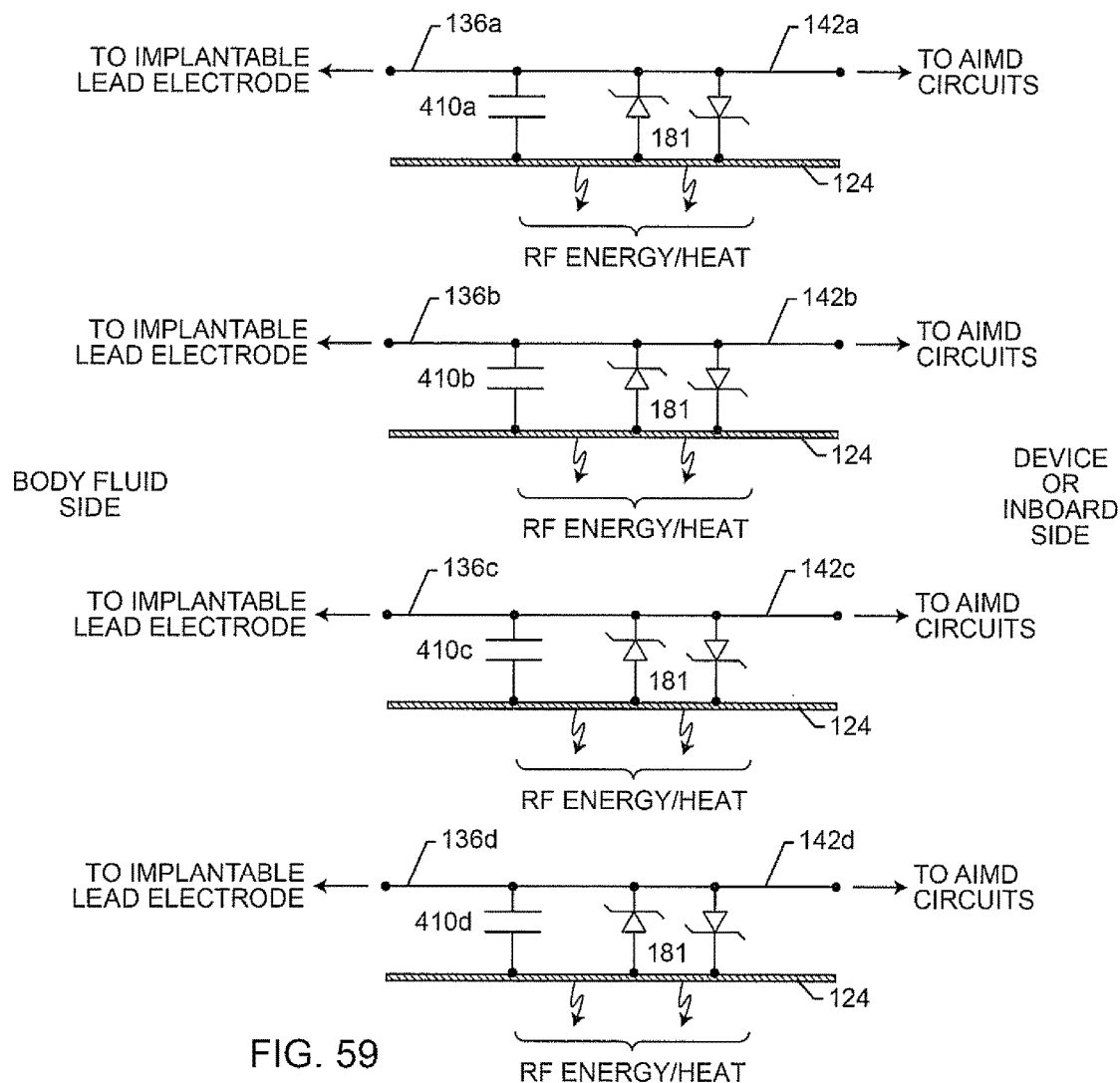
FIG. 59 is very similar to FIG. 58 except the high voltage protection diode array is shown on the other side of the low ESR capacitors.

FIG. 59 is very similar to FIG. 58 except the high voltage protection diode array is shown on the other side of the low ESR capacitors 410 of the present invention. Since the high voltage protection capacitors are not in series, but in fact in parallel, it would be well known to any electrical engineer that they could be placed anywhere along the length of the conductors 136a-d. In either case, or in all of these cases, the low ESR capacitor of the present invention 410 is always directly connected by way of continuous circuit pads through the hermetic connector all the way through a lead conductor through to an electrode that is contactable to biological cells.

Referring once again to FIG. 58, one will notice that the back-to-back diodes 181 can clamp and shunt a positive or negative polarity pulse. For AEDs, it is common that there would be a biphasic pulse, meaning that the pulse would switch polarity. Therefore, it is common practice to orient the diodes back-to-back 181 so that may shunt energy with both positive and negative polarities. The diodes in the primary EMI low ESR protection capacitor 410 also rule out the possibility of placing any electronic chips, active filters or other sensitive electronics in this portion of the circuit path. These are the very components that would be damaged by an over voltage or interfered with by EMI. So in general, these sensitive AIMD circuits are always downstream (to the right) of FIG. 58.

Figure 60:
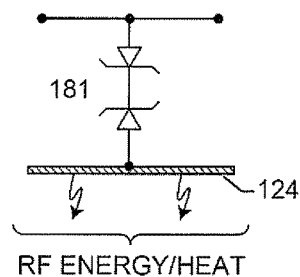
FIG. 60 is an electrical schematic of a back-to-back diode placed in series taken from lines 60-60 of FIG. 59.

FIG. 60 is taken from section 60-60 taken from FIG. 59. FIG. 60 illustrates that instead of two discrete separate diodes 181 that are wired back-to-back, they also can be placed back-to-back in series as shown in FIG. 60. Sometimes these are called Transorbs®. In general, these diodes can be any type of transient voltage suppressor, varistors, avalanche diodes or Zener diodes.

Figure 61:
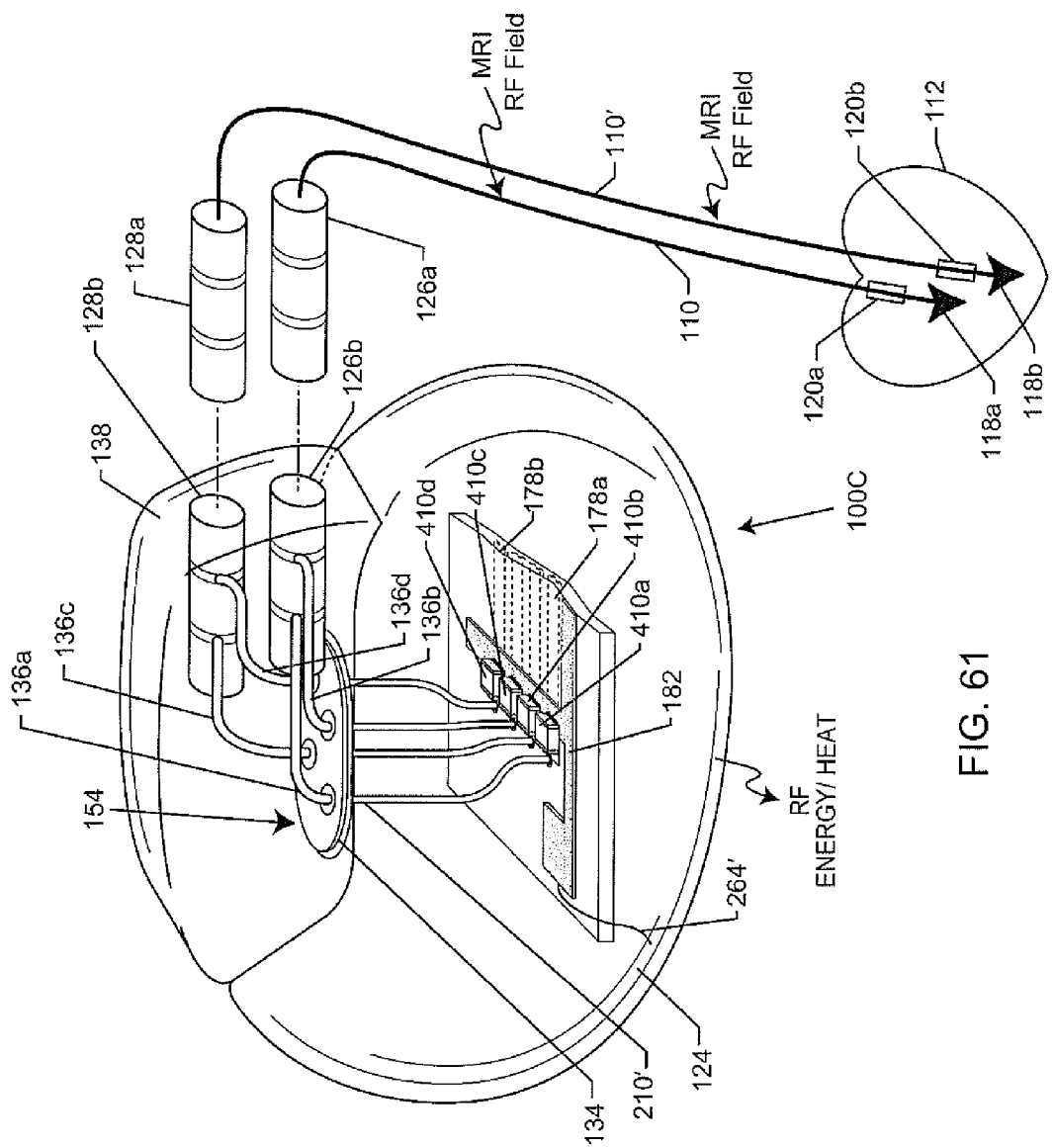
FIG. 61 is very similar to FIG. 56 except that the RF grounding strap has been replaced with a simple leadwire connection.

FIG. 61 is very similar to FIG. 56 except that the RF grounding strap 264 has been replaced with a simple leadwire connection 264'. This would work okay at relatively low RF frequencies. For example, for a 1.5 Telsa scanner, the RF-pulsed frequency is 64 MHz. Then as scanners have evolved to higher and higher frequencies, the inductance of such a small wire could become problematic. For example, there are many modern scanners in the market operating at 3 Tesla, which means that the RF frequency is 128 MHz. The inductive reactance is equal to 2×π×frequency×inductance. So if the inductance is small and the frequency is large, one can get a great deal of inductive reactance which would make the diversion of high frequency energy through the primary low ESR chip capacitors 410 less efficient. Another way of saying this is you really don't want anything in the ground path that would impede diverting the high frequency RF energy to the AIMD housing 124. One way around this (not shown) would be to use multiple leadwires 264' thereby creating additional circuit paths to ground and thereby reducing the inductance.

Figure 62:
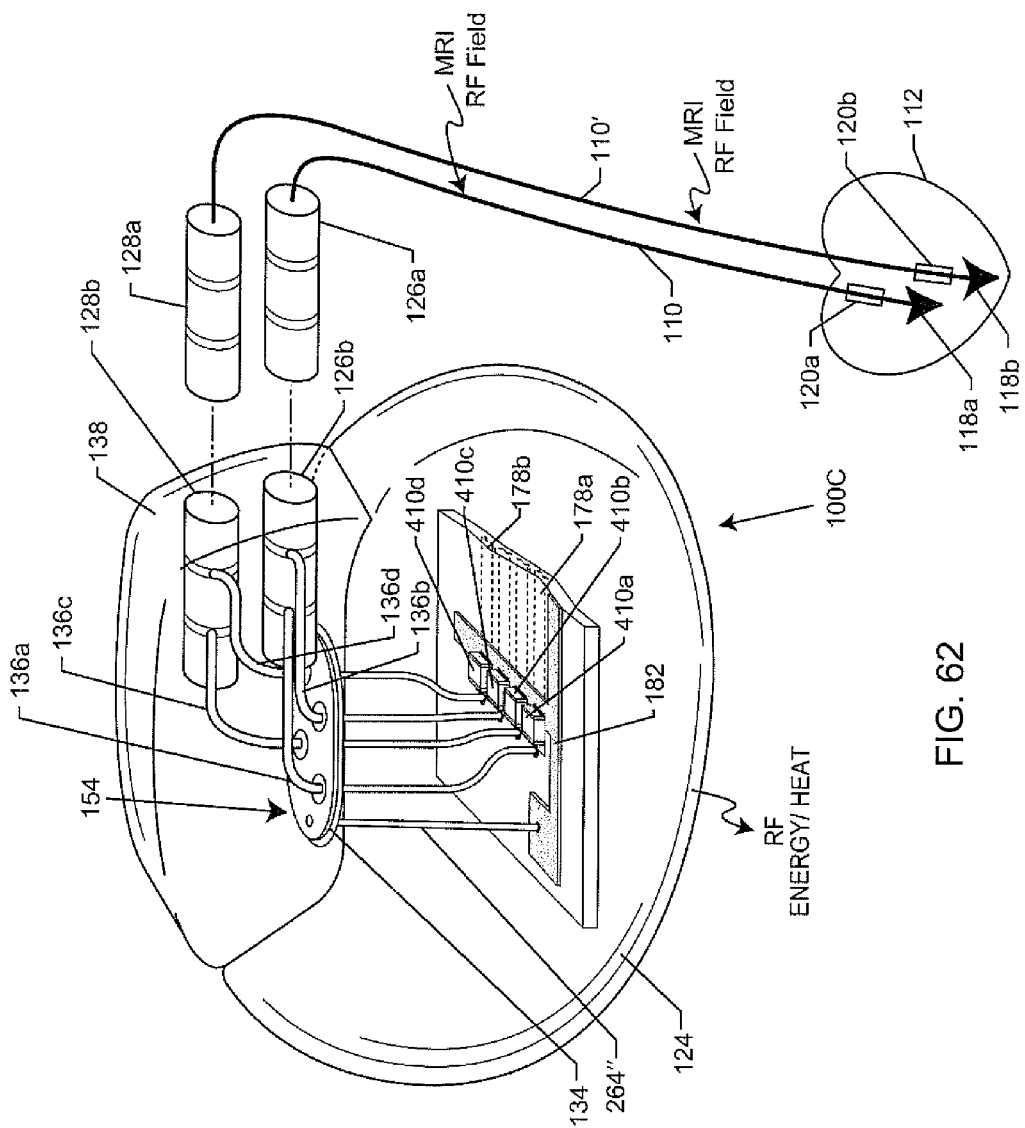
FIG. 62 is very similar to FIG. 61 now with the grounding leadwire routed directly to the ferrule of the hermetic terminal subassembly.

FIG. 62 is very similar to FIG. 61 except in this case, the grounding leadwire 264" could be routed directly off the ferrule 134 of the hermetic terminal subassembly.

Figure 63:
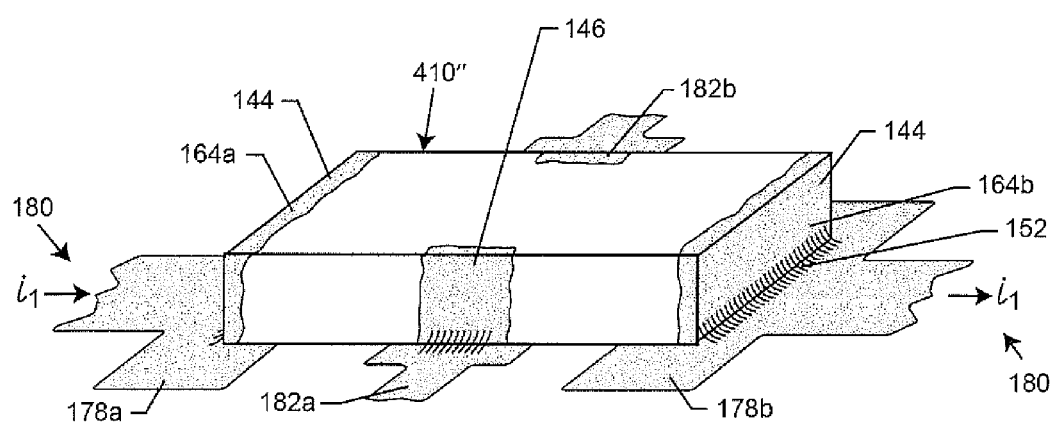
FIG. 63 is very similar to prior art FIG. 17 that illustrated a flat-through type of feedthrough capacitor.
Figure 64:
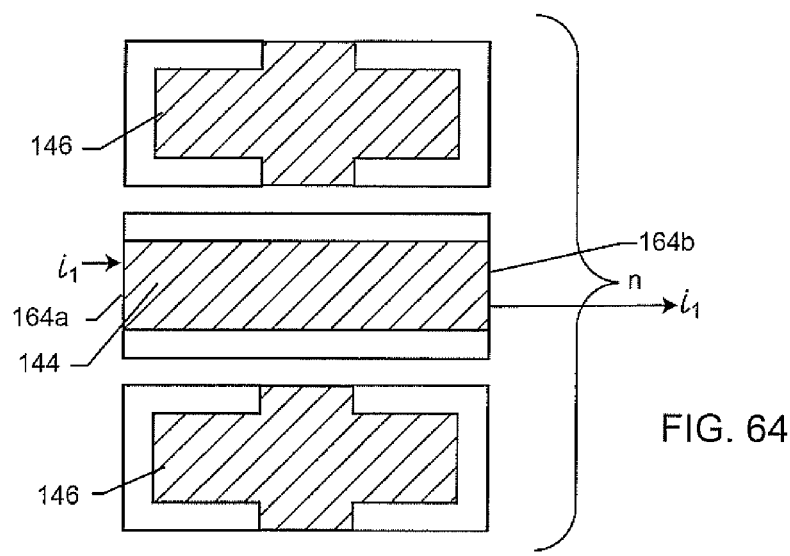
FIG. 64 is very similar to prior art FIG. 18 that illustrated a flat-through type of feedthrough capacitor.
Figure 65:
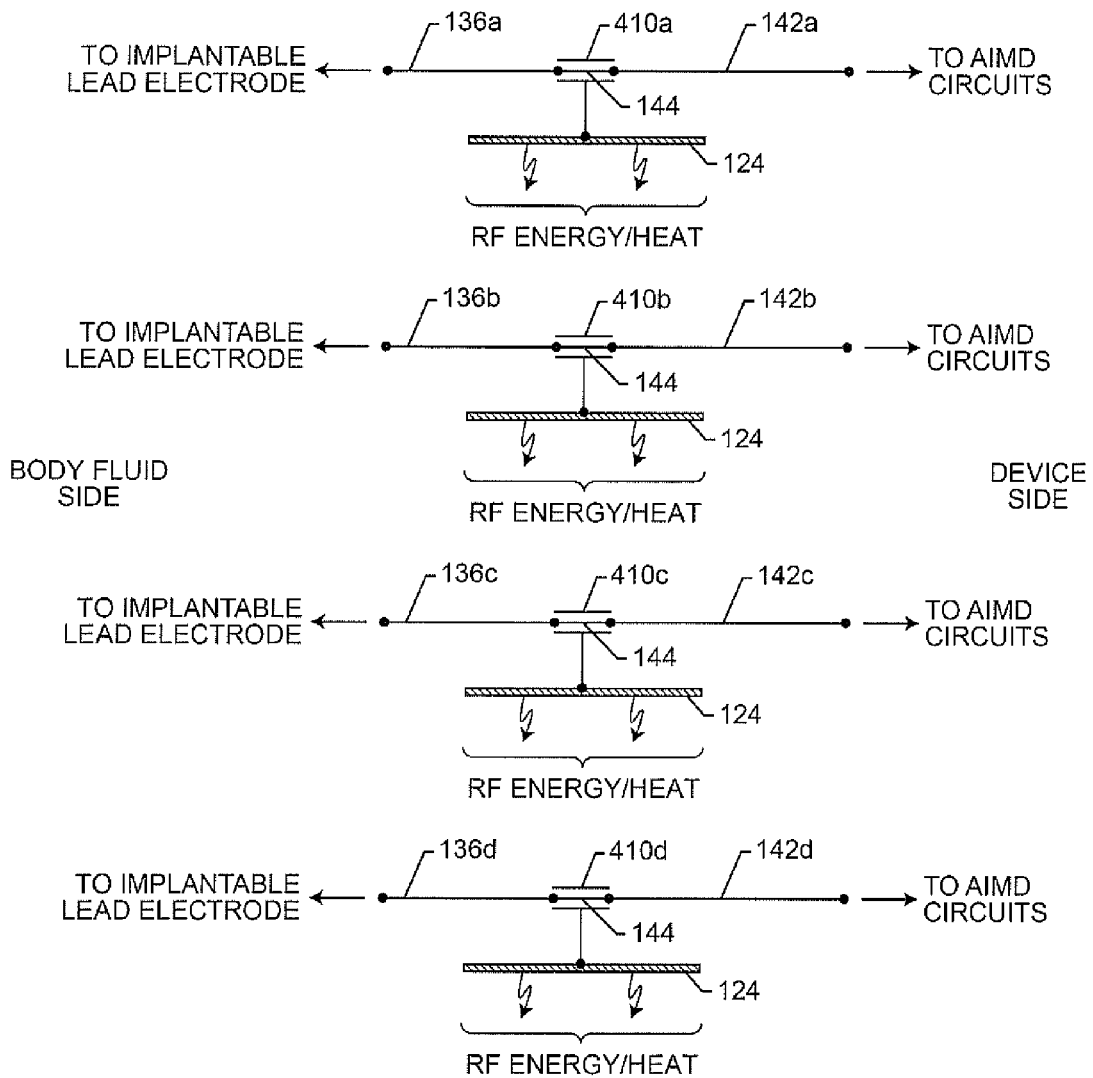
FIG. 65 is the electrical schematic representation of FIGS. 63-64.

FIG. 63 and FIG. 64 are very similar to prior art FIGS. 17 and 18 that illustrated a flat-through type of feedthrough capacitor. These types of capacitors are unique in that the circuit current $i_1$ must pass through its own electrode plates. The circuit diagram for such a capacitor 410 is a feedthrough capacitor shown in FIG. 65. However, instead of having a leadwire going through the center of the feedthrough capacitor, one actually has the active electrode plates 144 of FIG. 18 going through the center of the feedthrough capacitor. In accordance with the present invention, the capacitor dielectric would have a k<1000, a very high electrode plate count and an ESR generally <0.5Ω at the MRI RF-pulsed frequency.

Referring once again to FIG. 63, one can see that this capacitor 410" would be installed on the circuit board of an AIMD a little differently. This would require a break in the circuit traces 178a and 178b, such that the circuit trace current allows current $i_1$ to pass all the way through it. It will be understood to those skilled in the art how to make this simple modification to the circuit boards 130, as previously illustrated in FIGS. 56 and 57.

Referring once again to FIG. 63, one can see that there is a ground connection 182a and 182b. This ground connection will be routed to the AIMD housing 124. As previously described, a preferable way to do this would be by means of a wide grounding strap which would minimize inductance in the ground circuit trace.

Figure 70:
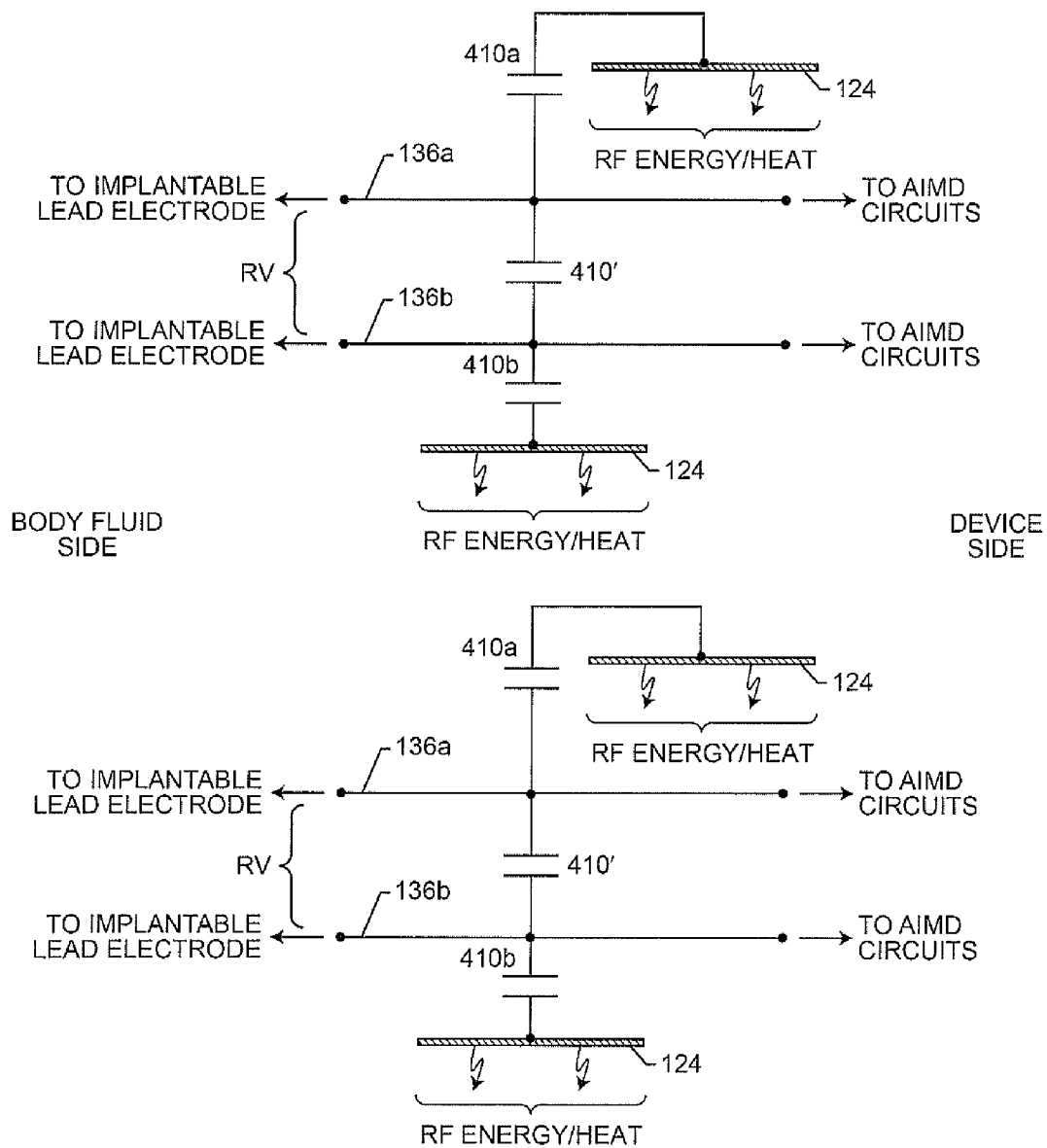
FIG. 70 shows the electrical schematic representation of FIGS. 66-69.

FIG. 66 is similar in outline to the flat-through capacitor of FIG. 17. However, FIG. 66 has a much different internal electrode arrangement that is known in the industry as the X2Y attenuator. The X2Y attenuator has a line-to-line capacitor as illustrated in FIG. 70 as 410' and 410". For example, if lead conductors 136a and 136b were directed to the right ventricle (RV), they would be directed to a right ventricle distal electrode and ring electrode. In a different implanted lead, directed into the right atrium (RA), it could have another tip and ring electrode connected to conductors 136c and 136d. Capacitor 410' and 410" provide a great deal of differential mode attenuation between the two lines. For example, if there was a large differential signal across the right ventricle lead, capacitor 410' would divert that signal and prevent it from reaching AIMD electronics. Importantly, in accordance with the present invention, there are also capacitors to ground in the X2Y attenuator. These are labeled 410a and 410b. These (work horse) capacitors would be the one that primarily divert the high frequency RF energy from the implanted lead conductors through the hermetic seal, through the diverter capacitors 410a and 410b, to the AIMD housing 124. Therefore, in accordance with the present invention, the X2Y attenuator would be of a low k dielectric (no greater than 1000 k) and have a very low ESR (<0.5Ω) and have a relatively high number of electrode plates as this is particularly important for the diverter capacitors 410a and 410b.

Although several embodiments of the invention have been described in detail for purposes of illustration, various modifications of each may be made without departing from the spirit and scope of the invention. Accordingly, the invention is not to be limited, except as by the appended claims.

What is claimed is:

1. An active implantable medical device (AIMD), comprising:
   a) a device housing containing electronic circuits for the AIMD, the device housing defining a body fluid side and a device side, wherein the body fluid side is located outside the device housing and the device side is located inside the device housing;
   b) an electrically conductive ferrule sealed in a housing opening in the device housing, the ferrule defining a ferrule opening extending from a ferrule device side to a ferrule body fluid side;
   c) an insulator at least partially residing in the ferrule opening where a first hermetic seal connects the insulator to the ferrule, wherein the insulator extends from an insulator body fluid side to an insulator device side, and wherein at least one insulator passageway extends through the insulator from the insulator device side to the insulator body fluid side;
   d) a conductive pathway disposed in the insulator passageway where a second hermetic seal connects the conductive pathway to the insulator in a non-conductive relation with the ferrule and the device housing, wherein the conductive pathway extends from a conductive pathway body fluid side to a conductive pathway device side;
   e) a circuit board residing inside the device housing;
   f) at least one filter capacitor disposed on the circuit board, the filter capacitor comprising:
      i) a dielectric having a dielectric constant greater than zero up to 200 and a temperature coefficient of capacitance (TCC) within the range of plus 400 to minus 7112 parts per million per degree centigrade (ppm/° C.);
      ii) at least two active electrode plates and at least two ground electrode plates interleaved in the dielectric in a capacitive relationship with each other; and
      iii) an active metallization connected to the at least two active electrode plates and a ground metallization connected to the at least two ground electrode plates; and
   g) an active electrical connection material electrically coupling the active metallization of the filter capacitor to the conductive pathway device side; and
   h) a ground electrical connection material electrically coupling the ground metallization of the filter capacitor to the ferrule or the device housing or, to both the ferrule and the device housing,
   i) wherein the filter capacitor has:
      i) a capacitance of between 10 and 20,000 picofarads,
      ii) wherein an equivalent series resistance (ESR) is the sum of a dielectric loss plus an ohmic loss, and the capacitor's dielectric loss tangent measured in ohms at an MRI RF pulsed frequency or range of frequencies is less than five percent of the capacitor's ESR, and
      iii) wherein the capacitor's ESR at the MRI RF pulsed frequency or range of frequencies is greater than zero, but less than 2.0 ohms, and
   j) wherein the filter capacitor is the first filter capacitor electrically connected to the conductive pathway device side and to the ferrule or the device housing or, to both the ferrule and the device housing.

2. The AIMD of claim 1 wherein the capacitance varies no more than plus or minus one percent from minus 55° C. to plus 125° C., and the capacitor's ESR is less than two ohms at the MRI RF pulsed frequency or range of frequencies.

3. The AIMD of claim 1, wherein the capacitor's ESR at the MRI RF pulsed frequency or range of frequencies is greater than zero, but less than 0.5 ohm.

4. The AIMD of claim 1, wherein the filter capacitor is a first capacitor element connected to the conductive pathway and being of a multi-element broadband lowpass filter having at least one inductor, the multi-element broadband lowpass filter forming one of the group consisting of an L filter, a reverse L filter, a Pi filter, a T filter, an LL filter, a reverse LL filter, and an n-element lowpass filter.

5. The AIMD of claim 1 wherein the filter capacitor is selected from the group consisting of a monolithic ceramic feedthrough filter capacitor, multilayer ceramic capacitor (MLCC), a flat-through capacitor, a chip capacitor, and an X2Y attenuator.

6. The AIMD of claim 1, wherein the MRI RF pulsed frequency is 64 MHz or 128 MHz or the MRI RF pulsed frequency is a range of frequencies centered at 64 MHz or 128 MHz.

7. The AIMD of claim 1, wherein the capacitance is between 350 and 10,000 picofarads.

8. The AIMD of claim 1, wherein the dielectric constant is greater than zero, but less than 90.

9. The AIMD of claim 1, wherein the dielectric constant is greater than zero, but less than 60.

10. The AIMD of claim 1, wherein the capacitor's ESR at the MRI RF pulsed frequency or range of frequencies is greater than zero, but less than 0.1 ohm.

11. The AIMD of claim 1, wherein the first hermetic seal comprises a first insulator metallization and a first gold braze hermetically sealing the ferrule to the insulator at the first metallization.

12. The AIMD of claim 1, wherein the second hermetic seal comprises a second insulator metallization in the insulator passageway and a second gold braze hermetically sealing the conductive pathway to the insulator at the second metallization.

13. The AIMD of claim 1, wherein the conductive pathway is selected from a conductive wire, a platinum fill, and a sintered conductive paste, and combinations thereof.

14. The AIMD of claim 13, wherein the conductive fill and the conductive paste are characterized as having been co-fired with an alumina ceramic serving as the insulator.

15. The AIMD of claim 1, wherein the circuit board supports an active circuit trace spaced from a ground circuit trace, and wherein the active circuit trace comprises at least a portion of the active electrical connection material and the ground circuit trace comprises at least a portion of the ground electrical connection material.

16. The AIMD of claim 15, wherein the active circuit trace is electrically connected to the conductive pathway device side, and the ground circuit trace is electrically connected to at least one of the first hermetic seal, the ferrule device side, or the device housing.

17. The AIMD of claim 1, wherein the ground electrical connection material comprises at least one ground plate comprising the circuit board.

18. The AIMD of claim 1, wherein at least one of the active and ground electrical connection materials comprise at least one of the group consisting of a solder, a braze, a thermal-setting conductive material, and a conductive polyimide.

19. An active implantable medical device (AIMD), comprising:
a) a device housing containing electronic circuits for the AIMD, the device housing defining a body fluid side and a device side, wherein the body fluid side is located outside the device housing and the device side is located inside the device housing;
b) an electrically conductive ferrule sealed in a housing opening in the device housing, the ferrule defining a ferrule opening extending from a ferrule device side to a ferrule body fluid side;
c) an insulator at least partially residing in the ferrule opening where a first hermetic seal connects the insulator to the ferrule, wherein the insulator extends from an insulator body fluid side to an insulator device side, and wherein at least one insulator passageway extends through the insulator from the insulator device side to the insulator body fluid side;
d) a conductive pathway disposed in the insulator passageway where a second hermetic seal connects the conductive pathway to the insulator in a non-conductive relation with the ferrule and the device housing, wherein the conductive pathway extends from a conductive pathway body fluid side to a conductive pathway device side;
e) a circuit board residing inside the device housing, wherein a circuit board active via extends through the circuit board, and wherein the conductive pathway device side extends outwardly beyond the insulator device side and resides in the circuit board active via;
f) at least one filter capacitor disposed on the circuit board, the filter capacitor comprising:
i) a dielectric having a dielectric constant greater than zero up to 200 and a temperature coefficient of capacitance (TCC) within the range of plus 400 to minus 7112 parts per million per degree centigrade (ppm/° C.);
ii) at least two active electrode plates and at least two ground electrode plates interleaved in the dielectric in a capacitive relationship with each other; and
iii) an active metallization connected to the at least two active electrode plates and a ground metallization connected to the at least two ground electrode plates; and
g) an active electrical connection material electrically coupling the active metallization of the filter capacitor to the conductive pathway device side at or adjacent to the circuit board via; and
h) a ground electrical connection material electrically coupling the ground metallization of the filter capacitor to the ferrule or the device housing or, to both the ferrule and the device housing,
i) wherein the filter capacitor has:
i) a capacitance of between 10 and 20,000 picofarads,
ii) wherein an equivalent series resistance (ESR) is the sum of a dielectric loss plus an ohmic loss, and the capacitor's dielectric loss tangent measured in ohms at an MRI RF pulsed frequency or range of frequencies is less than five percent of the capacitor's ESR, and
iii) wherein the capacitor's ESR at the MRI RF pulsed frequency or range of frequencies is greater than zero, but less than 2.0 ohms, and
j) wherein the filter capacitor is the first filter capacitor electrically connected to the conductive pathway device side and to the ferrule or the device housing or, to both the ferrule and the device housing.

20. The AIMD of claim 19, wherein the conductive pathway is selected from a conductive wire, a platinum fill, and a sintered conductive paste, and combinations thereof.

21. The AIMD of claim 20, wherein the conductive fill and the conductive paste are characterized as having been co-fired with an alumina ceramic serving as the insulator.

22. The AIMD of claim 19, wherein the circuit board supports an active circuit trace spaced from a ground circuit trace, and wherein the active circuit trace comprises at least a portion of the active electrical connection material and the ground circuit trace comprises at least a portion of the ground electrical connection material.

23. The AIMD of claim 22, wherein the active circuit trace is electrically connected to the conductive pathway device side, and the ground circuit trace is electrically connected to at least one of the first hermetic seal, the ferrule device side, or the device housing.

24. The AIMD of claim 19, wherein the ground electrical connection material comprises at least one ground plate comprising the circuit board.

* * * * *